United States Patent
Keasler et al.

(10) Patent No.: US 9,926,214 B2
(45) Date of Patent: *Mar. 27, 2018

(54) USE OF PERACETIC ACID/HYDROGEN PEROXIDE AND PEROXIDE-REDUCING AGENTS FOR TREATMENT OF DRILLING FLUIDS, FRAC FLUIDS, FLOWBACK WATER AND DISPOSAL WATER

(71) Applicant: Ecolab USA Inc., St. Paul, MN (US)

(72) Inventors: Victor Keasler, Sugarland, TX (US);
Renato De Paula, Houston, TX (US);
Junzhong Li, Apple Valley, MN (US);
David D. McSherry, St. Paul, MN (US); Brandon Herdt, Hastings, MN (US); Richard Staub, Lakeville, MN (US); Robert J. Ryther, St. Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 125 days.

This patent is subject to a terminal disclaimer.

(21) Appl. No.: 13/798,281

(22) Filed: Mar. 13, 2013

(65) Prior Publication Data

US 2013/0264293 A1    Oct. 10, 2013

Related U.S. Application Data

(60) Provisional application No. 61/617,814, filed on Mar. 30, 2012.

(51) Int. Cl.
*A01N 25/32* (2006.01)
*A01N 25/22* (2006.01)
(Continued)

(52) U.S. Cl.
CPC ............... *C02F 1/70* (2013.01); *A01N 25/22* (2013.01); *A01N 25/32* (2013.01); *A01N 37/16* (2013.01);
(Continued)

(58) Field of Classification Search
CPC .... C02F 1/50; C02F 1/70; C02F 1/722; C02F 1/725; C02F 1/76; C02F 2303/04;
(Continued)

(56) References Cited

U.S. PATENT DOCUMENTS 2,609,391 A    9/1952    Greenspan et al.
2,955,905 A    10/1960   Davies et al.
(Continued)

FOREIGN PATENT DOCUMENTS

CA    2084172 A1    6/1993
CA    2 152 908 C   7/1997
(Continued)

OTHER PUBLICATIONS

E.I. du Pont de Nemours & Co., DE 1024514—English Abstract Feb. 20, 1958.
(Continued)

*Primary Examiner* — Lucas Stelling
(74) *Attorney, Agent, or Firm* — McKee, Voorhees & Sease, PLC

(57) ABSTRACT

Methods for the use of peracid compositions having decreased hydrogen peroxide concentration for various water treatments, including oil- and gas-field operations, and/or other aseptic treatments are disclosed. In numerous aspects, peracetic acid is the preferred peracid and is treated with a peroxide-reducing agent to substantially reduce the hydrogen peroxide content. Methods for using the treated peracid compositions for treatment of drilling fluids, frac fluids, flow back waters and disposal waters are also disclosed for improving water condition, reducing oxidizing damage associated with hydrogen peroxide and/or reducing bacteria infestation.

20 Claims, 37 Drawing Sheets

(51) Int. Cl.
  *A01N 37/16* (2006.01)
  *C02F 1/70* (2006.01)
  *C02F 1/72* (2006.01)
  *C02F 1/76* (2006.01)
  *E21B 21/06* (2006.01)
  *E21B 43/00* (2006.01)
  *C02F 1/50* (2006.01)
  *C02F 3/34* (2006.01)
  C02F 103/08 (2006.01)
  C02F 103/10 (2006.01)
  C02F 103/36 (2006.01)
  C09K 8/60 (2006.01)
  C09K 8/66 (2006.01)

(52) U.S. Cl.
  CPC ............... *C02F 1/50* (2013.01); *C02F 1/722* (2013.01); *C02F 1/76* (2013.01); *C02F 3/342* (2013.01); *E21B 21/068* (2013.01); *E21B 43/00* (2013.01); *C02F 2103/08* (2013.01); *C02F 2103/10* (2013.01); *C02F 2103/365* (2013.01); *C02F 2303/04* (2013.01); *C02F 2303/08* (2013.01); *C02F 2303/18* (2013.01); *C02F 2303/20* (2013.01); *C02F 2305/02* (2013.01); *C09K 8/605* (2013.01); *C09K 8/66* (2013.01); *C09K 2208/28* (2013.01); *C09K 2208/32* (2013.01); *Y02W 10/37* (2015.05)

(58) Field of Classification Search
  CPC ........... C02F 2303/08; C02F 2103/08; C02F 2103/10; C02F 2305/026; C02F 2303/18; C02F 2303/20; C02F 2103/365; C02F 2305/02; E21B 43/00; E21B 21/068; A01N 25/22; A01N 25/32; A01N 37/16; C09K 8/605; C09K 8/66; C09K 2208/28; C09K 2208/32; Y02W 10/37
  See application file for complete search history.

(56) References Cited

U.S. PATENT DOCUMENTS

| | | |
|---|---|---|
| 3,053,633 A | 9/1962 | Dunlop et al. |
| 3,130,169 A | 4/1964 | Blumbergs et al. |
| 3,156,654 A | 11/1964 | Konecny et al. |
| 3,256,198 A | 6/1966 | Matzner |
| 3,272,750 A | 9/1966 | Chase |
| 3,414,593 A | 12/1968 | Robson et al. |
| 3,432,546 A | 3/1969 | Oringer et al. |
| 3,847,830 A | 11/1974 | Williams et al. |
| 3,925,234 A | 12/1975 | Hachmann et al. |
| 3,956,159 A | 5/1976 | Jones |
| 3,969,258 A | 7/1976 | Carandang et al. |
| 4,003,841 A | 1/1977 | Hachmann et al. |
| 4,013,575 A | 3/1977 | Castrantas et al. |
| 4,051,058 A | 9/1977 | Böwing et al. |
| 4,051,059 A | 9/1977 | Bowing |
| 4,100,095 A | 7/1978 | Hutchins et al. |
| 4,126,573 A | 11/1978 | Johnston |
| 4,129,517 A | 12/1978 | Eggensperger et al. |
| 4,144,179 A | 3/1979 | Chatterji |
| 4,170,453 A | 10/1979 | Kitko |
| 4,233,235 A | 11/1980 | Camden et al. |
| 4,259,201 A | 3/1981 | Cockrell, Jr. et al. |
| 4,297,298 A | 10/1981 | Crommelynck et al. |
| 4,311,598 A * | 1/1982 | Verachtert .................... 210/757 |
| 4,367,156 A | 1/1983 | Diehl |
| 4,370,251 A | 1/1983 | Liao et al. |
| 4,374,035 A | 2/1983 | Bossu |
| 4,391,723 A | 7/1983 | Bacon et al. |
| 4,391,724 A | 7/1983 | Bacon |
| 4,412,934 A | 11/1983 | Chung et al. |
| 4,430,236 A | 2/1984 | Franks |
| 4,470,919 A | 9/1984 | Goffinet et al. |
| 4,473,507 A | 9/1984 | Bossu |
| 4,483,778 A | 11/1984 | Thompson et al. |
| 4,486,327 A | 12/1984 | Murphy et al. |
| 4,529,534 A | 7/1985 | Richardson |
| 4,540,721 A | 9/1985 | Staller |
| 4,587,264 A | 5/1986 | Jourdan-Laforte et al. |
| 4,588,506 A | 5/1986 | Raymond et al. |
| 4,617,090 A | 10/1986 | Chum et al. |
| 4,655,781 A | 4/1987 | Hsieh et al. |
| 4,681,592 A | 7/1987 | Hardy et al. |
| 4,743,447 A | 5/1988 | Le Rouzic et al. |
| 4,778,618 A | 10/1988 | Fong et al. |
| 4,783,278 A | 11/1988 | Sanderson et al. |
| 4,786,431 A | 11/1988 | Broze et al. |
| 4,797,225 A | 1/1989 | Broze et al. |
| 4,846,992 A | 7/1989 | Fonsny |
| 4,853,143 A | 8/1989 | Hardy et al. |
| 4,879,057 A | 11/1989 | Dankowski et al. |
| 4,917,815 A | 4/1990 | Beilfuss et al. |
| 4,957,647 A | 9/1990 | Zielske |
| 4,964,870 A | 10/1990 | Fong et al. |
| 5,004,558 A | 4/1991 | Dyroff et al. |
| 5,019,292 A | 5/1991 | Baeck et al. |
| 5,030,240 A | 7/1991 | Wiersema et al. |
| 5,073,285 A | 12/1991 | Liberati et al. |
| 5,098,598 A | 3/1992 | Sankey et al. |
| 5,117,049 A | 5/1992 | Venturello et al. |
| 5,139,788 A | 8/1992 | Schmidt |
| 5,143,641 A | 9/1992 | Nunn |
| 5,160,656 A | 11/1992 | Carron et al. |
| 5,196,133 A | 3/1993 | Leslie et al. |
| 5,200,189 A | 4/1993 | Oakes et al. |
| 5,250,212 A | 10/1993 | de Buzzaccarini et al. |
| 5,250,707 A | 10/1993 | Inaba et al. |
| 5,264,229 A | 11/1993 | Mannig et al. |
| 5,266,587 A | 11/1993 | Sankey et al. |
| 5,268,003 A | 12/1993 | Coope et al. |
| 5,274,369 A | 12/1993 | Tsunoda et al. |
| 5,296,239 A | 3/1994 | Colery et al. |
| 5,310,774 A | 5/1994 | Farrar |
| 5,314,687 A | 5/1994 | Oakes et al. |
| 5,349,083 A | 9/1994 | Brougham et al. |
| 5,362,899 A | 11/1994 | Campbell |
| 5,288,746 A | 12/1994 | Pramod |
| 5,374,369 A | 12/1994 | Angevaare et al. |
| 5,382,571 A | 1/1995 | Granger et al. |
| 5,383,977 A | 1/1995 | Pearce |
| 5,398,506 A | 3/1995 | Martin |
| 5,409,629 A | 4/1995 | Shulman et al. |
| 5,431,849 A | 7/1995 | Damhus et al. |
| 5,433,881 A | 7/1995 | Townend et al. |
| 5,435,808 A | 7/1995 | Holzhauer et al. |
| 5,447,648 A | 9/1995 | Steindorf |
| 5,453,214 A | 9/1995 | van den Berg et al. |
| 5,463,112 A | 10/1995 | Sankey et al. |
| 5,464,563 A | 11/1995 | Moore et al. |
| 5,466,825 A | 11/1995 | Carr et al. |
| 5,472,619 A | 12/1995 | Holzhauer et al. |
| 5,486,212 A | 1/1996 | Mitchell et al. |
| 5,496,728 A | 3/1996 | Hardy et al. |
| 5,503,765 A | 4/1996 | Schepers et al. |
| 5,505,740 A | 4/1996 | Kong et al. |
| 5,525,121 A | 6/1996 | Heffner et al. |
| 5,545,374 A | 8/1996 | French et al. |
| 5,565,231 A | 10/1996 | Malone et al. |
| 5,576,282 A | 11/1996 | Miracle et al. |
| 5,589,507 A | 12/1996 | Hall, II et al. |
| 5,595,967 A | 1/1997 | Miracle et al. |
| 5,599,781 A | 2/1997 | Haeggberg et al. |
| 5,624,634 A | 4/1997 | Brougham |
| 5,632,676 A | 5/1997 | Kurschner et al. |
| 5,635,195 A | 6/1997 | Hall, II et al. |
| 5,637,755 A | 6/1997 | Nagumo et al. |
| 5,647,997 A | 7/1997 | Holzhauer et al. |
| 5,672,739 A | 9/1997 | Varadaraj et al. |
| 5,681,805 A | 10/1997 | Scheuing et al. |
| 5,683,724 A * | 11/1997 | Hei .................... C02F 1/722 210/759 |

(56) References Cited

U.S. PATENT DOCUMENTS

| | | |
|---|---|---|
| 5,683,977 A | 11/1997 | Jureller et al. |
| 5,698,506 A | 12/1997 | Angevaare et al. |
| 5,716,923 A | 2/1998 | MacBeath |
| 5,718,910 A | 2/1998 | Oakes et al. |
| 5,755,977 A * | 5/1998 | Gurol ............... C02F 1/725 |
| | | 210/759 |
| 5,767,308 A | 6/1998 | Thiele et al. |
| 5,780,064 A | 7/1998 | Meisters et al. |
| 5,785,867 A | 7/1998 | LaZonby et al. |
| 5,814,592 A | 9/1998 | Kahn et al. |
| 5,827,447 A | 10/1998 | Tamura et al. |
| 5,827,808 A | 10/1998 | Appleby et al. |
| 5,840,343 A | 11/1998 | Hall, II et al. |
| 5,872,092 A | 2/1999 | Kong-Chan et al. |
| 5,880,083 A | 3/1999 | Beaujean et al. |
| 5,914,303 A | 6/1999 | Sankey et al. |
| 5,929,012 A | 7/1999 | Del Duca et al. |
| 5,965,033 A | 10/1999 | Huss |
| 5,965,785 A | 10/1999 | Braden et al. |
| 5,968,885 A | 10/1999 | Del Duca et al. |
| 5,977,403 A | 11/1999 | Byers |
| 5,998,350 A | 12/1999 | Burns et al. |
| 6,010,729 A | 1/2000 | Gutzmann et al. |
| 6,022,381 A | 2/2000 | Dias et al. |
| 6,049,002 A | 4/2000 | Mattila et al. |
| 6,103,286 A | 8/2000 | Gutzmann et al. |
| 6,110,883 A | 8/2000 | Petri et al. |
| 6,136,769 A | 10/2000 | Asano et al. |
| 6,156,156 A | 12/2000 | Rousu et al. |
| 6,165,483 A | 12/2000 | Hei et al. |
| 6,177,393 B1 | 1/2001 | McGregor et al. |
| 6,183,763 B1 | 2/2001 | Beerse et al. |
| 6,183,807 B1 | 2/2001 | Gutzmann et al. |
| 6,207,632 B1 | 3/2001 | Brooker et al. |
| 6,211,237 B1 | 4/2001 | Huss et al. |
| 6,221,341 B1 | 4/2001 | Montgomery |
| 6,238,685 B1 | 5/2001 | Hei et al. |
| 6,262,013 B1 | 7/2001 | Smith et al. |
| 6,277,804 B1 | 8/2001 | Kahn et al. |
| 6,284,793 B1 | 9/2001 | Fuchs et al. |
| 6,294,186 B1 | 9/2001 | Beerse et al. |
| 6,310,025 B1 | 10/2001 | Del Duca et al. |
| 6,326,032 B1 | 12/2001 | Richter et al. |
| 6,346,279 B1 | 2/2002 | Rochon |
| 6,384,008 B1 | 5/2002 | Parry |
| 6,399,564 B1 | 6/2002 | Speed et al. |
| 6,407,052 B2 | 6/2002 | Gassenmeier et al. |
| 6,417,151 B1 | 7/2002 | Grothus et al. |
| 6,432,661 B1 | 8/2002 | Heitfeld et al. |
| 6,436,885 B2 | 8/2002 | Biedermann et al. |
| 6,444,634 B1 | 9/2002 | Mason et al. |
| 6,503,876 B1 | 1/2003 | Broeckx |
| 6,528,471 B1 | 3/2003 | Del Duca et al. |
| 6,545,047 B2 | 4/2003 | Gutzmann et al. |
| 6,566,318 B2 | 5/2003 | Perkins et al. |
| 6,569,286 B1 | 5/2003 | Withenshaw et al. |
| 6,576,602 B1 | 6/2003 | Smerznak et al. |
| 6,589,565 B1 | 7/2003 | Richter et al. |
| 6,599,871 B2 | 7/2003 | Smith |
| 6,602,845 B2 | 8/2003 | Connor et al. |
| 6,607,710 B1 | 8/2003 | Ito et al. |
| 6,627,657 B1 | 9/2003 | Hilgren et al. |
| 6,635,286 B2 | 10/2003 | Hei et al. |
| 6,649,140 B2 | 11/2003 | Paparatto et al. |
| 6,686,324 B2 | 2/2004 | Ramirez et al. |
| 6,689,732 B1 | 2/2004 | Guedira et al. |
| 6,696,093 B2 | 2/2004 | Ney et al. |
| 6,770,774 B2 | 8/2004 | Van De Bovenkamp-Bouwman et al. |
| 6,803,057 B2 | 10/2004 | Ramirez et al. |
| 6,806,246 B2 | 10/2004 | Preissner et al. |
| 6,830,591 B1 | 12/2004 | Wang et al. |
| 6,866,749 B2 | 3/2005 | Delmas et al. |
| 6,878,680 B2 | 4/2005 | Kitko et al. |
| 6,919,304 B2 | 7/2005 | Dykstra et al. |
| 7,012,053 B1 | 3/2006 | Barnabas et al. |
| 7,060,136 B1 | 6/2006 | Zeiher et al. |
| 7,078,373 B2 | 7/2006 | Burrows et al. |
| 7,148,351 B2 | 12/2006 | Morris et al. |
| 7,169,236 B2 | 1/2007 | Zeiher et al. |
| 7,189,385 B2 | 3/2007 | Montgomery |
| 7,217,295 B2 | 5/2007 | Samain et al. |
| 7,243,664 B2 | 7/2007 | Berger et al. |
| 7,431,775 B2 | 10/2008 | Wang et al. |
| 7,448,255 B2 | 11/2008 | Hoots et al. |
| 7,498,051 B2 | 3/2009 | Man et al. |
| 7,541,324 B2 | 6/2009 | Reinhardt et al. |
| 7,569,232 B2 | 8/2009 | Man et al. |
| 7,569,528 B2 | 8/2009 | Lant et al. |
| 7,598,218 B2 | 10/2009 | Stolle et al. |
| 7,601,789 B2 | 10/2009 | Morris et al. |
| 7,618,545 B2 | 11/2009 | Wakao et al. |
| 7,686,892 B2 | 3/2010 | Smets et al. |
| 7,723,083 B2 | 4/2010 | DiCosimo et al. |
| 7,771,737 B2 | 8/2010 | Man et al. |
| 7,863,234 B2 | 1/2011 | Maki et al. |
| 7,875,720 B2 | 1/2011 | Morris et al. |
| 7,887,641 B2 | 2/2011 | Man et al. |
| 7,910,371 B2 | 3/2011 | Johnson |
| 7,915,445 B2 | 3/2011 | Maatta et al. |
| 7,919,122 B2 | 4/2011 | Okano et al. |
| 7,922,828 B2 | 4/2011 | Smith et al. |
| 7,949,432 B2 | 5/2011 | Rice |
| 7,981,679 B2 | 7/2011 | Rice |
| 7,985,318 B2 | 7/2011 | Shevchenko et al. |
| 8,017,409 B2 | 9/2011 | Tokhtuev et al. |
| 8,030,351 B2 | 10/2011 | Gutzmann et al. |
| 8,080,404 B1 | 12/2011 | Turetsky et al. |
| 8,084,756 B2 | 12/2011 | Tokhtuev et al. |
| 8,110,603 B2 | 2/2012 | Kawabata et al. |
| 8,119,412 B2 | 2/2012 | Kraus |
| 8,153,573 B2 | 4/2012 | Miralles et al. |
| 8,178,336 B2 | 5/2012 | Derkx et al. |
| 8,226,939 B2 | 7/2012 | Herdt et al. |
| 8,231,917 B2 | 7/2012 | Herdt et al. |
| 8,236,573 B2 | 8/2012 | Tokhtuev et al. |
| 8,241,624 B2 | 8/2012 | Herdt et al. |
| 8,309,507 B2 | 11/2012 | Fernandez Prieto et al. |
| 8,344,026 B2 | 1/2013 | Li et al. |
| 2001/0054201 A1 | 12/2001 | Wang et al. |
| 2002/0007516 A1 | 1/2002 | Wang |
| 2002/0055043 A1 | 5/2002 | Morikawa et al. |
| 2002/0064565 A1 | 5/2002 | Karagoezian |
| 2002/0086903 A1 | 7/2002 | Giambrone et al. |
| 2002/0157189 A1 | 10/2002 | Wang et al. |
| 2002/0188026 A1 | 12/2002 | Singh et al. |
| 2003/0045443 A1 | 3/2003 | Korber et al. |
| 2003/0100468 A1 | 5/2003 | Smerznak et al. |
| 2003/0100469 A1 | 5/2003 | Connor et al. |
| 2003/0148909 A1 | 8/2003 | Del Duca et al. |
| 2003/0154556 A1 | 8/2003 | Del Duca et al. |
| 2003/0234382 A1 | 12/2003 | Sato et al. |
| 2003/0235623 A1 | 12/2003 | Van Oosterom |
| 2004/0002616 A1 | 1/2004 | Preto et al. |
| 2004/0010858 A1 | 1/2004 | Detering et al. |
| 2004/0016060 A1 | 1/2004 | Detering et al. |
| 2004/0025262 A1 | 2/2004 | Hamers et al. |
| 2004/0033269 A1 | 2/2004 | Hei et al. |
| 2004/0035537 A1 | 2/2004 | Delmas et al. |
| 2004/0072718 A1 | 4/2004 | Price et al. |
| 2004/0077514 A1 | 4/2004 | Price et al. |
| 2004/0107506 A1 | 6/2004 | Detering et al. |
| 2004/0139559 A1 | 7/2004 | Detering et al. |
| 2004/0266653 A1 | 12/2004 | Delplancke et al. |
| 2005/0000908 A1 | 1/2005 | Karlsson et al. |
| 2005/0008526 A1 | 1/2005 | Bianchetti et al. |
| 2005/0222003 A1 | 10/2005 | Gagliardi et al. |
| 2005/0226800 A1 | 10/2005 | Wang et al. |
| 2005/0281773 A1 | 12/2005 | Wieland et al. |
| 2006/0040847 A1 | 2/2006 | Weibel |
| 2006/0088498 A1 | 4/2006 | Martin et al. |
| 2006/0172909 A1 | 8/2006 | Schmiedel et al. |
| 2006/0173209 A1 | 8/2006 | Vineyard et al. |
| 2006/0199742 A1 | 9/2006 | Arisz et al. |

(56) References Cited

U.S. PATENT DOCUMENTS

| | | |
|---|---|---|
| 2006/0254001 A1 | 11/2006 | Hoeffkes et al. |
| 2006/0257964 A1 | 11/2006 | Larose |
| 2006/0276366 A1 | 12/2006 | Deljosevic et al. |
| 2006/0289364 A1 | 12/2006 | Wakao et al. |
| 2007/0010420 A1 | 1/2007 | Lange et al. |
| 2007/0042924 A1 | 2/2007 | DiCosimo et al. |
| 2007/0087954 A1 | 4/2007 | Wang et al. |
| 2007/0102359 A1* | 5/2007 | Lombardi et al. ............ 210/639 |
| 2007/0113875 A1 | 5/2007 | Wang et al. |
| 2007/0163779 A1 | 7/2007 | Rae et al. |
| 2007/0173430 A1 | 7/2007 | Souter et al. |
| 2007/0257127 A1* | 11/2007 | Iverson .................... C02F 1/78 |
| | | 239/10 |
| 2007/0281002 A1 | 12/2007 | Morales et al. |
| 2008/0064619 A1 | 3/2008 | Bastigkeit et al. |
| 2008/0095861 A1 | 4/2008 | Walker |
| 2008/0146482 A1 | 6/2008 | Schneiderman et al. |
| 2008/0176784 A1 | 7/2008 | Clowes et al. |
| 2008/0194449 A1 | 8/2008 | Becker et al. |
| 2008/0312107 A1 | 12/2008 | Harris et al. |
| 2009/0005286 A1 | 1/2009 | Detering et al. |
| 2009/0011971 A1 | 1/2009 | Evers |
| 2009/0018049 A1 | 1/2009 | Stolle et al. |
| 2009/0047176 A1 | 2/2009 | Cregger et al. |
| 2009/0061017 A1 | 3/2009 | Pedersen et al. |
| 2009/0075856 A1 | 3/2009 | Schmiedel et al. |
| 2009/0088347 A1 | 4/2009 | Mukhopadhyay et al. |
| 2009/0148686 A1 | 6/2009 | Urankar et al. |
| 2009/0175956 A1 | 7/2009 | Buschmann et al. |
| 2009/0188055 A1 | 7/2009 | Bernhardt et al. |
| 2009/0221704 A1 | 9/2009 | Aksela et al. |
| 2009/0249557 A1 | 10/2009 | Maki et al. |
| 2009/0269324 A1 | 10/2009 | Herdt et al. |
| 2009/0294382 A1 | 12/2009 | Fukuyo et al. |
| 2010/0021557 A1 | 1/2010 | Li et al. |
| 2010/0021558 A1 | 1/2010 | Dada et al. |
| 2010/0041579 A1 | 2/2010 | Bianchetti et al. |
| 2010/0048730 A1 | 2/2010 | Li et al. |
| 2010/0084603 A1 | 4/2010 | Narayan et al. |
| 2010/0108566 A1 | 5/2010 | Scattergood et al. |
| 2010/0140186 A1 | 6/2010 | Huang et al. |
| 2010/0160449 A1 | 6/2010 | Rovison, Jr. et al. |
| 2010/0222242 A1 | 9/2010 | Huang et al. |
| 2010/0227000 A1 | 9/2010 | Ames et al. |
| 2010/0286017 A1 | 11/2010 | Righetto |
| 2010/0308260 A1 | 12/2010 | Maki et al. |
| 2011/0168567 A1 | 7/2011 | Smith et al. |
| 2011/0169270 A1 | 7/2011 | Todorof |
| 2011/0171062 A1 | 7/2011 | Wolfe |
| 2011/0173897 A1 | 7/2011 | Schneider |
| 2011/0177145 A1 | 7/2011 | Erkenbrecher, Jr. et al. |
| 2011/0217761 A1 | 9/2011 | Hilgren et al. |
| 2011/0240510 A1 | 10/2011 | De Poortere et al. |
| 2011/0257060 A1 | 10/2011 | Dykstra |
| 2011/0311645 A1* | 12/2011 | Diaz .................... A01N 37/16 |
| | | 424/616 |
| 2012/0012307 A1 | 1/2012 | Nevin |
| 2012/0024525 A1 | 2/2012 | Svarczkopf et al. |
| 2012/0052134 A1 | 3/2012 | Li et al. |
| 2012/0070339 A1 | 3/2012 | Lawal |
| 2012/0085236 A1 | 4/2012 | McCorriston et al. |
| 2012/0085931 A1 | 4/2012 | Burns et al. |
| 2012/0097614 A1 | 4/2012 | Silva et al. |
| 2012/0149121 A1 | 6/2012 | Tokhtuev et al. |
| 2012/0172441 A1 | 7/2012 | Li et al. |
| 2012/0225943 A1 | 9/2012 | Gohl et al. |
| 2012/0321510 A1 | 12/2012 | Herdt et al. |
| 2013/0018097 A1 | 1/2013 | Bolduc et al. |
| 2013/0022496 A1 | 1/2013 | Herdt et al. |
| 2014/0096971 A1 | 4/2014 | Keizer et al. |

FOREIGN PATENT DOCUMENTS

| | | |
|---|---|---|
| CN | 1020197 C | 3/1993 |
| CN | 1092385 A | 12/1993 |
| CN | 1162132 A | 10/1996 |
| CN | 1117298 C | 10/1997 |
| CN | 1231599 A | 10/1999 |
| CN | 1751768 A | 3/2006 |
| CN | 100486668 C | 5/2009 |
| CN | 102066240 A | 5/2011 |
| CN | 102105443 A | 6/2011 |
| CN | 102256484 A | 11/2011 |
| CN | 104703926 B | 12/2016 |
| DE | 1024514 | 2/1958 |
| DE | 197 54 290 A1 | 6/1999 |
| DE | 19853845 A1 | 5/2000 |
| DE | 10011273 A1 | 9/2001 |
| EP | 0 061 393 A1 | 9/1982 |
| EP | 0 068 547 A1 | 1/1983 |
| EP | 0 075 419 A2 | 3/1983 |
| EP | 0122041 A1 | 10/1984 |
| EP | 0 231 632 A2 | 8/1987 |
| EP | 0 233 730 A2 | 8/1987 |
| EP | 0 267 047 A2 | 5/1988 |
| EP | 273775 A2 | 7/1988 |
| EP | 349220 A2 | 1/1990 |
| EP | 387049 A2 | 3/1990 |
| EP | 0 384 911 A2 | 8/1990 |
| EP | 0 395 902 A2 | 11/1990 |
| EP | 0 396 341 A2 | 11/1990 |
| EP | 0 442 549 A2 | 8/1991 |
| EP | 0 280 697 | 9/1992 |
| EP | 0 626 371 A1 | 11/1994 |
| EP | 0 741 776 B1 | 11/1996 |
| EP | 0 751 210 A1 | 1/1997 |
| EP | 0 751 933 B1 | 8/1997 |
| EP | 0 845 526 A2 | 6/1998 |
| EP | 0 906 950 A1 | 4/1999 |
| EP | 1 001 012 A1 | 5/2000 |
| EP | 1 010 749 A2 | 6/2000 |
| EP | 1099750 A2 | 5/2001 |
| EP | 1 247 802 A1 | 10/2002 |
| EP | 1328616 A2 | 7/2003 |
| EP | 1717302 A1 | 4/2008 |
| EP | 1 931 628 B1 | 6/2008 |
| EP | 1328616 B1 | 7/2008 |
| EP | 2329893 A1 | 6/2011 |
| EP | 2 271 410 | 10/2011 |
| EP | 2 522 714 A1 | 11/2012 |
| EP | 2 522 715 A1 | 11/2012 |
| GB | 1041417 A | 9/1966 |
| GB | 1 198 734 | 7/1970 |
| GB | 1 584 170 | 2/1981 |
| GB | 2172897 A | 10/1986 |
| GB | 2177716 A | 1/1987 |
| GB | 2178754 A | 2/1987 |
| GB | 2179364 A | 3/1987 |
| GB | 2179365 A | 3/1987 |
| GB | 2187199 A | 9/1987 |
| GB | 2195124 A | 3/1988 |
| GB | 2195125 A | 3/1988 |
| GB | 2195649 A | 4/1988 |
| GB | 2208233 A | 3/1989 |
| GB | 2279660 A | 1/1995 |
| GB | 2281744 A | 3/1995 |
| GB | 2361687 A | 10/2001 |
| JP | 59206495 A | 11/1984 |
| JP | 60230000 A | 11/1985 |
| JP | 62155203 A | 7/1987 |
| JP | 63165364 A | 7/1988 |
| JP | 01297499 A | 11/1989 |
| JP | 05503507 A | 6/1993 |
| JP | 5186989 | 7/1993 |
| JP | 05507951 A | 11/1993 |
| JP | 06100531 A | 4/1994 |
| JP | 06503372 A | 4/1994 |
| JP | 6305920 A | 11/1994 |
| JP | 06510526 A | 11/1994 |
| JP | H0249765 A | 4/1996 |

(56) References Cited

FOREIGN PATENT DOCUMENTS

| | | |
|---|---|---|
| JP | H0892594 A | 4/1996 |
| JP | H0892595 A | 4/1996 |
| JP | H08143898 A | 6/1996 |
| JP | H08245549 A | 9/1996 |
| JP | 09512042 A | 12/1997 |
| JP | 2000505136 A | 4/2000 |
| JP | 3119174 A | 12/2000 |
| JP | 2000357633 A | 12/2000 |
| JP | 2002105352 A | 4/2002 |
| JP | 2006-45146 A | 2/2006 |
| JP | 2006-45147 A | 2/2006 |
| JP | 2007084589 A | 4/2007 |
| JP | 2007520479 A | 7/2007 |
| JP | 20070523892 A | 8/2007 |
| JP | 2009500415 A | 1/2009 |
| JP | 2011518775 A | 6/2011 |
| JP | 2012126740 A | 7/2012 |
| JP | 2012126741 A | 7/2012 |
| JP | 2012126918 A | 7/2012 |
| JP | 2012149080 A | 8/2012 |
| JP | 5140079 B2 | 2/2013 |
| NZ | 587218 A | 4/2012 |
| RU | 2506300 C2 | 2/2014 |
| WO | WO 90/07501 A1 | 7/1990 |
| WO | WO 91/07375 | 5/1991 |
| WO | 199113058 A1 | 9/1991 |
| WO | 1991014674 A2 | 10/1991 |
| WO | 1991015122 A1 | 10/1991 |
| WO | WO 91/15474 A1 | 10/1991 |
| WO | 1994003580 A1 | 2/1994 |
| WO | WO 94/03395 A1 | 2/1994 |
| WO | WO 94/10284 A1 | 5/1994 |
| WO | WO 94/13776 A1 | 6/1994 |
| WO | WO 94/18299 A1 | 8/1994 |
| WO | 1994019446 A1 | 9/1994 |
| WO | WO 94/24869 A1 | 11/1994 |
| WO | WO 94/29509 A1 | 12/1994 |
| WO | 199502030 A1 | 1/1995 |
| WO | WO 95/02030 A1 | 1/1995 |
| WO | WO 95/21122 A1 | 8/1995 |
| WO | WO 95/21290 A1 | 8/1995 |
| WO | WO 95/28471 A1 | 10/1995 |
| WO | WO 95/28472 A1 | 10/1995 |
| WO | 1995031527 A1 | 11/1995 |
| WO | 1995034269 A1 | 12/1995 |
| WO | WO 95/33816 A1 | 12/1995 |
| WO | 1996010072 A1 | 4/1996 |
| WO | WO 96/14384 A1 | 5/1996 |
| WO | WO 96/16148 A1 | 5/1996 |
| WO | 1996033254 A1 | 10/1996 |
| WO | 1997000938 A1 | 1/1997 |
| WO | 1997032871 A1 | 9/1997 |
| WO | 1997042286 A1 | 11/1997 |
| WO | WO 97/43393 A1 | 11/1997 |
| WO | 1998000528 A1 | 1/1998 |
| WO | 1998003513 A1 | 1/1998 |
| WO | WO 98/03513 A1 | 1/1998 |
| WO | 1998005749 A1 | 2/1998 |
| WO | WO 98/11189 A1 | 3/1998 |
| WO | WO 98/11777 A1 | 3/1998 |
| WO | 1998020116 A1 | 5/1998 |
| WO | WO 98/18893 A1 | 5/1998 |
| WO | 1999019451 A1 | 4/1999 |
| WO | WO 99/31215 A1 | 6/1999 |
| WO | WO 99/32598 A1 | 7/1999 |
| WO | 1999064556 A1 | 12/1999 |
| WO | 2000042158 A1 | 7/2000 |
| WO | WO 00/42145 A1 | 7/2000 |
| WO | WO 00/70951 A1 | 11/2000 |
| WO | WO 00/76963 A1 | 12/2000 |
| WO | WO 00/78911 A1 | 12/2000 |
| WO | WO01/00765 A1 | 1/2001 |
| WO | WO 01/19414 A1 | 3/2001 |
| WO | 200144176 A1 | 6/2001 |
| WO | 200170030 A2 | 9/2001 |
| WO | 0187358 | 11/2001 |
| WO | 2002008076 A1 | 1/2002 |
| WO | WO 03/006581 | 1/2003 |
| WO | 2003050343 A2 | 6/2003 |
| WO | 03067989 A1 | 8/2003 |
| WO | 2003085818 A1 | 10/2003 |
| WO | 2004033269 A2 | 4/2004 |
| WO | WO 2004/044266 | 5/2004 |
| WO | 2005109981 A1 | 11/2005 |
| WO | 2006016145 A1 | 2/2006 |
| WO | 2006094232 A1 | 9/2006 |
| WO | 2006118594 A1 | 11/2006 |
| WO | 2006131503 A2 | 12/2006 |
| WO | 2007008478 A1 | 1/2007 |
| WO | 2007013324 A1 | 2/2007 |
| WO | 2007066302 A1 | 6/2007 |
| WO | WO 2008/005058 | 1/2008 |
| WO | 2009023492 A2 | 2/2009 |
| WO | 2009040769 A1 | 4/2009 |
| WO | 2009053686 A1 | 4/2009 |
| WO | WO 2009/071664 A1 | 6/2009 |
| WO | 2009118714 A2 | 10/2009 |
| WO | 2009141548 A2 | 11/2009 |
| WO | 2010050634 A1 | 5/2010 |
| WO | 2010080274 A2 | 7/2010 |
| WO | 2010090125 A1 | 8/2010 |
| WO | 2011083295 A1 | 7/2011 |
| WO | WO 2011/089313 A2 | 7/2011 |
| WO | 2011146557 | 11/2011 |
| WO | 2011159859 A2 | 12/2011 |
| WO | WO 2012/090124 A2 | 7/2012 |
| WO | 02088076 A2 | 11/2012 |

OTHER PUBLICATIONS

Katz, Jonathan, "Report: Fracking to Grow U.S. Water-Treatment Market Nine-Fold by 2020", http://www.industryweek.com/global-economy/report-fracking-grow-us-frack-water-treatment-market-nine-fold-2020, [retrieved from the internet on Jun. 6, 2012], pp. 1-2.

Chung, L., et al., "Coordinative Binding of Divalent Cations with Ligands Related to Bacterial Spores", Biophysical Journal (1971) vol. 11, pp. 470-482.

Nowack, Bernd, "Environmental Chemistry of Phosphonates", Water Research (2003) vol. 37, No. 11, pp. 2533-2546.

Popov, Konstantin, et al., "Critical Evaluation of Stability Constants of Phosphonic Acids", Pure Appl. Chem. (2001), vol. 73, No. 10, pp. 1641-1677.

Rizkalla, E.N., et al., "Metal Chelates of Phosphonate-Containing Ligands-V Stability of some 1-Hydroxyethane-1, 1-Diphosphonic Acid Metal Chelates", Talanta (1980), vol. 27, No. 9, pp. 715-719.

Swern, Daniel (ed.), "Organic Peroxides", Wiley-Interscience, New York (1970), vol. 1, pp. 360-369.

Ecolab USA Inc., PCT/US2013/063512 filed Oct. 4, 2013, "The International Search Report and Written Opinion", dated Dec. 26, 2013, 10 pages.

A.O.A.C. Use Dilution Methods, Official Methods of Analysis of the Association of Official Analytical Chemists, paragraph 955.14 and applicable sections, 15th Edition, 1990 (EPA Guideline 91-2.

A.O.A.C. Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2.

Brooks, Robert E., et al., "Alkaline hydrogen peroxide bleaching of cellulose", Kluwer Academic Publishers, Cellulose 7: 263-286, 2000 (24 pages).

Carboni-Oerlemans, Chiara, et al., "Hydrolase-catalysed synthesis of peroxycarboxylic acids: Biocatalytic promiscuity for practical applications", Elsevier, Journal of Biotechnology, 126 (2006) 140-151 (12 pages).

Chen, J., "Enhanced Alkaline Peroxide Bleaching of Softwood Kraft Pulps Using a New Activator," Journal of Pulp and Paper Science: vol. 27, No. 12, Dec. 2001 (4 pages).

(56) References Cited

OTHER PUBLICATIONS

Dannacher, Josef J., "Catalytic bleach: Most valuable applications for smart oxidation chemistry", Journal of Molecular Catalysis A: Chemical 251 (2006) 159-176.

Effkemann, Stefan, et al., "Peroxide analysis in laundry detergents using liquid chromotography", Elsevier, Analytica Chimica Acta, 363 (1998) 97-103 (7 pages).

Lee, Jung Jin, et al., "Hydrolytic stability of a series of lactam-based cationic bleach activators and their impact on cellulose peroxide bleaching", Springer Science+Business Medica B.V., Cellulose (2010) 17:671-678 (8 pages).

Leistner (1995) In Gould GW (Ed.) New Methods of Food Preservation, Springer, pp. 1-21.

Leistner, "Basic aspects of food preservation by hurdle technology", International Journal of Food Microbiology, (2000) 55:181-186.

Leveneur, Sebastien, "Synthesis of peroxypropionic acid from propionic acid and hydrogen peroxide over heterogeneous catalysts", Elsevier, Chemical Engineering Journal, 147 (2009) 323-329 (7 pages).

Maeda, Hatsuo, et al., "Assessment of Acyl Groups and Reaction Conditions in the Competition between 6 Perhydrolysis and Hydrolysis of Acyl Resorufins for Developing an Indicator Reaction for Fluorometric Analysis of Hydrogen Peroxide", Pharmaceutical Society of Japan, Cehm. Pharm. Bull. 50(2) 169-174,2002 (6 pages).

Malow and Wehrstedt, "Prediction of the self-accelerating decomposition temperature (SADT) for liquid organic peroxides from differential scanning calorimetry (DSC) measurements", J. Hazard Mater. (2005) 120(1-3):21-4.

Muurinene, Esa, "Organosolv Pulping—A review and distillation study related to peroxyacid pulping", Department of Process Engineering, University of Oulu, May 16, 2000, Oulu, Finland (314 pages).

Ogata, Y., et al., "The Formation of Peracids by the Perhydrolysis With Alkaline Hydrogen Peroxide", Tetrochem, vol. 23, pp. 3327-3332, Pergamom Press, 1967 (7 pages).

Ogata et al., "Radical scavenging activities of niacin-related compounds", Biosci. Biotechnol. Biochem., 2002, 66(3), 641-645.

"Recommendations on the Transport of Dangerous Goods, Manual of Tests and Criteria", 5th revised edition (2009), UN , sect. 28.4.4, p. 314.

"Recommendations on the Transport of Dangerous Goods, Model Regulations" (Rev.17) ST/SG/AC.10/1/Rev.17 (2011).

Rusch gen. Klaas, Mark, et al., "Lipase-catalyzed preparation of peroxy acids and their use for expoxidation", Elsevier, Journal of Molecular Catalysis A: Chemical117 (1997) 311-319 (9 pages).

Rusch gen. Klaas, Market al., "Lipase-catalyzed conversions of trimethylsilyl ethers: deprotection, acetylation, epoxidation and one-pot-multi-step reactions", Journal of Molecular Catalysis B: Enzymatic 7 (1999) 283-289.

Rusch gen. Klaas, Market al., "Biocatalylic peroxy acid formation for disinfection", Journal of Molecular Catalysis B: Enzymatic 19-20 (2002) 499-505.

Suchy, Miro, et al., "Improving Alkaline Peroxide Delignification Using a Vandium Activator", Papriran and Department of Chemistry, McGill University, Montreal, Quebec, Oct. 25-29, 1998 (15 pages).

Tsunokawa, Youko et al., "A Versatile Method for Preparation of 0-Aikylperoxycarbonic Acids: Epoxidation with Alkyloxycarbonylimidazoles and Hydrogen Peroxide", Tetrahedron Letters, vol. 23, No. 20, (1982), pp. 2113-2116.

Yin, De Lu (Tyler), et al., "Switching Catalysis from Hydrolysis to Perhydrolysis in Pseudomonas fluorescens Esterase", Biochemistry, (2010) 49:1931-1942.

ECOLA8 USA, Inc. et al., PCT/IB2011/055832 filed Dec. 20, 2011, "Notification of Transmittal of the International Search Report and the Written Opinion of the International Searching Authority, or the Declaration" dated Aug. 14, 2012, 14 pages.

ECOLA8 USA, Inc. et al., PCT/IB2011/055830 filed Dec. 20, 2011, "Notification of Transmittal of the International Search Report and the Written Opinion of the International Searching Authority, or the Declaration" dated Aug. 24, 2012, 8 pages.

U.S. Appl. No. 13/645,671 (2012).

Li, Junzhong, "Stable Percarboxylic Acid Compositions and Uses Thereof", Filed Mar. 15, 2013, U.S. Appl. No. 13/844,515.

Ecolab USA Inc., PCT/US2013/030904, filed on Mar. 13, 2013, "The International Search Report and the Written Opinion of the International Searching Authority, or the Declaration", dated Jul. 5, 2013.

CN 1751768—San Nopco—English Translation.

DE 197 54 290 A1—Henkel KGaA—English Translation.

EP 0 061 393—Elf Atochem—English Abstract.

EP 0 280 697—Garcin Francoise—English Translation.

EP 0 395 902—Schulke & Mayr Gmbh—English Translation.

EP 0 626 371—Degussa—English Translation.

EP 2 271 410—Arkema—English Translation.

JP 2006-45147—Kao Corp—English Translation.

JP 2006-45146—Kao Corp—English Translation.

Junzhong Li et al., "Stable Percarboxylic Acid Compositions and Uses Thereof", U.S. Appl. No. 13/844,515, filed Mar. 15, 2013, Applicant Ecolab USA Inc.

United States Patent and Trademark Office, "Office Action", issued in connection with U.S. Appl. No. 13/844,515, 11 pages, dated Dec. 5, 2014.

IP Australia, "Patent Examination Report No. 1," issued in connection with Australian Patent Application No. 2012201802, dated Mar. 5, 2013, 3 pages.

IP Australia, "Patent Examination Report No. 2," issued in connection with Australian Patent Application No. 2012201804, dated Jul. 1, 2013, 3 pages.

IP Australia, "Patent Examination Report No. 1," issued in connection with Australian Patent Application No. 2012201804, dated Feb. 27, 2013, 3 pages.

IP Australia, "Patent Examination Report No. 2," issued in connection with Australian Patent Application No. 2009230713, dated Jul. 1, 2013, 3 pages.

IP Australia, "Patent Examination Report No. 1," issued in connection with Australian Patent Application No. 2009230713, dated Feb. 22, 2013, 3 pages.

IP Australia, "Patent Examination Report No. 2," issued in connection with Australian Patent Application No. 2012201800, dated Jul. 3, 2013, 3 pages.

IP Australia, "Patent Examination Report No. 1," issued in connection with Australian Patent Application No. 2012201800, dated Feb. 27, 2013, 3 pages.

State Intellectual Property Office of China, "First Office Action," issued in connection with Chinese Application No. 201380014182.1, dated Jun. 18, 2015, 26 pages.

European Patent Office, "Partial Supplementary European Search Report" issued in connection with application PCT/US2013/030904, dated Nov. 13, 2015.

State Intellectual Property Office of the People's Republic of China, "First Office Action" issued in connection with Chinese Application No. 201380051957.2, dated Nov. 24, 2015.

European Patent Office, "Extended European Search Report" issued in connection with application PCT/US2013/030904, dated Jan. 3, 2016.

Ecolab USA Inc., PCT/US2013/030904, "International Search Report and Written Opinion of the International Searching Authority," 14 pages, dated Jul. 5, 2013.

Database CAPLUS Chemical Abstracts Service, Accession No. 1960:97225, abstract of DE 1024514, "Oxidation of Organic Compounds with Hydrogen Peroxide in the Liquid Base," Feb. 20, 1958.

Ecolab USA Inc., Supplementary European Search Report for EP 13844411.2, 7 pages, dated Jan. 19, 2016.

Ecolab USA Inc., Supplementary European Search Report for EP 15184379.4, 7 pages, dated Jan. 19, 2016.

United States Patent and Trademark Office, "Non-Final Office Action," issued in commention to U.S. Appl. No. 13/785,405, dated Oct. 22, 2013.

Australian Govenment, IP Australia, "Examination Report No. 1 for Standard Patent Application," in connection to Application No. 2014226466 of Ecolab USA Inc., 5 pages, dated Apr. 12, 2017.

(56) References Cited

OTHER PUBLICATIONS

Korean Intellectual Property Office, "The International Search Report and Written Opinion of the International Searching Authority," issued in connection to PCT/US2014/017283, dated Apr. 28, 2014.

The State Intellectual Property Office of the People's Republic of China,"Seach Report", issued in connection with Application No. 201480011644.9, dated 00 Jan 2000.

IP Australia, "Patent Examination Report No. 1," issued in connection with AU Application Serial No. 2013326904, 5 pages, dated Jul. 4, 2017.

Godemeyer Blum Lenze Patentanälte,"Reply to Examination Report," filed online in connection to EP Application No. 13844411.2, 21 pages, May 31, 2017.

Godemeyer Blum Lenze Patentanälte, "Reply to Examination Report," filed online in connection to EP Application No. 15184379.4, 25 pages, May 31, 2017.

\* cited by examiner

USE OF PERACETIC ACID/HYDROGEN PEROXIDE AND PEROXIDE-REDUCING AGENTS FOR TREATMENT OF DRILLING FLUIDS, FRAC FLUIDS, FLOWBACK WATER AND DISPOSAL WATER

CROSS-REFERENCE TO RELATED APPLICATIONS

This application is a continuation-in-part application of U.S. Provisional Application No. 61/617,814, filed Mar. 30, 2012, titled "Use of Peracetic Acid/Hydrogen Peroxide and Catalase for Treatment of Drilling Fluids, Frac Fluids, Flowback Water and Disposal Water," which is herein incorporated by reference in its entirety.

This application is also related to U.S. patent application Ser. No. 13/798,311, entitled "Use Of Peracetic Acid/Hydrogen Peroxide and Peroxide-Reducing Enzymes for Treatment of Drilling Fluids, Frac Fluids, Flow back Water and Disposal Water," U.S. patent application Ser. No. 13/798, 307, now issued U.S. Pat. No. 9,242,879, entitled "Use Of Peracetic Acid/Hydrogen Peroxide And Peroxide-Reducing Agents For Treatment Of Drilling Fluids, Frac Fluids, Flow back Water And Disposal Water," and U.S. Patent Application Ser. No. 61/710,631, filed Oct. 5, 2012, and titled "Stable Peroxycarboxylic Acid Compositions and Uses Thereof," each of which are filed concurrently herewith. The entire contents of these patent applications are hereby expressly incorporated herein by reference including, without limitation, the specification, claims, and abstract, as well as any figures, tables, or drawings thereof.

FIELD OF THE INVENTION

The present disclosure relates to percarboxylic acid compositions and methods for the use of peracid compositions with decreased hydrogen peroxide concentrations for various water treatments, including oil- and gas-field operations, and/or other aseptic treatments. The present invention also relates to slick water compositions and gel based compositions that comprise stable percarboxylic acid compositions and the use thereof in oil- and gas-field operations. In numerous aspects, peracetic acid is the preferred peracid and is treated with a peroxide-reducing agent, such as a metal or strong oxidizer, to substantially reduce the hydrogen peroxide content. The methods of treatment are particularly suitable for treatment of drilling fluids, frac fluids, flow back waters and/or disposal waters for improving water condition, reducing oxidizing damage associated with hydrogen peroxide and/or reducing bacteria infestation.

BACKGROUND OF THE INVENTION

Peroxycarboxylic acids (also referred to as peracids), as well as mixed peroxycarboxylic acid systems, are known for use as antimicrobials and bleaching agents in a variety of industries. Peracetic acid or peroxyacetic acid (PAA or POAA) (dynamic equilibrium mixture of POAA/PAA, $H_2O_2$, $H_2O$ and AA) have been used in the food and beverage industries as a fast acting, "green" antimicrobial. Such products demonstrate beneficial properties towards oxidizing solids and improving water quality. In addition, compared to other commercially available biocides, the use of peracetic acid results in a low environmental footprint due in part to its decomposition into innocuous components (e.g. acetic acid (AA), oxygen, $CO_2$ and $H_2O$). See for example, U.S. Pat. No. 8,226,939, entitled "Antimicrobial Peracid Compositions with Selected Catalase Enzymes and Methods of Use in Aseptic Packaging," which is incorporated by reference in its entirety.

Peracids have also been used for certain water treatment applications. However, these have been very limited in the area of commercial well drilling operations. See for example U.S. Patent Publication No. 2010/0160449, entitled "Peracetic Acid Oil-Field Biocide and Method," and U.S. Pat. No. 7,156,178 which are incorporated by reference in their entirety. However, particular water treatment applications present difficulties for the use of peracids during several steps of the oil and gas production methods, including for example microbial efficacy and compatibility concerns. For example, despite its fast action and eco-friendly properties, the use of peracids, including peracetic acid, has a number of limitations for use in water treatment methods. High dosages of the peracid can increase the corrosion rates in pipelines and equipment due in part to the presence of hydrogen peroxide ($H_2O_2$). Moreover, the peracids/$H_2O_2$ can interfere with the activity of functional agents necessary for the methods of water treatment in oil and gas recovery, including friction reducers and thickeners which are often critical for the fracking process. In addition, peracids and hydrogen peroxide are prone to quenching from common, naturally occurring chemicals which can severely limit their utility.

There remains a need for enhanced water treatment methods. For example, from a microbiology perspective, mitigation of microorganisms is essential to minimize environmental concerns for waste products and to avoid contamination of systems, such as well or reservoir souring and/or microbiologically-influenced corrosion (MIC). As a result, prior to the drilling and fracking steps, water is treated to restrict the introduction of microbes into the well or reservoir. This also acts to prevent microbes from having a negative effect on the integrity of the fluids. In addition, before disposal, flow-back water is treated to abide environmental restrictions stipulated by regulatory agencies.

Accordingly, it is an objective of the invention to replace conventional oxidizing biocides for water treatments, such as typical equilibrium peracetic acid, hypochlorite or hypochlorous acid, and/or chlorine dioxide compositions.

It is a further objective of the invention to develop methods for water treatment in oil and gas recovery that provide effective antimicrobial efficacy without any deleterious interaction with functional agents, including for example friction reducers and viscosity enhancers.

A further objective of the invention is to develop compositions and methods for use of atypical peracids via distillation, perhydrolysis of acetyl donors, and preferably use of peroxide-reducing agents, such as a metal or strong oxidizer, to improve the stability of peracids and peracid compositions and in most cases the antimicrobial efficacy of the peracid compared to the use of conventional equilibrium peracids alone.

A further objective of the invention is to develop methods using peracids for the treatment of water used in drilling and/or fracking, as well as treatment of water that is planned for disposal to result in cleaner water with low numbers of microorganisms.

A still further objective of the invention are compositions and methods for using peracids, namely peracetic acid, with a peroxide-reducing agent, such as a metal or strong oxidizer, to reduce $H_2O_2$ in order to minimize the negative effects of $H_2O_2$.

Other objects, advantages and features of the present invention will become apparent from the following specification taken in conjunction with the accompanying drawings.

BRIEF SUMMARY OF THE INVENTION

In an aspect, the present invention provides a method of treating waters comprising: (a) treating a percarboxylic acid composition with a peroxide-reducing agent to generate an antimicrobial composition; (b) providing the antimicrobial composition to a water source in need of treatment to form a treated water source, wherein the treated water source comprises (i) from up to about 1000 ppm inorganic peroxide-reducing agent, (ii) from about 0 wt-% to about 1 wt-% hydrogen peroxide; (iii) from about 0.0001 wt-% to about 10.0 wt-% of a C1-C22 carboxylic acid; and (iv) from about 0.0001 wt-% to about 10.0 wt-% of a C1-C22 percarboxylic acid, wherein the hydrogen peroxide to peracid ratio is from about 0:100 to about 1:10 by wt; and (c) directing the treated water source into a subterranean environment or disposing of the treated water source having a minimized environmental impact.

In a further aspect, the present invention provides a method of treating a water source comprising: adding a percarboxylic acid and peroxide-reducing agent to the water source to form a treated water source having a hydrogen peroxide to peracid ratio from about 0:100 to about 1:10 by weight, wherein said antimicrobial composition in a use solution with said treated water source comprises (i) less than about 1000 ppm of an inorganic peroxide-reducing agent, (ii) from about 0 wt-% to about 1 wt-% hydrogen peroxide; (iii) from about 0.0001 wt-% to about 10.0 wt-% of a $C_1$-$C_{22}$ carboxylic acid; and (iv) from about 0.0001 wt-% to about 10.0 wt-% of a $C_1$-$C_{22}$ percarboxylic acid. In a further aspect, the treated water source reduces corrosion caused by hydrogen peroxide and reduces microbial-induced corrosion, and wherein the antimicrobial composition does not interfere with friction reducers, viscosity enhancers, other functional ingredients found in the water source or combinations thereof.

Surprisingly, it has been found that peroxide-reducing agents, such as a metal or strong oxidizer, are particularly effective at decomposing hydrogen peroxide in peracid compositions and in particular in peracid compositions that are used in water treatments for oil and gas recovery. Methods and compositions for using decreased amounts/ratio of hydrogen peroxide (to peracid) provide unexpected benefits in the stability (and as an apparent result, further unexpected benefits in the efficacy) of the oxidizing biocides. In turn the reduced available oxygen within the peracid composition does not negatively interact with functional agents, including for example friction reducers, and provides a number of additional benefits for use in industrial applications and/or various aseptic treatment applications.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
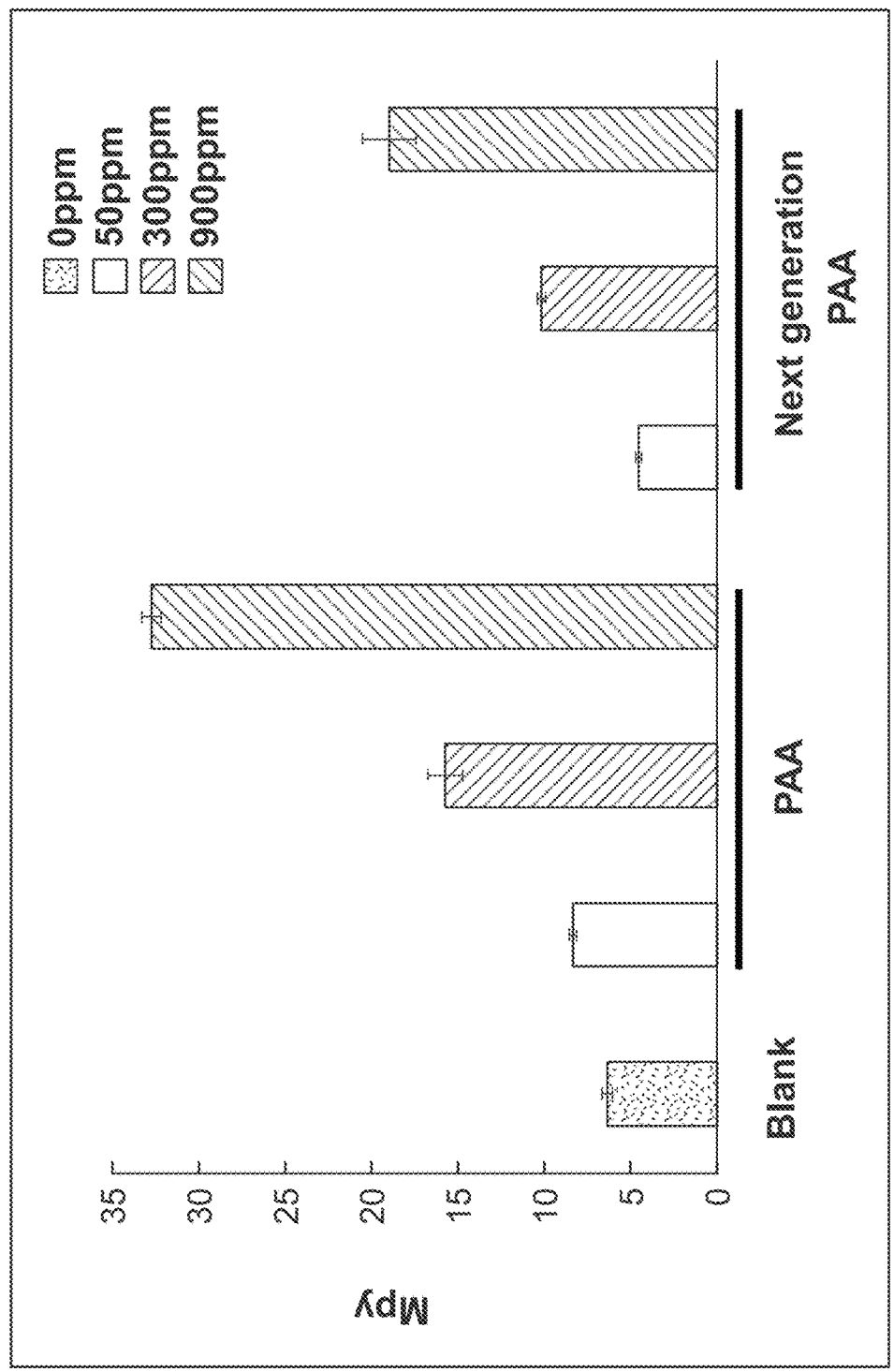
FIGS. 1-2 show an embodiment of the invention where use of peracid with catalase decreases the corrosion rates of carbon steel.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The present disclosure relates to peracid compositions with low to substantially no hydrogen peroxide for use in water treatments. In particular, peroxycarboxylic acids treated with a peroxide-reducing agent, such as a metal or strong oxidizer, to reduce and/or eliminate hydrogen peroxide from the peroxycarboxylic acid are provided, as well as methods for treating various water sources with the same for the use in oil and gas recovery.

The methods and compositions disclosed herein have many advantages over conventional, peracid compositions used for water treatment and/or other antimicrobial treatments. For example, the peracid compositions treated with a peroxide-reducing agent (or other means to substantially reduce hydrogen peroxide content) according to methods disclosed herein, have significantly lower levels of the oxidant hydrogen peroxide. Beneficially, the reduction and/or elimination of hydrogen peroxide compared to un-treated peracid compositions provides improved antimicrobial efficacy, eliminates deleterious interaction with friction reducers and other functional ingredients used in water treatments, and/or reduces the environmental impact of treated waters when eliminated. In addition, the treated peracid compositions have greatly reduced off gassing potential and continue to prevent well and reservoir souring as well as prevent microbiologically-influenced corrosion. These and other benefits of the present invention are disclosed herein.

The embodiments of this invention are not limited to particular peroxycarboxylic acid compositions (preferably treated with a peroxide-reducing agent, such as a metal or strong oxidizer to reduce hydrogen peroxide) and methods for using the same, which can vary and are understood by skilled artisans. It is further to be understood that all terminology used herein is for the purpose of describing particular embodiments only, and is not intended to be limiting in any manner or scope. For example, all units, prefixes, and symbols may be denoted in its SI accepted form. Numeric ranges recited within the specification are inclusive of the numbers defining the range and include each integer within the defined range.

It should be noted that, as used in this specification and the appended claims, the singular forms "a," "an," and "the" include plural referents unless the content clearly dictates otherwise. Thus, for example, reference to a composition containing "a compound" includes a composition having two or more compounds. It should also be noted that the term "or" is generally employed in its sense including "and/or" unless the content clearly dictates otherwise.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "cleaning," as used herein, means to perform or aid in soil removal, bleaching, microbial population reduction, or combination thereof. For the purpose of this patent application, successful microbial reduction is achieved when the microbial populations are reduced by at least about 50%, or by significantly more than is achieved by a wash with water. Larger reductions in microbial population provide greater levels of protection.

As used herein, "consisting essentially of" means that the methods and compositions may include additional steps, components, ingredients or the like, but only if the additional steps, components and/or ingredients do not materially alter the basic and novel characteristics of the claimed methods and compositions. It is understood that aspects and embodiments of the invention described herein include "consisting" and/or "consisting essentially of" aspects and embodiments.

As used herein, the term "disinfectant" refers to an agent that kills all vegetative cells including most recognized pathogenic microorganisms, using the procedure described in A.O.A.C. Use Dilution Methods, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the term "free," "no," "substantially no" or "substantially free" refers to a composition, mixture, or ingredient that does not contain a particular compound or to which a particular compound or a particular compound-containing compound has not been added. According to the invention, the reduction and/or elimination of hydrogen peroxide according to embodiments provide hydrogen peroxide-free or substantially-free compositions. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-%.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition As used herein, the term "water" for treatment according to the invention includes a variety of sources, such as freshwater, pond water, sea waters, salt water or brine source, brackish water, recycled water, or the like. Waters are also understood to optionally include both fresh and recycled water sources (e.g. "produced waters"), as well as any combination of waters for treatment according to the invention.

As used herein, "weight percent," "wt-%," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt-%," etc.

EMBODIMENTS OF THE INVENTION

The invention generally relates to the use of peroxide-reducing agents, such as a metal or strong oxidizer, for use with peracid compositions. The invention uses the peroxide-reducing agents with peracid compositions for use in water treatments in the field of oil and gas recovery. The invention further relates to the use of additional methods to reduce and/or eliminate hydrogen peroxide from peracids to provide similar benefits to a peracid composition. Additional methods which produce a very low hydrogen peroxide to peracid ratio are similarly advantageous and suitable for use according to the invention, including those disclosed in U.S. Provisional Patent Application Ser. No. 61/710,631, filed Oct. 5, 2012, and entitled "Stable Peroxycarboxylic Acid Compositions and Uses Thereof," and the conversion application Ser. No. 13/839,806, now issued U.S. Pat. No. 9,267,236, which are herein incorporated by reference in their entirety. These may include, for example, equilibrium peracid compositions distilled to recover a very low hydrogen peroxide peracid mixture, other catalysts for hydrogen peroxide decomposition (e.g. biomimetic complexes) and/or the use of perhydrolysis of peracid precursors, such as esters (e.g triacetin) and amides with alkyl leaving groups ranging in carbon chain lengths of C1-C8, to obtain peracids with very low hydrogen peroxide.

Compositions

The compositions of the invention may comprise, consist of and/or consist essentially of a peracid composition having a low hydrogen peroxide to peracid ratio. In an aspect, the peracid composition has a hydrogen peroxide to peracid ratio in a concentrated composition from about 0:100 to about 1:10, preferably from about 0.5:100 to about 1:100, and more preferably from about 1:100 to 1:10. The compositions of the invention may comprise, consist of and/or consist essentially of a peracid composition and a peroxide-reducing agent used to obtain a resultant peracid composition having a low hydrogen peroxide to peracid ratio. In equilibrium chemistries there is a dynamic equilibrium between peracids, respective carboxylic acids, hydrogen peroxide and water in a composition. For example, a peracetic acid composition further includes acetic acid, hydrogen peroxide and water in the aqueous commercial formulation. Accordingly, the compositions of the invention may further comprise, consist of and/or consist essentially of a peracid composition, carboxylic acid, hydrogen peroxide, and a peroxide-reducing agent. In other aspects, additional functional ingredients, such as a friction reducer, corrosion inhibitor, viscosity enhancer and/or additional antimicrobial agent are employed in the compositions. In other aspects, no additional functional ingredients are employed in the compositions.

Peroxide-Reducing Agents

In an aspect of the invention, a peroxide-reducing agent is used to reduce and/or eliminate the concentration of hydrogen peroxide in an antimicrobial peracid composition. In some aspects, the peroxide-reducing agent is a peroxide-reducing inorganic agent. In an aspect of the invention, the agent is a metal and/or a strong oxidizing agent. The metal catalyzes the decomposition of hydrogen peroxide to water and oxygen. Further, the metal catalyzes the decomposition of the peracid in equilibrium. Without being limited to a particular mechanism of the invention, the decomposition of the hydrogen peroxide and peracid of an equilibrium peracid composition catalyzed by the peroxide-reducing agent beneficially results in an accelerated oxidation reaction causing increased or enhanced antimicrobial efficacy.

Beneficially, the reduction and/or elimination of hydrogen peroxide (e.g. an oxidizer) further results in other additives for a water treatment source (e.g. water source) not being degraded or rendered incompatible. This is critical as various additives used to enhance and/or modify the characteristics of aqueous fluids used in well drilling, recovery and/or production applications are at risk of degradation by the oxidizing effects of hydrogen peroxide. These may include for example, friction reducers, scale inhibitors and viscosity enhancers used in commercial well drilling, well completion and stimulation, or production applications. According to an aspect of the invention, the significant reduction in hydrogen peroxide from a peracid composition reduces or eliminates these compatibility and/or degradation concerns.

In an aspect, the peroxide-reducing agent is a metal, combination of metals and/or a metal compound. Examples of suitable metals for use as the peroxide-reducing agents (e.g. decomposition agents) include heavy metals. In a further aspect, metal oxides may be employed according to the invention. For example, suitable metals include platinum, palladium, bismuth, tin, copper, manganese, iron, tungsten, zirconium, ruthenium, cobalt, molybdenum, nickel, iron, copper and/or manganese. In a preferred aspect, the metals include platinum, tungsten, zirconium, ruthenium, cobalt, molybdenum, nickel, iron, copper and/or manganese. In a further preferred aspect of use in field operations for well drilling, recovery and/or production applications, the metals include iron, copper and/or manganese. In further aspects of the invention, a combination of metals can be employed as the peroxide-reducing agent.

In an aspect, the peroxide-reducing agent is a strong oxidizer. Without being limited to a particular mechanism of action of the compositions and/or methods of the invention, the oxidizer has greater oxidizing potential that hydrogen peroxide, beneficially allowing the decomposition of the oxidant hydrogen peroxide. Examples of suitable strong oxidizers for use as peroxide-reducing agents include halide anions, halide salts and/or halide sources, including for example bromide and/or bromine, iodide and/or iodine, chloride and/or chlorine, fluoride and/or fluorine, etc. In a particular aspect, the peroxide-reducing agent is a chlorine sources, including, for example, hypochlorite or sodium hypochlorite, chlorine dioxide, or the like.

In a further aspect of the invention, the agent is not UV-sensitive. In a further aspect of the invention, the metals and/or strong oxidizing agents have a high ability to decompose hydrogen peroxide. In some aspects, the peroxide-reducing agents are able to degrade at least about 500 ppm of hydrogen peroxide in a peracid composition in 15 minutes. In other aspects, the metals and/or strong oxidizing agents also have a high ability to decompose hydrogen peroxide at low concentrations. In some embodiments, the concentration of metals and/or strong oxidizing agents needed to degrade 500 ppm of hydrogen peroxide in a peracid composition in 15 minutes is less than 200 ppm, less than 100 ppm, and less than 50 ppm.

Beneficially, the reduction or elimination of hydrogen peroxide from oxidizing compositions obviate the various detriments caused by oxidizing agents in the various field operations for well drilling, recovery and/or production applications (and others set forth according to the methods of the invention). In particular, the use of the peroxide-reducing agents) with the peracid compositions provides enhanced antimicrobial benefits without causing the damage associated with conventional oxidizing agents (e.g. peracetic acid, hypochlorite or hypochlorous acid, and/or chlorine dioxide), such as corrosion. In a further aspect, the reduction of hydrogen peroxide also benefits the stability of gel formation in gel frac fluids. Without being limited to a mechanism of the invention, the reduction of hydrogen peroxide in a peracid composition beneficially allows a gel frac fluid to maintain the gel for a sufficient period of time (before it breaks apart within the subterranean environment). In some aspects, the reduction of the hydrogen peroxide within a peracid composition according to the invention provides a suitable level of peroxide from about 1 ppm to about 50 ppm, from about 1 ppm to about 25 ppm, or preferably from about 5 ppm to about 15 ppm to maintain a stable gel frac fluid for an extended period of time.

In an aspect, the peroxide-reducing agents preferentially decompose hydrogen peroxide from a peracid composition (e.g. a greater percentage of peracid concentration remains in a treated peracid composition in comparison to hydrogen peroxide). Without limiting the scope of peroxide-reducing agents suitable for use according to the invention, in an aspect the agent preferentially reduces hydrogen peroxide over the peracid. In a further aspect, the agent reduces at least about 2:1 hydrogen peroxide to peracid, or greater. In a further aspect, the agent reduces at least about 1.5:1 hydrogen peroxide to peracid, or greater.

In some embodiments, the peroxide-reducing agent is able to degrade at least about 50% of the initial concentration of hydrogen peroxide in a peracid composition. Preferably, the agent is provided in sufficient amount to reduce the hydrogen peroxide concentration of a peracid composition by at least more than about 50%, more preferably at least about 60%, at least about 70%, at least about 80%, or at least about 90%. In some embodiments, the peroxide-reducing agent reduces the hydrogen peroxide concentration of a peracid composition by more than about 90%. Without limiting the scope of invention, the numeric ranges are inclusive of the numbers defining the range and include each integer within the defined range.

In an aspect of the invention, the peroxide-reducing agents are suitable for use and have a tolerance to a wide range of temperatures, including the temperatures ranges in water treatment applications which may range from about 0-180° C. Although temperature and other ambient conditions may affect the stability of the agents, a suitable peroxide-reducing agent will maintain at least 50% of its activity under such storage and/or application temperatures for at least about 10 minutes, preferably for at least about 1 hour, and more preferably for at least about 24 hours. Without limiting the scope of invention, the numeric ranges are inclusive of the numbers defining the range and include each integer within the defined range.

In a further aspect of the invention, the peroxide-reducing agents described herein have a tolerance to pH ranges found in water treatment applications. Acetic acid levels (or other carboxylic acid) in a water treatment application can widely range in parts per million (ppm) of acetic or other carboxylic acid. The solutions will have a corresponding range of pH range from greater than 0 to about 10. A suitable peroxide-reducing agent will maintain at least about 50% of its activity in such solutions of acetic or other carboxylic acid over a period of about 10 minutes, preferably for at least about 1 hour, and more preferably for at least about 24 hours. Without limiting the scope of invention, the numeric ranges are inclusive of the numbers defining the range and include each integer within the defined range.

In an aspect of the invention, a peroxide-reducing agent is present in a use solution of the water treatment and peracid composition in sufficient amounts to reduce the concentration of hydrogen peroxide from the peracid composition within at least a few hours, preferably within less than 10 hours, preferably within less than 5 hours, preferably within less than 4 hours, and still more preferably within less than 1 hour. In an aspect of the invention, a peroxide-reducing agent is present in a use solution of the water treatment and peracid composition in sufficient amounts to reduce the concentration of hydrogen peroxide from the peracid composition by at least 50% within about 10 minutes, preferably within about 5 minutes, preferably within about 2 to 5 minutes, more preferably within about 1 minute. The ranges of concentration of the agents will vary depending upon the amount of time within which 50% of the hydrogen peroxide from the peracid composition is removed.

In certain aspects of the invention, a peroxide-reducing agent is present in a use solution composition including the water source to be treated in amounts of at least about 0.5 ppm, preferably between about 0.5 ppm and about 1000 ppm, preferably between about 0.5 ppm and about 500 ppm, preferably between about 0.5 ppm and 100 ppm, and more preferably between about 1 ppm and about 100 ppm. Without limiting the scope of invention, the numeric ranges are inclusive of the numbers defining the range and include each integer within the defined range.

The peroxide-reducing agents employed may be free floating in the use solution composition, meaning that the agent is part of the composition, without being bound to a surface.

Alternatively, the peroxide-reducing agents may be immobilized on a surface that is in fluid communication with the use solution composition in way that allows the agent to interact with and decompose hydrogen peroxide from the peracid compositions. In some aspects, immobilized agents may be more stable than unbound, soluble agents. In some aspects, immobilized agents may also have increased thermal and pH stability which might be due to the protection of the substrate provides against sudden thermal and pH changes. An immobilized agent also has the advantage of being able to be removed from the rest of the composition easily. An immobilized agent may include an agent attached to a substrate. Examples of substrates may include for example zeolites, polyurethane foams, polyacrylamide gels, polyethylene maleic anhydride gels, polystyrene maleic anhydride gels, cellulose, nitrocellulose, silastic resins, porous glass, macroporous glass membranes, glass beads, activated clay, zeolites, alumina, silica, silicate and other inorganic and organic substrates. The peroxide-reducing agent may be attached to the substrate in various ways including carrier covalent binding, crosslinking, physical adsorption, ionic binding, and entrapping.

In an aspect, the peroxide-reducing agent is added into a peracid use solution instead of a concentrated peracid composition. Without being limited to a mechanism of action, the use of a peroxide-reducing agent is preferably added to a non-concentrated peracid composition in order to maintain the viability and peroxide-reducing capability of the agent. For example, in an aspect, a concentrated peracid composition (e.g. about 10 wt-% or greater peracid, or about 15 wt-% or greater peracid) is diluted into a water source and thereafter the peroxide-reducing agent is added. In an aspect, the dilute water source may be the water source in need of treatment according to the invention. In another aspect, the dilute water source may be a use solution of the peracid composition (or less concentrated peracid composition) for subsequent dosing into the water source in need of treatment according to the invention.

Peroxide-Reducing Enzymes

In some aspects, the peroxide-reducing agent is a peroxide-reducing enzyme. In an aspect of the invention, a catalase or peroxidase enzyme is used to reduce and/or eliminate the concentration of hydrogen peroxide in an antimicrobial peracid composition. The enzymes catalyze the decomposition of hydrogen peroxide to water and oxygen. Beneficially, the reduction and/or elimination of hydrogen peroxide (strong oxidizer) results in other additives for a water treatment source (e.g. water source) not being degraded or rendered incompatible. Various additives used to enhance or modify the characteristics of the aqueous fluids used in well drilling, recovery and production applications are at risk of degradation by the oxidizing effects of hydrogen peroxide. These may include for example, friction reducers, scale inhibitors and viscosity enhancers used in commercial well drilling, well completion and stimulation, or production applications.

Various sources of catalase enzymes (or other peroxide-reducing enzyme agents) may be employed according to the invention, including: animal sources such as bovine catalase isolated from beef livers; fungal catalases isolated from fungi including *Penicillium chrysogenum*, *Penicillium notatum*, and *Aspergillus niger*; plant sources; bacterial sources such as *Staphylcoccus aureus*, and genetic variations and modifications thereof. In an aspect of the invention, fungal catalases are utilized to reduce the hydrogen peroxide content of a peracid composition.

Catalases (or other peroxide-reducing enzyme agents) are commercially available in various forms, including liquid and spray dried forms. Commercially available catalase includes both the active enzyme as well as additional ingredients to enhance the stability of the enzyme. Some exemplary commercially available catalase enzymes include Genencor CA-100 and CA-400, as well as Mitsubishi Gas and Chemical (MGC) ASC super G and ASC super 200. Additional description of suitable catalase enzymes are disclosed and herein incorporated by reference in its entirety from U.S. Patent Publication No. 2012/0321510 and U.S. Pat. Nos. 8,241,624, 8,231,917 and 8,226,939, which are herein incorporated by reference in their entirety.

In an aspect of the invention, catalase enzymes (or other peroxide-reducing enzyme agents) have a high ability to decompose hydrogen peroxide. In some aspects, catalase enzymes (or other peroxide-reducing enzyme agents) used in this invention include enzymes with a high ability to decompose hydrogen peroxide. In some embodiments, the enzyme is able to degrade at least about 500 ppm of hydrogen peroxide in a peracid composition in 15 minutes. In other aspects, enzymes used in this invention include catalase enzymes (or other peroxide-reducing enzyme agents) with a high ability to decompose hydrogen peroxide at low concentrations. In some embodiments, the concentration of enzyme needed to degrade 500 ppm of hydrogen peroxide in a peracid composition in 15 minutes is less than 200 ppm, less than 100 ppm, and less than 50 ppm.

Beneficially, the reduction or elimination of hydrogen peroxide from oxidizing compositions obviates the various detriments caused by oxidizing agents. In particular, the use of catalase (or other peroxide-reducing enzyme agents) with the peracids compositions provides enhanced antimicrobial benefits without causing the damage associated with conventional oxidizing agents (e.g. peracetic acid, hypochlorite or hypochlorous acid, and/or chlorine dioxide), such as corrosion.

Peroxidase enzymes (or other peroxide-reducing enzyme agents) may also be employed to decompose hydrogen peroxide from a peracid composition. Although peroxidase enzymes primarily function to enable oxidation of substrates by hydrogen peroxide, they are also suitable for effectively lowering hydrogen peroxide to peracid ratios in compositions. Various sources of peroxidase enzymes (or other peroxide-reducing enzyme agents) may be employed according to the invention, including for example animal sources, fungal peroxidases, and genetic variations and modifications thereof. Peroxidases are commercially available in various forms, including liquid and spray dried forms. Commercially available peroxidases include both the active enzyme as well as additional ingredients to enhance the stability of the enzyme.

In some embodiments, the peroxide-reducing enzyme is able to degrade at least about 50% of the initial concentration of hydrogen peroxide in a peracid composition. Preferably, the enzyme is provided in sufficient amount to reduce the hydrogen peroxide concentration of a peracid composition by at least more than about 50%, more preferably at least about 60%, at least about 70%, at least about 80%, at least about 90%. In some embodiments, the enzyme reduces the hydrogen peroxide concentration of a peracid composition by more than 90%. Without limiting the scope of invention, the numeric ranges are inclusive of the numbers defining the range and include each integer within the defined range.

In an aspect of the invention, the peroxide-reducing enzymes are suitable for use and have a tolerance to a wide range of temperatures, including the temperatures ranges in water treatment applications which may range from about 0-180° C. Although temperature and other ambient conditions may affect the stability of the enzymes, a suitable peroxide-reducing enzyme will maintain at least 50% of its activity under such storage and/or application temperatures for at least about 10 minutes, preferably for at least about 1 hour, and more preferably for at least about 24 hours. Without limiting the scope of invention, the numeric ranges are inclusive of the numbers defining the range and include each integer within the defined range.

In a further aspect of the invention, the peroxide-reducing enzymes described herein have a tolerance to pH ranges found in water treatment applications. Acetic acid levels (or other carboxylic acid) in a water treatment application can widely range in parts per million (ppm) of acetic or other carboxylic acid. The solutions will have a corresponding range of pH range from greater than 0 to about 10. A suitable peroxide-reducing enzyme will maintain at least about 50% of its activity in such solutions of acetic or other carboxylic acid over a period of about 10 minutes, preferably for at least about 1 hour, and more preferably for at least about 24 hours. Without limiting the scope of invention, the numeric ranges are inclusive of the numbers defining the range and include each integer within the defined range.

In an aspect of the invention, a peroxide-reducing enzyme is present in a use solution of the water treatment and peracid composition in sufficient amounts to reduce the concentration of hydrogen peroxide from the peracid composition to sufficiently reduced or eliminated concentration within at least a few hours, preferably within less than 10 hours, preferably within less than 5 hours, preferably within less than 4 hours, and still more preferably within less than 1 hour. In an aspect of the invention, a peroxide-reducing enzyme is present in a use solution of the water treatment and peracid composition in sufficient amounts to reduce the concentration of hydrogen peroxide from the peracid composition by at least 50% within about 10 minutes, preferably within about 5 minutes, preferably within about 2 to 5 minutes, more preferably within about 1 minute. The ranges of concentration of the enzymes will vary depending upon the amount of time within which 50% of the hydrogen peroxide from the peracid composition is removed.

In certain aspects of the invention, a peroxide-reducing enzyme is present in a use solution composition including the water source to be treated in amounts of at least about 0.5 ppm, preferably between about 0.5 ppm and about 1000 ppm, preferably between about 0.5 ppm and about 500 ppm, preferably between about 0.5 ppm and 100 ppm, and more preferably between about 1 ppm and about 100 ppm. Without limiting the scope of invention, the numeric ranges are inclusive of the numbers defining the range and include each integer within the defined range.

The enzymes employed may be free floating in the use solution composition, meaning that the enzyme is part of the composition, without being bound to a surface.

Alternatively, the enzymes may be immobilized on a surface that is in fluid communication with the use solution composition in way that allows the enzyme to interact with and decompose hydrogen peroxide from the peracid compositions. Immobilized enzyme may be more stable than unbound, soluble enzyme. Immobilized enzyme also shows increased thermal and pH stability which might be due to the protection of the substrate provides against sudden thermal and pH changes. An immobilized enzyme also has the advantage of being able to be removed from the rest of the composition easily. An immobilized enzyme may include a soluble enzyme that is attached to a substrate. Examples of substrates may include polyurethane foams, polyacrylamide gels, polyethylene maleic anhydride gels, polystyrene maleic anhydride gels, cellulose, nitrocellulose, silastic resins, porous glass, macroporous glass membranes, glass beads, activated clay, zeolites, alumina, silica, silicate and other inorganic and organic substrates. The enzyme may be attached to the substrate in various ways including carrier covalent binding, crosslinking, physical adsorption, ionic binding, and entrapping.

In an aspect, the peroxide-reducing enzyme is added into a peracid use solution instead of a concentrated peracid composition. Without being limited to a mechanism of action, the use of a peroxide-reducing enzyme agent is preferably added to a non-concentrated peracid composition in order to maintain the viability and peroxide-reducing capability of the agent. For example, in an aspect, a concentrated peracid composition (e.g. about 10 wt-% or greater peracid, or about 15 wt-% or greater peracid) is diluted into a water source and thereafter the peroxide-reducing enzyme agent is added. In an aspect, the dilute water source may be the water source in need of treatment according to the invention. In another aspect, the dilute water source may be a use solution of the peracid composition (or less concentrated peracid composition) for subsequent dosing into the water source in need of treatment according to the invention.

Peracids

In some aspects, a peracid is included for antimicrobial efficacy in the compositions for water treatment. As used herein, the term "peracid" may also be referred to as a "percarboxylic acid" or "peroxyacid." Sulfoperoxycarboxylic acids, sulfonated peracids and sulfonated peroxycarboxylic acids are also included within the term "peracid" as used herein. The terms "sulfoperoxycarboxylic acid," "sulfonated peracid," or "sulfonated peroxycarboxylic acid" refers to the peroxycarboxylic acid form of a sulfonated carboxylic acid as disclosed in U.S. Pat. No. 8,344,026, and U.S. Patent Publication Nos. 2010/0048730 and 2012/0052134, each of which are incorporated herein by reference in their entirety. As one of skill in the art appreciates, a peracid refers to an acid having the hydrogen of the hydroxyl group in carboxylic acid replaced by a hydroxy group. Oxidizing peracids may also be referred to herein as peroxycarboxylic acids.

A peracid includes any compound of the formula R—(COOOH)$_n$, in which R can be hydrogen, alkyl, alkenyl, alkyne, acrylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acrylic," "alicyclic group," "aryl," "heteroaryl," and "heterocyclic group" are as defined herein.

As used herein, the term "alkyl" includes a straight or branched saturated aliphatic hydrocarbon chain having from 1 to 22 carbon atoms, such as, for example, methyl, ethyl, propyl, isopropyl (1-methylethyl), butyl, tert-butyl (1,1-dimethylethyl), and the like. The term "alkyl" or "alkyl groups" also refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like. The alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like.

Further, as used herein the term "alicyclic" includes any cyclic hydrocarbyl containing from 3 to 8 carbon atoms. Examples of suitable alicyclic groups include cyclopropanyl, cyclobutanyl, cyclopentanyl, etc. The term "heterocyclic" includes any closed ring structures analogous to carbocyclic groups in which one or more of the carbon atoms in the ring is an element other than carbon (heteroatom), for example, a nitrogen, sulfur, or oxygen atom. Heterocyclic groups may be saturated or unsaturated. Examples of suitable heterocyclic groups include for example, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan. Additional examples of suitable heterocyclic groups include groups derived from tetrahydrofurans, furans, thiophenes, pyrrolidines, piperidines, pyridines, pyrrols, picoline, coumaline, etc.

According to the invention, alkyl, alkenyl, alicyclic groups, and heterocyclic groups can be unsubstituted or substituted by, for example, aryl, heteroaryl, $C_{1-4}$ alkyl, $C_{1-4}$ alkenyl, $C_{1-4}$ alkoxy, amino, carboxy, halo, nitro, cyano, —$SO_3H$, phosphono, or hydroxy. When alkyl, alkenyl, alicyclic group, or heterocyclic group is substituted, preferably the substitution is $C_{1-4}$ alkyl, halo, nitro, amido, hydroxy, carboxy, sulpho, or phosphono. In one embodiment, R includes alkyl substituted with hydroxy. The term "aryl" includes aromatic hydrocarbyl, including fused aromatic rings, such as, for example, phenyl and naphthyl. The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc. The term "heteroaryl" also includes fused rings in which at least one ring is aromatic, such as, for example, indolyl, purinyl, benzofuryl, etc.

According to the invention, aryl and heteroaryl groups can be unsubstituted or substituted on the ring by, for example, aryl, heteroaryl, alkyl, alkenyl, alkoxy, amino, carboxy, halo, nitro, cyano, —$SO_3H$, phosphono, or hydroxy. When aryl, aralkyl, or heteroaryl is substituted, preferably the substitution is $C_{1-4}$ alkyl, halo, nitro, amido, hydroxy, carboxy, sulpho, or phosphono. In one embodiment, R includes aryl substituted with $C_{1-4}$ alkyl.

Peracids suitable for use include any peroxycarboxylic acids, including varying lengths of peroxycarboxylic and percarboxylic acids (e.g. C1-22) that can be prepared from the acid-catalyzed equilibrium reaction between a carboxylic acid described above and hydrogen peroxide. A peroxycarboxylic acid can also be prepared by the auto-oxidation of aldehydes or by the reaction of hydrogen peroxide with an acid chloride, acid hydride, carboxylic acid anhydride, or sodium alcoholate. Alternatively, peracids can be prepared through non-equilibrium reactions, which may be generated for use in situ, such as the methods disclosed in U.S. Patent Publication Nos. 2012/0172440 and 2012/0172441 each titled "In Situ Generation of Peroxycarboxylic Acids at Alkaline pH, and Methods of Use Thereof," which are incorporated herein by reference in their entirety. Preferably a composition of the invention includes peroxyacetic acid, peroxyoctanoic acid, peroxypropionic acid, peroxylactic acid, peroxyheptanoic acid, peroxyoctanoic acid and/or peroxynonanoic acid.

In some embodiments, a peroxycarboxylic acid includes at least one water-soluble peroxycarboxylic acid in which R includes alkyl of 1-22 carbon atoms. For example, in one embodiment, a peroxycarboxylic acid includes peroxyacetic acid. In another embodiment, a peroxycarboxylic acid has R that is an alkyl of 1-22 carbon atoms substituted with hydroxy. Methods of preparing peroxyacetic acid are known to those of skill in the art including those disclosed in U.S. Pat. No. 2,833,813, which is herein incorporated herein by reference in its entirety.

In another embodiment, a sulfoperoxycarboxylic acid has the following formula:

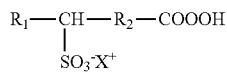

wherein $R_1$ is hydrogen, or a substituted or unsubstituted alkyl group; $R_2$ is a substituted or unsubstituted alkylene group; X is hydrogen, a cationic group, or an ester forming moiety; or salts or esters thereof. In some embodiments, $R_1$ is a substituted or unsubstituted $C_m$ alkyl group; X is hydrogen a cationic group, or an ester forming moiety; $R_2$ is a substituted or unsubstituted $C_n$ alkyl group; m=1 to 10; n=1 to 10; and m+n is less than 18, or salts, esters or mixtures thereof.

In some embodiments, $R_1$ is hydrogen. In other embodiments, $R_1$ is a substituted or unsubstituted alkyl group. In some embodiments, $R_1$ is a substituted or unsubstituted alkyl group that does not include a cyclic alkyl group. In some embodiments, $R_1$ is a substituted alkyl group. In some embodiments, $R_1$ is an unsubstituted $C_1$-$C_9$ alkyl group. In some embodiments, $R_1$ is an unsubstituted $C_7$ or $C_8$ alkyl. In other embodiments, $R_1$ is a substituted $C_8$-$C_{10}$ alkylene group. In some embodiments, $R_1$ is a substituted $C_8$-$C_{10}$ alkyl group is substituted with at least 1, or at least 2 hydroxyl groups. In still yet other embodiments, $R_1$ is a substituted $C_1$-$C_9$ alkyl group. In some embodiments, $R_1$ is a substituted $C_1$-$C_9$ substituted alkyl group is substituted with at least 1 $SO_3H$ group. In other embodiments, $R_1$ is a $C_9$-$C_{10}$ substituted alkyl group. In some embodiments, $R_1$ is a substituted $C_9$-$C_{10}$ alkyl group wherein at least two of the carbons on the carbon backbone form a heterocyclic group. In some embodiments, the heterocyclic group is an epoxide group.

In some embodiments, $R_2$ is a substituted $C_1$-$C_{10}$ alkylene group. In some embodiments, $R_2$ is a substituted $C_8$-$C_{10}$ alkylene. In some embodiments, $R_2$ is an unsubstituted $C_6$-$C_9$ alkylene. In other embodiments, $R_2$ is a $C_8$-$C_{10}$ alkylene group substituted with at least one hydroxyl group. In some embodiments, $R_2$ is a $C_{10}$ alkylene group substituted with at least two hydroxyl groups. In other embodiments, $R_2$ is a $C_8$ alkylene group substituted with at least one $SO_3H$ group. In some embodiments, $R_2$ is a substituted $C_9$ group, wherein at least two of the carbons on the carbon backbone form a heterocyclic group. In some embodiments, the heterocyclic group is an epoxide group. In some embodiments, $R_1$ is a $C_8$-$C_9$ substituted or unsubstituted alkyl, and $R_2$ is a $C_7$-$C_8$ substituted or unsubstituted alkylene.

These and other suitable sulfoperoxycarboxylic acid compounds for use in the stabilized peroxycarboxylic acid compositions of the invention are further disclosed in U.S. Pat. No. 8,344,026 and U.S. Patent Publication Nos. 2010/0048730 and 2012/0052134, which are incorporated herein by reference in its entirety.

In additional embodiments a sulfoperoxycarboxylic acid is combined with a single or mixed peroxycarboxylic acid composition, such as a sulfoperoxycarboxylic acid with peroxyacetic acid, peroxyoctanoic acid and sulfuric acid (PSOA/POOA/POAA/$H_2SO_4$). In other embodiments, a mixed peracid is employed, such as a peroxycarboxylic acid including at least one peroxycarboxylic acid of limited water solubility in which R includes alkyl of 5-22 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably a composition of the invention includes peroxyacetic acid and peroxyoctanoic acid. Other combinations of mixed peracids are well suited for use in the current invention.

In another embodiment, a mixture of peracetic acid and peroctanoic acid is used to treat a water source, such as disclosed in U.S. Pat. No. 5,314,687 which is herein incorporated by reference in its entirety. In an aspect, the peracid mixture is a hydrophilic peracetic acid and a hydrophobic peroctanoic acid, providing antimicrobial synergy. In an aspect, the synergy of a mixed peracid system allows the use of lower dosages of the peracids.

In another embodiment, a tertiary peracid mixture composition, such as peroxysulfonated oleic acid, peracetic acid and peroctanoic acid are used to treat a water source, such as disclosed in U.S. Pat. No. 8,344,026 which is incorporated herein by reference in its entirety. A combination of the three peracids provides significant antimicrobial synergy providing an efficient antimicrobial composition for the water treatment methods according to the invention. In addition, it is thought the high acidity built in the composition assists in removing chemical contaminants from the water (e.g. sulfite and sulfide species), and the defoaming agent (e.g. aluminum sulfate) provides defoaming (e.g. combating foam caused by any anionic surface active agents used in the water treatment).

Advantageously, a combination of peroxycarboxylic acids provides a composition with desirable antimicrobial activity in the presence of high organic soil loads. The mixed peroxycarboxylic acid compositions often provide synergistic micro efficacy. Accordingly, compositions of the invention can include a peroxycarboxylic acid, or mixtures thereof.

Various commercial formulations of peracids are available, including for example peracetic acid (15%) and hydrogen peroxide (10%) available as EnviroSan (Ecolab, Inc., St.

Paul Minn.). Most commercial peracid solutions state a specific percarboxylic acid concentration without reference to the other chemical components in a use solution. However, it should be understood that commercial products, such as peracetic acid, will also contain the corresponding carboxylic acid (e.g. acetic acid), hydrogen peroxide and water.

In an aspect, any suitable $C_1$-$C_{22}$ percarboxylic acid can be used in the present compositions. In some embodiments, the $C_1$-$C_{22}$ percarboxylic acid is a $C_2$-$C_{20}$ percarboxylic acid. In other embodiments, the $C_1$-$C_{22}$ percarboxylic is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In still other embodiments, the $C_1$-$C_{22}$ percarboxylic acid comprises peroxyacetic acid, peroxyoctanoic acid and/or peroxysulfonated oleic acid.

In an aspect of the invention, a peracid is present in a use solution with the water source in need of treatment in an amount of between about 1 ppm and about 5000 ppm, preferably between about 1 ppm and about 2000 ppm, preferably between about 1 ppm and about 1000 ppm, and more preferably between about 1 ppm and about 100 ppm. Without limiting the scope of invention, the numeric ranges are inclusive of the numbers defining the range and include each integer within the defined range. The amount of peracid above the preferred range of 100 ppm may be employed for highly contaminated waters in need of treatment, such as source waters including increased amounts of produced water (e.g. recycled waters).

In an aspect of the invention, a peracid may be selected from a concentrated composition having a ratio of hydrogen peroxide to peracid from about 0:100 to about 0.5:100, preferably from about 0.5:100 to about 1:10. Various concentrated peracid compositions having the hydrogen peroxide to peracid ratios of about 0:100 to about 0.5:100, preferably from about 0.5:100 to about 1:10 may be employed to produce a use solution for treatment according to the methods of the invention. In a further aspect of the invention, a peracid may have a ratio of hydrogen peroxide to peracid as low as from about 0.001 part or 0.01 part hydrogen peroxide to about 1 part peracid. Preferably, any ratio wherein the amount of hydrogen peroxide is less than peracid is suitable for use according to the invention in formulating a use solution for water treatments. Without limiting the scope of invention, the numeric ranges are inclusive of the numbers defining the range and include each integer within the defined range.

Obtaining the preferred hydrogen peroxide to peroxycarboxylic acid ratios in a peracid composition may be obtained by a variety of methods suitable for producing a very low hydrogen peroxide to peracid ratio. In an aspect, equilibrium peracid compositions may be distilled to recover a very low hydrogen peroxide peracid mixture. In yet another aspect, catalysts for hydrogen peroxide decomposition may be combined with a peracid composition, including for example, peroxide-reducing agents and/or other biomimetic complexes. In yet another aspect, perhydrolysis of peracid precursors, such as esters (e.g. triacetin) and amides may be employed to obtain peracids with very low hydrogen peroxide.

In a particularly preferred aspect, the ester and amide peracid precursors have alkyl leaving groups ranging in carbon chain lengths of C1-C8. In each of these aspects, the peroxycarboxylic acid concentration ranges from 0.0001 wt-% to 20 wt-%, preferably from about 0.0001 wt-% to 10 wt-%, or from about 0.0001 wt-% to 5 wt-%, or from about 1 wt-% to about 3 wt-%. Without limiting the scope of invention, the numeric ranges are inclusive of the numbers defining the range and include each integer within the defined range.

In an aspect of the invention, a peroxide-reducing agent is combined with a peracid composition. In an aspect, a peracid composition having a concentration of less than or equal to about 10% may be combined with the peroxide-reducing agent, without having a detrimental effect on the peroxide-reducing agent. In a further preferred aspect, a peracid composition having a concentration of less than or equal to about 5% is suitable for use with the peroxide-reducing agent, without having a detrimental effect on the peroxide-reducing agent. In a still further preferred aspect, a peracid concentration of less than or equal to 3% is preferred, or less than or equal to 2%. Without limiting the scope of invention, the numeric ranges are inclusive of the numbers defining the range and include each integer within the defined range.

Hydrogen Peroxide

The present invention includes reduced amounts of hydrogen peroxide, and preferably no hydrogen peroxide. Hydrogen peroxide, $H_2O_2$, provides the advantages of having a high ratio of active oxygen because of its low molecular weight (34.014 g/mole) and being compatible with numerous substances that can be treated by methods of the invention because it is a weakly acidic, clear, and colorless liquid. Another advantage of hydrogen peroxide is that it decomposes into water and oxygen. It is advantageous to have these decomposition products because they are generally compatible with substances being treated. For example, the decomposition products are generally compatible with metallic substance (e.g., substantially noncorrosive) and are generally innocuous to incidental contact and are environmentally friendly.

In one aspect of the invention, hydrogen peroxide is initially in an antimicrobial peracid composition in an amount effective for maintaining equilibrium between a carboxylic acid, hydrogen peroxide, water and a peracid. The amount of hydrogen peroxide should not exceed an amount that would adversely affect the antimicrobial activity of a composition of the invention. In further aspects of the invention, hydrogen peroxide concentration is significantly reduced within an antimicrobial peracid composition, preferably containing hydrogen peroxide at a concentration as close to zero as possible. That is, the concentration of hydrogen peroxide is minimized, through the use of the selected peroxide-reducing agents according to the invention. In further aspects, the concentration of hydrogen peroxide is reduced and/or eliminated as a result of distilled equilibrium peracid compositions, other catalysts for hydrogen peroxide decomposition (e.g. biomimetic complexes) and/or the use of perhydrolysis of esters (e.g. triacetin) to obtain peracids with very low hydrogen peroxide.

According to the invention, an advantage of minimizing the concentration of hydrogen peroxide is that antimicrobial activity of a composition of the invention is improved as compared to conventional equilibrium peracid compositions. Without being limited to a particular theory of the invention, significant improvements in antimicrobial efficacy result from enhanced peracid, namely POAA stability from the reduced hydrogen peroxide concentration.

In an aspect of the invention, hydrogen peroxide can typically be present in a use solution in an amount less than 2500 ppm, preferably less than 2000 ppm, more preferably less than 1000 ppm. In preferred embodiments, the use of a catalase reduces the hydrogen peroxide concentration as close to zero as possible, preferably a concentration of zero.

Without limiting the scope of invention, the numeric ranges are inclusive of the numbers defining the range and include each integer within the defined range.

In further aspects of the invention, hydrogen peroxide in a peracid composition is reduced by at least 50%, at least 60%, at least 70%, at least 80%, or at least 90%. Preferably the hydrogen peroxide is substantially zero after the treatment of a peracid composition according to the invention. In additional aspects, the ratio of hydrogen peroxide to peracid in a concentrated composition for use according to the invention is from about 0:100 to about 1:10, preferably from about 0.5:100 to about 0.5:10. Various concentrated peracid compositions with a hydrogen peroxide to peracid ratio from about 0:100 to about 1:10, preferably from about 0.5:100 to about 0.5:10, may be employed to produce a use solution for treatment according to the invention. Without limiting the scope of invention, the numeric ranges are inclusive of the numbers defining the range and include each integer within the defined range.

In a further aspect, a use solution may have a ratio of hydrogen peroxide to peracid as low as from about 0.001 part hydrogen peroxide to about 1 part peracid. Preferably, any ratio wherein the amount of hydrogen peroxide is less than peracid is suitable for use according to the invention in formulating a use solution for water treatments. Without limiting the scope of invention, the numeric ranges are inclusive of the numbers defining the range and include each integer within the defined range.

Carboxylic Acid

The present invention includes a carboxylic acid with the peracid composition and hydrogen peroxide. A carboxylic acid includes any compound of the formula R—(COOH)$_n$ in which R can be hydrogen, alkyl, alkenyl, alkyne, acylic, alicyclic group, aryl, heteroaryl, or heterocylic group, and n is 1, 2, or 3. Preferably R includes hydrogen, alkyl, or alkenyl. The terms "alkyl," "alkenyl," "alkyne," "acylic," "alicyclic group," "aryl," "heteroaryl," and "heterocyclic group" are as defined above with respect to peracids.

Examples of suitable carboxylic acids according to the equilibrium systems of peracids according to the invention include a variety monocarboxylic acids, dicarboxylic acids, and tricarboxylic acids. Monocarboxylic acids include, for example, formic acid, acetic acid, propanoic acid, butanoic acid, pentanoic acid, hexanoic acid, heptanoic acid, octanoic acid, nonanoic acid, decanoic acid, undecanoic acid, dodecanoic acid, glycolic acid, lactic acid, salicylic acid, acetylsalicylic acid, mandelic acid, etc. Dicarboxylic acids include, for example, adipic acid, fumaric acid, glutaric acid, maleic acid, succinic acid, malic acid, tartaric acid, etc. Tricarboxylic acids include, for example, citric acid, trimellitic acid, isocitric acid, agaicic acid, etc.

In an aspect of the invention, a particularly well suited carboxylic acid is water soluble such as formic acid, acetic acid, propionic acid, butanoic acid, lactic acid, glycolic acid, citric acid, mandelic acid, glutaric acid, maleic acid, malic acid, adipic acid, succinic acid, tartaric acid, etc. Preferably a composition of the invention includes acetic acid, octanoic acid, or propionic acid, lactic acid, heptanoic acid, octanoic acid, or nonanoic acid. Additional examples of suitable carboxylic acids are employed in sulfoperoxycarboxylic acid or sulfonated peracid systems, which are disclosed in U.S. Pat. No. 8,344,026, and U.S. Patent Publication Nos. 2010/0048730 and 2012/0052134, each of which are herein incorporated by reference in their entirety.

Any suitable $C_1$-$C_{22}$ carboxylic acid can be used in the present compositions. In some embodiments, the $C_1$-$C_{22}$ carboxylic acid is a $C_2$-$C_{20}$ carboxylic acid. In other embodiments, the $C_1$-$C_{22}$ carboxylic acid is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In still other embodiments, the $C_1$-$C_{22}$ carboxylic acid comprises acetic acid, octanoic acid and/or sulfonated oleic acid.

In an aspect of the invention, a carboxylic acid is present in a use solution with the water source in need of treatment in an amount of between about 1 ppm and about 5000 ppm, preferably between about 1 ppm and about 2000 ppm, preferably between about 1 ppm and about 1000 ppm, and more preferably between about 1 ppm and about 100 ppm. Without limiting the scope of invention, the numeric ranges are inclusive of the numbers defining the range and include each integer within the defined range. The amount of carboxylic acid above the preferred range of 100 ppm may be employed for highly contaminated waters in need of treatment, such as source waters including increased amounts of produced water (e.g. recycled waters).

Additional Optional Materials

The composition can optionally include additional ingredients to enhance the composition for water treatment according to the invention, including for example, friction reducers, viscosity enhancers and the like. Additional optional functional ingredients may include for example, peracid stabilizers, emulsifiers, corrosion inhibitors and/or descaling agents (i.e. scale inhibitors), surfactants and/or additional antimicrobial agents for enhanced efficacy (e.g. mixed peracids, biocides), antifoaming agents, acidulants (e.g. strong mineral acids) or other pH modifiers, additional carboxylic acids, and the like. In an embodiment, no additional functional ingredients are employed.

Friction Reducers

Friction reducers are used in water or other water-based fluids used in hydraulic fracturing treatments for subterranean well formations in order to improve permeability of the desired gas and/or oil being recovered from the fluid-conductive cracks or pathways created through the fracking process. The friction reducers allow the water to be pumped into the formations more quickly. Various polymer additives have been widely used as friction reducers to enhance or modify the characteristics of the aqueous fluids used in well drilling, recovery and production applications.

Examples of commonly used friction reducers include polyacrylamide polymers and copolymers. In an aspect, additional suitable friction reducers may include acrylamide-derived polymers and copolymers, such as polyacrylamide (sometime abbreviated as PAM), acrylamide-acrylate (acrylic acid) copolymers, acrylic acid-methacrylamide copolymers, partially hydrolyzed polyacrylamide copolymers (PHPA), partially hydrolyzed polymethacrylamide, acrylamide-methyl-propane sulfonate copolymers (AMPS) and the like. Various derivatives of such polymers and copolymers, e.g., quaternary amine salts, hydrolyzed versions, and the like, should be understood to be included with the polymers and copolymers described herein.

Friction reducers are combined with water and/or other aqueous fluids, which in combination are often referred to as "slick water" fluids. Slick water fluids have reduced frictional drag and beneficial flow characteristics which enable the pumping of the aqueous fluids into various gas- and/or oil-producing areas, including for example for fracturing.

In an aspect of the invention, a friction reducer is present in a use solution in an amount between about 100 ppm to 1000 ppm. In a further aspect, a friction reducer is present in a use solution in an amount of at least about 0.01 wt-% to about 10 wt-%, preferably at least about 0.01 wt-% to about 5 wt-%, preferably at least about 0.01 wt-% to about 1 wt-%, more preferably at least about 0.01 wt-% to about 0.5 wt-%, and still more preferably at least about 0.01 wt-% to about 0.1 wt-%. Without limiting the scope of invention, the numeric ranges are inclusive of the numbers defining the range and include each integer within the defined range.

Beneficially, the compositions and methods of the invention do not negatively interfere with friction reducers included in an aqueous solution. Without being limited to a particular theory of the invention, it is thought that the reduction and/or elimination of the oxidant hydrogen peroxide from the peracid composition promotes the stability and efficacy of any variation in the amount of friction reducer present in a use solution.

Viscosity Enhancers

Viscosity enhancers are additional polymers used in water or other water-based fluids used in hydraulic fracturing treatments to provide viscosity enhancement. Natural and/or synthetic viscosity-increasing polymers may be employed in compositions and methods according to the invention. Viscosity enhancers may also be referred to as gelling agents and examples include guar, xanthan, cellulose derivatives and polyacrylamide and polyacrylate polymers and copolymers, and the like.

In an aspect of the invention, a viscosity enhancer is present in a use solution in an amount between about 100 ppm to 1000 ppm. In a further aspect, a viscosity enhancer is present in a use solution in an amount of at least about 0.01 wt-% to about 10 wt-%, preferably at least about 0.01 wt-% to about 5 wt-%, preferably at least about 0.01 wt-% to about 1 wt-%, at least about 0.01 wt-% to about 2 wt-%, preferably at least about 0.01 wt-% to about 1 wt-%, preferably at least about 0.01 wt-% to about 0.5 wt-%. Without limiting the scope of invention, the numeric ranges are inclusive of the numbers defining the range and include each integer within the defined range.

Beneficially, the compositions and methods of the invention do not negatively interfere with viscosity enhancer included in an aqueous solution. Without being limited to a particular theory of the invention, it is believed the reduction and/or elimination of the oxidant hydrogen peroxide from the peracid composition promotes the stability and efficacy of any variation in the amount of viscosity enhancer present in a use solution.

Corrosion Inhibitors

Corrosion inhibitors are additional molecules used in oil and gas recovery operations. Corrosion inhibitors that may be employed in the present disclosure are disclosed in U.S. Pat. No. 5,965,785, U.S. Patent Publication No. 2010/0108566, GB Patent No. 1,198,734, WO/03/006581, WO04/044266, and WO08/005058, each of which are incorporated herein by reference in their entirety.

In an aspect of the invention, a corrosion inhibitor is present in a use solution in an amount between about 100 ppm to 1000 ppm. In a further aspect, a corrosion inhibitor is present in a use solution in an amount of at least about 0.0001 wt-% to about 10 wt-%, preferably at least about 0.0001 wt-% to about 5 wt-%, preferably at least about 0.0001 wt-% to about 1 wt-%, preferably at least about 0.0001 wt-% to about 0.1 wt-%, and still more preferably at least about 0.0001 wt-% to about 0.05 wt-%. Without limiting the scope of invention, the numeric ranges are inclusive of the numbers defining the range and include each integer within the defined range.

Beneficially, the compositions and methods of the invention do not negatively interfere with corrosion inhibitor included in an aqueous solution. Without being limited to a particular theory of the invention, it is believed the reduction and/or elimination of the oxidant hydrogen peroxide from the peracid composition promotes the stability and efficacy of any variation in the amount of corrosion inhibitor present in a use solution.

Scale Inhibitors

Scale inhibitors are additional molecules used in oil and gas recovery operations. Common scale inhibitors that may be employed in these types of applications include polymers and co-polymers, phosphates, phosphate esters and the like.

In an aspect of the invention, a scale inhibitor is present in a use solution in an amount between about 100 ppm to 1000 ppm. In a further aspect, a scale inhibitor is present in a use solution in an amount of at least about 0.0001 wt-% to about 10 wt-%, at least about 0.0001 wt-% to about 1 wt-%, preferably at least about 0.0001 wt-% to about 0.1 wt-%, preferably at least about 0.0001 wt-% to about 0.05 wt-%. Without limiting the scope of invention, the numeric ranges are inclusive of the numbers defining the range and include each integer within the defined range.

Beneficially, the compositions and methods of the invention do not negatively interfere with scale inhibitor included in an aqueous solution. Without being limited to a particular theory of the invention, it is thought that the reduction and/or elimination of the oxidant hydrogen peroxide from the peracid composition promote the stability and efficacy of any variation in the amount of scale inhibitor present in a use solution.

Additional Antimicrobial Agents

Additional antimicrobial agents may be included in the compositions and/or methods of the invention for enhanced antimicrobial efficacy. In addition to the use of mixed peracid compositions, additional antimicrobial agents (e.g. surfactants) and biocides may be employed. Additional biocides may include, for example, a quaternary ammonium compound as disclosed in U.S. Pat. No. 6,627,657, which is incorporated herein by reference in its entirety. Beneficially, the presence of the quaternary ammonium compound provides both synergistic antimicrobial efficacies with peracids, as well as maintains long term biocidal efficacy of the compositions.

In another embodiment, the additional biocide may include an oxidizer compatible phosphonium biocide, such as tributyl tetradecyl phosphonium chloride. The phosphonium biocide provides similar antimicrobial advantages as the quaternary ammonium compound in combination with the peracids. In addition, the phosphonium biocide is compatible with the anionic polymeric chemicals commonly used in the oil field applications, such as the methods of the fracking disclosed according to the invention.

Additional antimicrobial and biocide agents may be employed in amounts sufficient to provide antimicrobial efficacy, as may vary depending upon the water source in need of treatment and the contaminants therein. Such agents may be present in a use solution in an amount of at least about 0.1 wt-% to about 50 wt-%, preferably at least about 0.1 wt-% to about 20 wt-%, more preferably from about 0.1 wt-% to about 10 wt-%. Without limiting the scope of invention, the numeric ranges are inclusive of the numbers defining the range and include each integer within the defined range.

Acidulants

Acidulants may be included as additional functional ingredients in a composition according to the invention. In an aspect, a strong, oxidative mineral acid such as nitric acid or sulfuric acid can be used to treat water sources, as disclosed in U.S. Pat. No. 4,587,264, which is incorporated herein by reference in its entirety. For example, the combined use of a strong mineral acid with the peracid composition provides enhanced antimicrobial efficacy as a result of the acidity assisting in removing chemical contaminants within the water source (e.g. sulfite and sulfide species). In an aspect of the invention, the use of an acidulant, such as a mineral acid, is suitable for decreasing the pH of the water source and/or the treated peracid composition to obtain additional and/or synergistic impact on cleaning efficacy.

In an aspect, an acidulant may be used to decrease the pH of the water source in need of treatment to a pH below about 6, preferably below about 5, and more preferably between about 4.5 and about 5.5 to get a synergistic impact on water clean-up from the acid. In a preferred aspect, an acidulant is used to decrease the pH of the treated water source from about 2 to about 6 to provide a synergistic impact on water clean-up. According to such an embodiment, any acidulant may be employed to decrease the pH of the water source. Examples of suitable acidulants include hydrochloric acid and other acids, and chlorine, chlorine dioxide ($ClO_2$) and other oxidants.

In addition, some strong mineral acids, such as nitric acid, provide a further benefit of reducing the risk of corrosion toward metals contacted by the peracid compositions according to the invention. Exemplary peracid products containing nitric acid are commercially available from Enviro Tech Chemical Services, Inc. (Reflex brand) and from Solvay Chemicals (Proxitane® NT brand).

In a still further aspect, an acidulant may be employed to decrease the pH of the peracid composition according to the invention to increase the peracid stability by decreasing the pH of the peracid composition. For example, in some embodiments decreasing the pH of the treated peracid composition from about 8 or greater to less than about 8, or less than about 7.5, or less than about 7 has a beneficial impact on the peracid stability for use according to the methods of the invention.

Acidulants may be employed in amounts sufficient to provide the intended antimicrobial efficacy, peracid stability and/or anticorrosion benefits, as may vary depending upon the peracid composition and/or water source in need of treatment and the contaminants therein. Such agents may be present in a use solution in an amount of at least about 0.1 wt-% to about 50 wt-%, preferably at least about 0.1 wt-% to about 20 wt-%, more preferably from about 0.1 wt-% to about 10 wt-%. Without limiting the scope of invention, the numeric ranges are inclusive of the numbers defining the range and include each integer within the defined range.

Peracid Stabilizers

In some embodiments, the compositions of the present invention include one or more stabilizing agents. The stabilizing agents can be used, for example, to stabilize the peracid and hydrogen peroxide and prevent the premature oxidation of this constituent within the composition of the invention.

In some embodiments, an acidic stabilizing agent can be used. Thus, in some embodiments, the compositions of the present invention can be substantially free of an additional acidulant.

Suitable stabilizing agents include, for example, chelating agents or sequestrants. Suitable sequestrants include, but are not limited to, organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, aminocarboxylic acids, or heterocyclic carboxylic acids, e.g., pyridine-2,6-dicarboxylic acid (dipicolinic acid).

In some embodiments, the compositions of the present invention include dipicolinic acid as a stabilizing agent. Compositions including dipicolinic acid can be formulated to be free or substantially free of phosphorous.

In other embodiments, the sequestrant can be or include phosphonic acid or phosphonate salt. Suitable phosphonic acids and phosphonate salts include HEDP; ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; picolinic, dipicolinic acid or mixtures thereof. In some embodiments, organic phosphonates, e.g., HEDP are included in the compositions of the present invention.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino(tri(methylenephosphonic acid)), ($N[CH_2PO_3H_2]_3$), available from Monsanto as DEQUEST® 2000; ethylenediamine[tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The sequestrant can be or include aminocarboxylic acid type sequestrant. Suitable aminocarboxylic acid type sequestrants include the acids or alkali metal salts thereof, e.g., amino acetates and salts thereof. Suitable aminocarboxylates include N-hydroxyethy laminodiacetic acid; hydroxyethylenediaminetetraacetic acid, nitrilotriacetic acid (NTA); ethylenediaminetetraacetic acid (EDTA); N-hydroxyethyl-ethy lenediaminetriacetic acid (HEDTA); diethylenetriaminepentaacetic acid (DTPA); and alanine-N,N-diacetic acid; and the like; and mixtures thereof.

The sequestrant can be or include a polycarboxylate. Suitable polycarboxylates include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

In certain embodiments, the present composition includes about 0.01 to about 10 wt-% stabilizing agent, about 0.4 to about 4 wt-% stabilizing agent, about 0.6 to about 3 wt-% stabilizing agent, about 1 to about 2 wt-% stabilizing agent. It is to be understood that all values and ranges within these values and ranges are encompassed by the present invention.

Methods of Use

In some aspects, the methods disclosed for water treatment in oil and gas recovery provide effective antimicrobial efficacy without any deleterious interaction with functional agents, including for example friction reducers. In a further aspect, the methods for water treatment according to the invention using the peroxide-reducing agent provide increased antimicrobial efficacy compared to the use of the antimicrobial peracids alone. In a still further aspect, the methods of use result in the disposal of cleaner water with low numbers of microorganisms. In yet a still further aspect of the methods of the invention, the reduction and/or elimination of $H_2O_2$ from the peracid compositions minimizes the negative effects of the oxidant $H_2O_2$.

Use in Water Treatment

The treated peracid compositions (i.e. reduced or no hydrogen peroxide peracid compositions) can be used for a variety of industrial applications, e.g., to reduce microbial or viral populations on a surface or object or in a body or stream of water. In some aspects, the invention includes methods of using the treated peracid compositions to prevent biological fouling in various industrial processes and industries, including oil and gas operations, to control microorganism growth, eliminate microbial contamination, limit or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, the peracid and peroxide-reducing enzyme agent (e.g. catalase) compositions (or other treated peracid compositions having low to substantially no hydrogen peroxide) are used to control the growth of microorganisms in water used in various oil and gas operations. In a further aspect, the compositions are suitable for incorporating into fracturing fluids to control or eliminate microorganisms.

As used herein for the methods of the invention, treated peracid compositions can employ a variety of peracid compositions having a low to substantially no hydrogen peroxide concentration. These treated peracid compositions include peracid compositions with a peroxide-reducing agent to reduce the hydrogen peroxide to peracid ratio and/or other reduced hydrogen peroxide peracid compositions disclosed herein. In a preferred embodiment, peracid and peroxide-reducing agent use solutions having reduced or substantially no hydrogen peroxide are introduced to a water source in need of treatment.

The methods by which the treated peracid use solutions are introduced into the aqueous fluids according to the invention are not critical. Introduction of the treated peracid compositions (and/or introduction of the two or more part system, such as a peracid composition and a peroxide-reducing agent composition, may be carried out in a continuous or intermittent manner and will depend on the type of water being treated.

In an aspect, treated peracid use solutions are employed according to the methods of the invention. As referred to herein, treated peracid compositions or treated peracid use solutions are understood to refer to peracid compositions having reduced or substantially no hydrogen peroxide. Such reduced or substantially no hydrogen peroxide peracid compositions may be generated by use of peroxide-reducing agent(s) at a point of use (e.g. combining more than one component part of the composition—e.g. the peroxide-reducing agent and a peracid composition in a two part system) and/or generated prior to a point of use.

In an aspect, the treated peracid compositions are generated at a point of use, and may be generated within a water source on site. In an aspect, the peracid composition and a peroxide-reducing agent, such as a metal and/or strong oxidizing agent, are combined with a water source at a point of use and the hydrogen peroxide concentration of the use solution is reduced within a period of time from at least a minute to a few hours, preferably from at least 5 minutes to a few hours. One skilled in the art will ascertain that the treatment time for a use solution of a peracid composition within a water source to be treated will vary depending upon the concentration of the peroxide-reducing agent and/or the volume of the peracid composition and/or water source in need of treatment. The concentrations of the peracid composition and peroxide-reducing agent will further vary depending upon the amount of bacteria within the water source in need of treatment.

In an aspect, the treated peracid use solutions are added to waters in need of treatment prior to the drilling and fracking steps in order to restrict the introduction of microbes into the reservoir and to prevent the microbes from having a negative effect on the integrity of the fluids. The treatment of source waters (e.g. pond, holding tank, lake, municipal, etc.) and/or produced waters is particularly well suited for use according to the invention.

The treated waters according to the invention can be used for both slick water fracturing (i.e. using frictions reducers) and/or gel fracturing (i.e. using viscosity enhancers), depending on the type of formation being fractured and the type of hydrocarbon expected to be produced. Use of a treated peracid use solution, namely a peroxide-reducing agent treated peracid composition use solution having low to substantially no hydrogen peroxide, is suitable for both slick water fracturing and gel fracturing.

In an aspect, pretreating the peracid composition, such as peracetic acid (including a mixture of acetic acid, hydrogen peroxide and water) with a peroxide-reducing agent substantially removes the hydrogen peroxide with minimal to no impact on the fracturing fluids and the well itself. In an aspect, the peracetic acid pretreated with a peroxide-reducing agent allows the formation of gel suitable for gel fracturing, as opposed to untreated peracetic acid/hydrogen peroxide solutions that do not allow a gel to form. In a further aspect, the treated peracid use solutions are added to waters in need of treatment in the subterranean well formations (e.g. introduced through a bore hole in a subterranean formation). These methods provide additional control within the well formation suitable for reducing microbial populations already present within the down hole tubing in the well or within the reservoir itself.

In a still further aspect, the treated peracid use solutions are added to waters in need of treatment before disposal. In such an aspect, flow back waters (e.g. post fracking) are treated to minimize microbial contaminations in the waters and to remove solids prior to disposal of the water into a subterranean well, reuse in a subsequent fracturing application or return of the water into local environmental water sources.

In a still further aspect, the treated peracid use solutions are added to waters in need of treatment before disposal. In such an aspect, flow back waters (e.g. post fracking) are treated to minimize microbial contaminations in the waters and to remove solids prior to disposal of the water into a subterranean well, reuse in a subsequent fracturing application or return of the water into local environmental water sources.

In an alternative aspect, the treated peracid use solution may be formed within the water source to be treated. For example, a peracid composition is provided to a water source and a peroxide-reducing agent is thereafter provided to the water source, such that the reduction and/or elimination of peroxide concentration occur within the water source. These methods provide additional control within the well formation suitable for reducing microbial populations already present within the down hole tubing in the well or within the reservoir itself.

In an aspect of the invention, the methods of treating a water source may include the cyclical dosing of treated (e.g. low or no hydrogen peroxide) peracid compositions to a water source. In an alternative aspect, the methods of treating a water source may include the cyclical dosing of a water source with a two (or more) part composition used to generate the treated (e.g. low or no hydrogen peroxide) peracid composition within the water source in need of treatment. Such cyclical dosing may include daily dosing, every two or more day dosing, every three or more day dosing, every four or more day dosing, every five or more day dosing, every six or more day dosing, weekly dosing, or longer frequency dosing. In a preferred aspect, the water source is treated in an every five day cycle for optimal reduction or elimination of hydrogen peroxide within a peracid composition used to treat the water source. Without being limited according to the mechanism and/or the scope of the invention, all ranges of the dosing cycles are included within the scope of the invention. In an aspect, the present invention is directed to a method for treating water, which method comprises providing the above compositions to a water source in need of treatment to form a treated water source, wherein said treated water source comprises from about 1 ppm to about 1,000 ppm of said $C_1$-$C_{22}$ percarboxylic acid. Any suitable $C_1$-$C_{22}$ percarboxylic acid can be used in the present methods. For example, peroxyacetic acid, peroxyoctanoic acid and/or peroxysulfonated oleic acid can be used. In some embodiments, a combination of peroxyacetic acid, peroxyoctanoic acid and peroxysulfonated oleic acid is used.

The treated peracid composition provides a water source with any suitable concentration of the hydrogen peroxide. In some embodiments, the treated water source comprises from about 1 ppm to about 15 ppm of the hydrogen peroxide. In other embodiments, the treated water source comprises about 1 ppm, 2 ppm, 3 ppm, 4 ppm, 5 ppm, 6 ppm, 7 ppm, 8 ppm, 9 ppm, 10 ppm, 11 ppm, 12 ppm, 13 ppm, 14 ppm, or 15 ppm of the hydrogen peroxide.

In an aspect, the treated peracid use solutions may be added to an incoming stream of water, such as water added to a holding tank or other storage reservoir. In an embodiment, the treated peracid use solutions are added to provide a peracid concentration (e.g. peracetic acid) applied at a rate of about 1 ppm to about 5000 ppm peracid, from about 1 ppm to about 2000 ppm, from about 1 ppm to about 1000 ppm, from about 1 ppm to about 500 ppm, and preferably from about 1 ppm to about 100 ppm peracid. Without being limited according to the mechanism and/or the scope of the invention, all ranges are included within the scope of the invention.

In an alternative aspect, the treated peracid use solutions may be added at an elevated peracid concentration (e.g. about 200 to about 5000 ppm) to an intermittent water source (e.g. a smaller holding tank, such as up to about 1000 gallons of water) prior to dilution within a larger holding tank or other storage reservoir for a water source (e.g. 1 million gallons of water or more). Upon such dilution within a larger water source the peracid becomes quickly diluted to the preferred rate of about 0.1 ppm to about 100 ppm peracid, preferably from about 1 ppm to about 100 ppm peracid. Without being limited to a mechanism of action, such a method beneficially provides a rapid kill of microorganisms within a controlled/smaller volume of a water source in need of treatment, while still providing a static or slower antimicrobial activity within a bulk water system. In a still further alternative aspect, the treated peracid use solutions may be added to a larger bulk fluid, such as the holding tank or other storage reservoir for a water source. For example, in some aspects, a bulk fluid source may be a holding tank or other storage reservoir having a volume from about 1000 gallons to about 20 million gallons or more, preferably from about 1000 gallons to about 12 million gallons. In such an embodiment, the treated peracid use solutions provide a peracid concentration (e.g. peracetic acid) in the bulk water source from 0.1 ppm to about 100 ppm peracid or greater, preferably from about 1 ppm to about 100 ppm peracid or greater. Without being limited according to the mechanism and/or the scope of the invention, all ranges are included within the scope of the invention.

According to the various aspects of the invention, monitoring devices and/or means may be included to measure the application rate and/or bulk solution of peracid in order to ensure either the application rate of peracid (or the bulk solution having a maintained peracid) at a concentration of from 0.1 ppm to about 100 ppm peracid or greater, preferably from about 1 ppm to about 100 ppm peracid or greater.

In an aspect, the treated peracid use solutions may be added to dormant water sources. As one skilled in the art will ascertain, the use of treated peracid use solutions in dormant water sources will often require less frequent dosing that other water sources. For example, use of the treated water sources during non-pumping (e.g. non-use) periods, such as for example winter, will require less frequent dosing due to the more static nature of the water source at that particular time.

In a still further aspect, the treated peracid use solutions are added to waters in need of treatment before disposal. In such an aspect, flow back waters (e.g. post fracking) are treated to minimize microbial contaminations in the waters and to remove solids prior to disposal of the water into a subterranean well, reuse in a subsequent fracturing application or return of the water into local environmental water sources. Such flow back waters may be held, for example, in tanks, ponds or the like, in some aspects of the invention.

In an aspect, the water source in need of treatment may vary significantly. For example, the water source may be a freshwater source (e.g. pond water), salt water or brine source, brackish water source, recycled water source, or the like. In an aspect, wherein offshore well drilling operations are involved, seawater sources are often employed (e.g. saltwater or non-saltwater). Beneficially, the peracid and peroxide-reducing agent compositions of the invention are suitable for use with any types of water and provide effective antimicrobial efficiency with any of such water sources.

Large volumes of water are employed according to the invention as required in well fluid operations. As a result, in an aspect of the invention, recycled water sources (e.g. produced waters) are often employed to reduce the amount of a freshwater, pond water or seawater source required. Recycled or produced water are understood to include non-potable water sources. The use of such produced waters (in combination with freshwater, pond water or seawater) reduces certain economic and/or environmental constraints. In an aspect of the invention, thousands to millions of gallons of water may be employed and the combination of produced water with fresh water sources provides significant economic and environmental advantages.

In an aspect of the invention, as much produced water as practical is employed. In an embodiment at least 1% produced water is employed, preferably at least 5% produced water is employed, preferably at least 10% produced water is employed, preferably at least 20% produced water is employed, or more preferably more than 20% produced water is employed. Without being limited according to the mechanism and/or the scope of the invention, all ranges are included within the scope of the invention.

The treated water source can comprise any suitable concentration of the $C_1$-$C_{22}$ percarboxylic acid. In some embodiments, the treated water source comprises from about 10 ppm to about 200 ppm of the $C_1$-$C_{22}$ percarboxylic acid. In other embodiments, the treated water source comprises about 1 ppm, 10 ppm, 100 ppm, 200 ppm, 300 ppm, 400 ppm, 500 ppm, 600 ppm, 700 ppm, 800 ppm, 900 ppm or 1,000 ppm of the $C_1$-$C_{22}$ percarboxylic acid. The present methods can be used to treat any suitable or desirable water sources. In another example, the present methods can be used to treat fresh water, pond water, sea water, produced water and a combination thereof. In some embodiments, the water source comprises at least about 1 wt-% produced water. In other embodiments, the water source comprises at least about 1 wt-%, 2 wt-%, 3 wt-%, 4 wt-%, 5 wt-%, 6 wt-%, 7 wt-%, 8 wt-%, 9 wt-%, or 10 wt-%, 15 wt-%, 20 wt-%, 25 wt-%, 30 wt-% or more produced water.

In an aspect of the invention, the method includes a pretreatment step, wherein the peracid composition is treated with a peroxide-reducing agent to reduce the hydrogen peroxide concentration in a use solution. The pretreatment step occurs prior to combining the peracid antimicrobial composition and/or peroxide-reducing agent to a water source in need of treatment. In an aspect of the invention, the pretreatment may occur within a few minutes to hours before addition to a water source. Preferably, a commercial peracid formulation is employed (e.g. peracetic acid). Thereafter, the peracid and peroxide-reducing agent composition use solution may be diluted to obtain the desired peracetic acid concentrations, with low and/or no hydrogen peroxide concentration.

According to embodiments of the invention, a sufficient amount of the pretreated peracid and peroxide-reducing agent use solution composition is added to the aqueous water source in need of treatment to provide the desired peracid concentration for antimicrobial efficacy. For example, a water source is dosed amounts of the peracid and peroxide-reducing agent use solution composition until a peracid concentration within the water source is detected within the preferred concentration range (e.g. about 1 ppm to about 100 ppm peracid). In an aspect, it is preferred to have a microbial count of less than about 100,000 microbes/mL, more preferably less than about 10,000 microbes/mL, or more preferably less than about 1,000 microbes/mL. Without being limited according to the mechanism and/or the scope of the invention, all ranges are included within the scope of the invention.

In some embodiments, the level of a microorganism, if present in the water source, is stabilized or reduced by the present methods. For example, at least 10%, 20%, 30%, 40%, 50%, 60%, 70%, 80%, or 90% or more of the microorganism, if present in the water source, is killed, destroyed, removed and/or inactivated by the present methods. In a further aspect of the invention, the method includes a pretreatment step of the water source. In some aspects, the water source in need of treatment may be first dosed an acidulant to decrease the pH of the water source. Beneficially, in an aspect of the invention, the pretreatment of a water source with an acidulant provides increased peracid stability within the water source.

The methods of use as described herein can vary in the temperature and pH conditions associated with use of the aqueous treatment fluids. For example, the aqueous treatment fluids may be subjected to varying ambient temperatures according to the applications of use disclosed herein, including ranging from about 0° C. to about 180° C. in the course of the treatment operations. Preferably, the temperature range is between about 5° C. to about 100° C., more preferably between about 10° C. to about 80° C. Without being limited according to the mechanism and/or the scope of the invention, all ranges are included within the scope of the invention. However, as a majority of the antimicrobial activity of the compositions of the invention occurs over a short period of time, the exposure of the compositions to relatively high temperatures is not a substantial concern.

In addition, the peracid composition aqueous treatment fluids (i.e. use solutions) may be subjected to varying pH ranges, such as from 1 to about 10.5. Preferably, the pH range is less than about 9, less than about 8.2 (pKa value of the representative peracid peracetic acid) to ensure the effective antimicrobial efficacy of the peracid. In some aspects of the invention, a pH modifier (such as an acidulant) is added to a water source in need of treatment according to the invention. In some embodiments it may be desirable to decrease the pH to between about 5 and about 8.5. Without being limited according to the mechanism and/or the scope of the invention, all ranges are included within the scope of the invention.

The antimicrobial compositions of the invention are fast-acting. However, the present methods require a certain minimal contact time of the compositions with the water in need of treatment for occurrence of sufficient antimicrobial effect. The contact time can vary with concentration of the use compositions, method of applying the use compositions, temperature of the use compositions, pH of the use compositions, amount of water to be treated, amount of soil or substrates in the water to be treated, or the like. The contact or exposure time can be at least about 15 seconds. In some embodiments, the exposure time is about 1 to 5 minutes. In other embodiments, the exposure time is at least about 10 minutes, 30 minutes, or 60 minutes. In other embodiments, the exposure time is a few minutes to hours. In other embodiments, the exposure time is a few days or more. Beneficially, the compositions for use according to the invention are suitable for short contact times due in part to the non-oxidizing nature of the compositions having reduced or eliminated hydrogen peroxide content. The contact time will further vary based upon the concentration of peracid in a use solution.

In further aspects of the invention, the methods include the direction of the treated water compositions into a subterranean environment and/or a well-bore. In some aspects, the treated water compositions are directed into a subterranean environment and/or a well-bore at a speed faster than about 30 barrel (bbl.)/minute, faster than about 60 barrel (bbl.)/minute, and/or at a speed of about 65 barrel (bbl.)/minute and about 100 barrel (bbl.)/minute. Without being limited according to the mechanism and/or the scope of the invention, all ranges are included within the scope of the invention. As referred to herein, a subterranean environment may include, for example, a shale gas reservoir, a well, and/or an oil reservoir.

Beneficial Effects of the Methods of Use in Water Treatment

In some aspects, the methods disclosed for water treatment in oil and gas recovery provide effective antimicrobial efficacy without deleterious interaction with functional agents, including for example friction reducers. In a further aspect, the methods for water treatment provide increased antimicrobial efficacy compared to the use of the antimicrobial peracids alone. In a still further aspect, the methods of use result in the disposal of cleaner water with low numbers of microorganisms. In yet a further aspect of the methods of the invention, the reduction and/or elimination of $H_2O_2$ from the peracid compositions minimizes the negative effects of the oxidant $H_2O_2$.

In an aspect, the methods of use provide an antimicrobial for use that does not negatively impact the environment. Beneficially, the degradation of the compositions of the invention provides a "green" alternative. In an aspect of the invention, utilizing peroxyacetic acid is beneficial as the by-products are non-toxic, non-persistent in the environment, certified as organic and permitted for discharge in surface waters.

In a further aspect, the methods of use provide an antimicrobial for use that does not negatively interfere with friction reducers, viscosity enhancers and/or other functional ingredients. In a further aspect, the methods of use do not negatively interfere with any additional functional agents utilized in the water treatment methods, including for example, corrosion inhibitors, descaling agents, and the like. The compositions administered according to the invention provide extremely effective control of microorganisms without adversely affecting the functional properties of any additive polymers of an aqueous system. In addition, the treated peracid composition use solutions provide additional benefits to a system, including for example, reducing corrosion within the system due to the decreased or substantially eliminated hydrogen peroxide from a treated peracid composition. Beneficially, the non-deleterious effects of the treated peracid compositions (namely using a peroxide-reducing agent) on the various functional ingredients used in water treatment methods are achieved regardless of the make-up of the water source in need of treatment.

In an additional aspect, the methods of use prevent the contamination of systems, such as well or reservoir souring. In further aspects, the methods of use prevent microbiologically-influenced corrosion of the systems upon which it is employed.

In additional aspects of the invention, the reduction and/or elimination of hydrogen peroxide from the systems reduces volume expansion within sealed systems (e.g. wells). As a result there is a significantly decreased or eliminated risk of well blow outs due to the removal of gases within the antimicrobial compositions used for treating the various water sources.

In further aspects, the methods of use employ the antimicrobial and/or bleaching activity of the peracid compositions. For example, the invention includes a method for reducing a microbial population and/or a method for bleaching. These methods can operate on an article, surface, in a body or stream of water or a gas, or the like, by contacting the article, surface, body, or stream with the compositions. Contacting can include any of numerous methods for applying the compositions, including, but not limited to, providing the antimicrobial peracid compositions in an aqueous use solution and immersing any articles, and/or providing to a water source in need of treatment.

The compositions are suitable for antimicrobial efficacy against a broad spectrum of microorganisms, providing broad spectrum bactericidal and fungistatic activity. For example, the peracid biocides of this invention provide broad spectrum activity against wide range of different types of microorganisms (including both aerobic and anaerobic microorganisms), including bacteria, yeasts, molds, fungi, algae, and other problematic microorganisms associated with oil- and gas-field operations.

Exemplary microorganisms susceptible to the peracid compositions of the invention include, gram positive bacteria (e.g., *Staphylococcus aureus*, *Bacillus* species (sp.) like *Bacillus subtilis*, Clostridia sp.), gram negative bacteria (e.g., *Escherichia coli*, *Pseudomonas* sp., *Klebsiella pneumoniae*, *Legionella pneumophila*, *Enterobacter* sp., *Serratia* sp., *Desulfovibrio* sp., and *Desulfotomaculum* sp.), yeasts (e.g., *Saccharomyces cerevisiae* and *Candida albicans*), molds (e.g., *Aspergillus niger*, *Cephalosporium acremonium*, *Penicillium notatum*, and *Aureobasidium pullulans*), filamentous fungi (e.g., *Aspergillus niger* and *Cladosporium resinae*), algae (e.g., *Chlorella vulgaris*, *Euglena gracilis*, and *Selenastrum capricornutum*), and other analogous microorganisms and unicellular organisms (e.g., phytoplankton and protozoa).

Use in Other Treatments

Additional embodiments of the invention include water treatments for various industrial processes for treating liquid systems. As used herein, "liquid system" refers to flood waters or an environment within at least one artificial artifact, containing a substantial amount of liquid that is capable of undergoing biological fouling. Liquid systems include but are not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In a further aspect, the compositions and methods can also be used to treat other liquid systems where both the compositions' antimicrobial function and oxidant properties can be utilized. Aside from the microbial issues surrounding waste water, waste water is often rich in malodorous compounds of reduced sulfur, nitrogen or phosphorous. A strong oxidant such as the compositions disclosed herein converts these compounds efficiently to their odor free derivatives e.g. the sulfates, phosphates and amine oxides. These same properties are very useful in the pulp and paper industry where the property of bleaching is also of great utility.

In a still further aspect, the compositions and methods can also be used for various aseptic treatment uses. Description of various applications of use of treated peracid compositions having low or reduced hydrogen peroxide are disclosed for example in U.S. Pat. No. 8,226,939, entitled "Antimicrobial Peracid Compositions with Selected Catalase Enzymes and Methods of Use in Aseptic Packaging," which is incorporated by reference in its entirety.

In an aspect, aseptic packaging fillers, including both categories: a single use filler and a re-use or recirculating filler, are suitable for using the compositions and methods of the invention. The single use system makes a dilute stock solution of peracid. It sprays a small amount of this solution in the inside of a package to sterilize it. The solution can be heated at the point of injection or it can be pre-heated prior to injection into the bottle. In either case the running conditions (temperature, contact time, and peracid concentration) are chosen so that the bottle is rendered commercially sterile. After contacting in the inside of the bottle, this spent solution drains from the bottle and is exported by the filler either to a drain or to other parts of the machine for environmental antimicrobial treatments or treatment of the exterior of the bottles. After the bottle has been treated it will be rinsed with microbial pure water, filled with a liquid food and sealed. All of these steps occur inside of a positive pressure zone inside the filler called the sterile zone. In a re-use filler, the filler contains a sump of diluted peracid solution. This sump is held at the desired temperature (40-65° C.). The filler draws from this sump and uses the solution to sterilize both the inside and outside of the bottles. The solution drains away from the bottles and it is collected and exported back to the same sump from which it originated. After the bottle has been treated it will be rinsed with microbiologically pure water, filled with a liquid food and sealed. All of these steps occur inside of a positive pressure zone inside the filler called a sterile zone.

In a further aspect, the compositions and methods can be used in aseptic packaging, including contacting the container with a composition according to the present invention. Such contacting can be accomplished using a spray device or soaking tank or vessel to intimately contact the inside of the container with the composition for sufficient period of time to clean or reduce the microbial population in the container. The container is then emptied of the amount of the present composition used. After emptying, the container can then be rinsed with potable water or sterilized water (which can include a rinse additive) and again emptied. After rinsing, the container can be filled with the food. The container is then sealed, capped or closed and then packed for shipment for ultimate sale. Examples of containers that can be filled include polyethylene terephthalate (PET), high density polyethylene (HDPE), polypropylene (PP), low density polyethylene, polycarbonate (PC), poly vinyl alcohol (PVA), aluminum, single or multilayer films or pouches, paperboard, steel, glass, multilayer bottles, other polymeric packaging material, combinations of these materials in films, pouches, bottle, or other food packaging materials.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference to the same extent as if each individual publication or patent application was specifically and individually indicated as incorporated by reference. All publications and patent applications in this specification are indicative of the level of ordinary skill in the art to which this invention pertains. The invention is further illustrated by the following examples, which should not be construed as further limiting.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Corrosion test were conducted. Corrosion rates were determined by a wheel box test, using bottles on a wheel in an oven. Each bottle contained a 1018 carbon steel coupon used for weight loss analysis upon completion of the test. The test was conducted using produced water (e.g. recycled water) from an oil/gas well and deionized water. The test was run at room temperature and in triplicates. The average corrosion rates were compared to blank samples (no chemical added). PAA/$H_2O_2$ was dosed at 50, 300 and 900 ppm. Catalase was added at 1000 ppm. The test duration was 24 hours.

Figure 2:
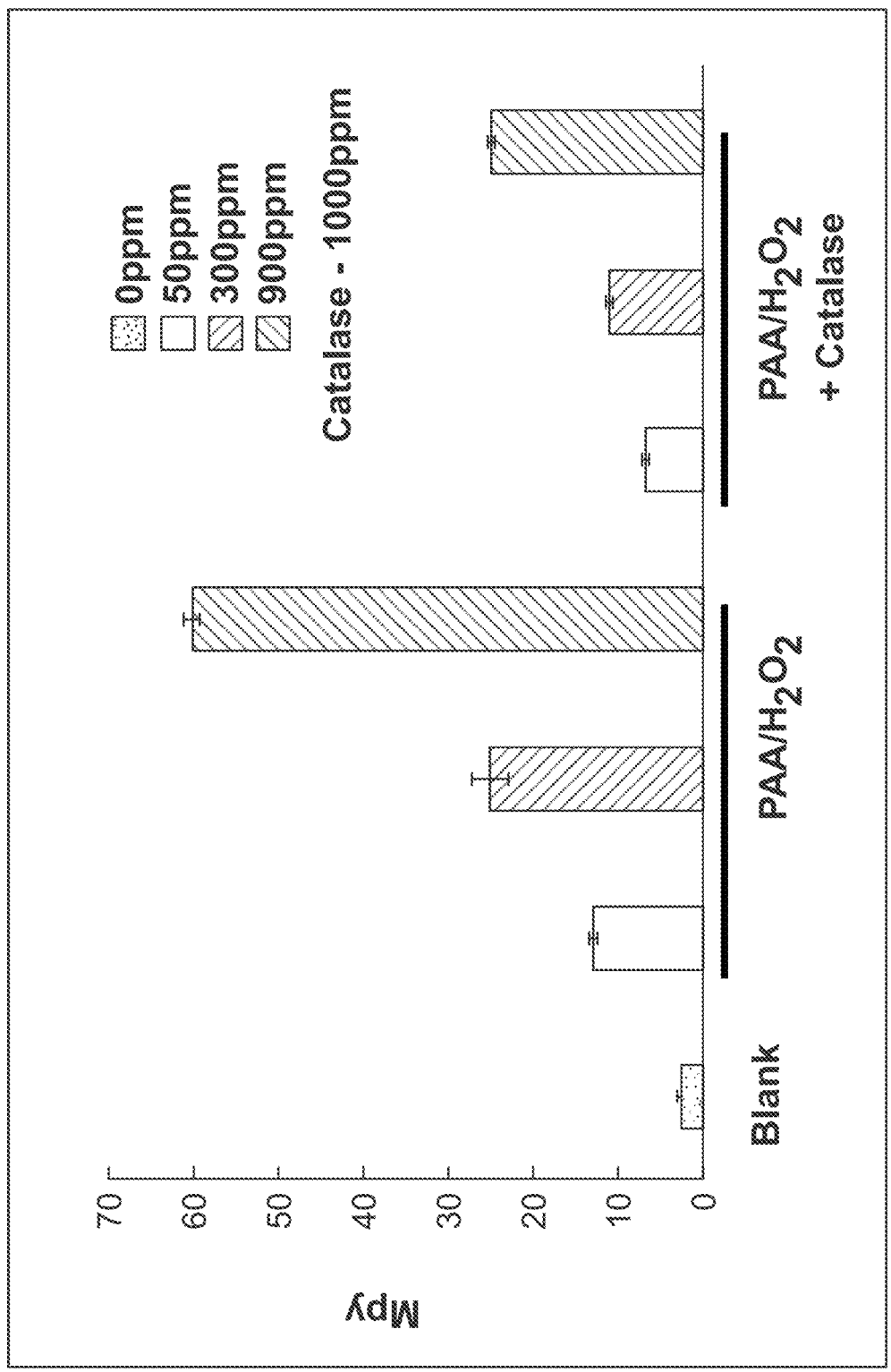

Results. The results from the corrosion tests for produced and deionized water are shown in FIG. 1. For a produced water sample, addition of 1000 ppm catalase to the PAA/$H_2O_2$ treatment decreased the corrosion rates of the 1018 carbon steel by approximately 30-50% (FIG. 1). In deionized water the reduction in corrosion rates reached almost 60% (FIG. 2).

Example 2

An evaluation of friction reducer interference was conducted. Viscosity measurements were obtained using a FANN Model 35 Viscometer. A total of 600 ml of tap water containing a friction reducer was treated with 200 ppm and 1000 ppm of peracetic acid with and without catalase. The mixture was blended for 15 seconds with a Hamilton Beach hand mixer and viscosity was measured at 300 rpm, room temperature. Viscosity values are reported in centipoise (cP).

Results. Table 1 shows the impact of PAA/$H_2O_2$ on friction reducers within a water source for oil/gas recovery, with and without the addition of catalase. A negative effect of the PAA/$H_2O_2$ was observed on both friction reducers. However, the effect was reduced in all cases following treatment with catalase indicating the addition of catalase to remove $H_2O_2$ reduces any negative impact of PAA/$H_2O_2$ on the friction reducers.

TABLE 1

| Biocide dosage | Friction Reducer (1 gpt) | With (Yes)/ Without (NO) catalase | Reading before chemical | Reading after chemical | Difference |
|---|---|---|---|---|---|
| PAA/$H_2O_2$ | 200 ppm | FR#1 | No | 5.5 | 4.5 | −1 |
| PAA/$H_2O_2$ | 200 ppm | FR#1 | Yes | 5 | 4.25 | −0.75 |
| PAA/$H_2O_2$ | 200 ppm | FR#2 | No | 3 | 2.5 | −0.5 |
| PAA/$H_2O_2$ | 200 ppm | FR#2 | Yes | 2.75 | 2.5 | −0.25 |
| PAA/$H_2O_2$ | 1000 ppm | FR#1 | No | 5.5 | 2.75 | −2.75 |
| PAA/$H_2O_2$ | 1000 ppm | FR#1 | Yes | 5 | 2.75 | −2.75 |
| PAA/$H_2O_2$ | 1000 ppm | FR#2 | No | 3 | 2.25 | −0.75 |
| PAA/$H_2O_2$ | 1000 ppm | FR#2 | Yes | 2.75 | 2.75 | 0 |

Example 3

The impact of water pretreatment with 500 ppm of the EnviroSan product (75 ppm POAA) on micro efficacy in various fracking water mixtures were evaluated. The example represents a baseline data set of various water treatment options according to the invention. Table 2 and FIG. 3 show the average log reduction in various slick water treatments with varying ppm PAA (without any catalase treatment or pretreatment), representing a baseline data set.

TABLE 2

| Holding Tank Pretreatment | Percentage Reuse H$_2$O | Slick Water Treatment | Avg. Log$_{10}$ Reduction 2.5 minutes | 5 minutes |
|---|---|---|---|---|
| None | 0% | 22 ppm POAA NO Catalase | 5.53 | 5.75 |
| 75 ppm PAA | 10% | 29 ppm POAA NO Catalase | 6.45 | 6.71 |
| None | | 36 ppm POAA | 4.32 | 4.72 |
| 75 ppm PAA | 20% | 47 ppm PAA NO Catalase | 6.42 | 6.55 |
| None | | 86 ppm POAA | 4.57 | 4.64 |
| 75 ppm PAA | 30% | 86 ppm POAA NO Catalase | 6.47 | 6.41 |
| None | | 138 ppm POAA | 4.12 | 5.00 |

Figure 3:
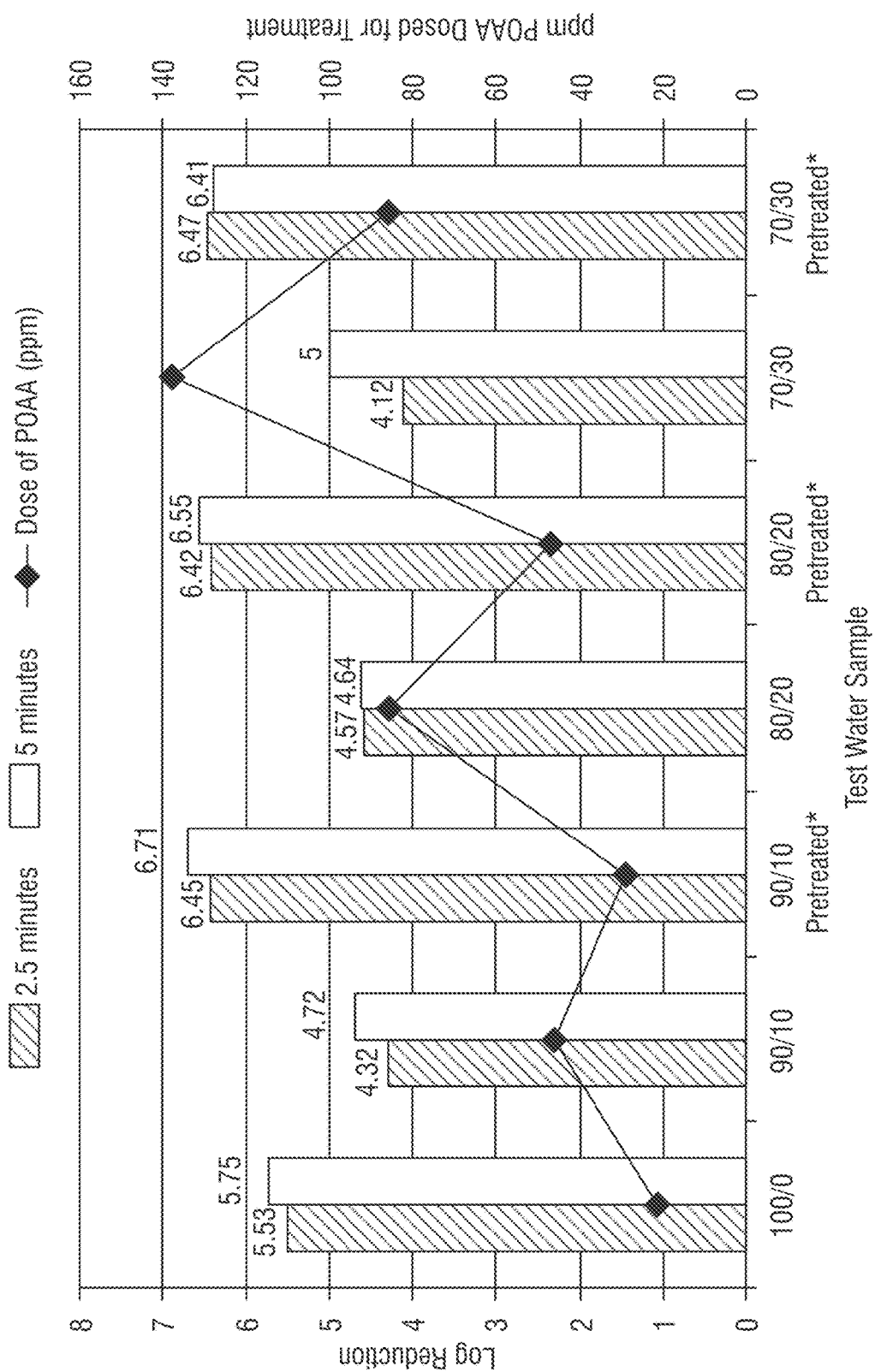
FIG. 3 shows the average log reduction generated after a 2.5 minute and 5 minute exposure time to varying concentrations of POAA required to achieve 20 ppm residual POAA within various fracking water mixtures.

FIG. 3 shows the increasing amount of POAA required in tested water samples having increased amounts of produced water (e.g. reused water).

Example 4

Planktonic kill studies were performed as an evaluation of biocide efficiency for PAA/H$_2$O$_2$ and PAA/H$_2$O$_2$/Catalase applications. Briefly, produced water samples were used to test the kill efficiency of PAA/H$_2$O$_2$ at the following dosages: 25, 50, 75, 150 and 300 ppm PAA. Concentration of catalase was fixed at 1000 ppm. The contact time was set to 10 and 60 minutes. After contact time, bacterial enumeration was performed using ATP quantification assay. Bacterial enumeration was calculated at the end of the appropriate time and biocide efficacy determined by comparison to an untreated sample.

Figure 4:
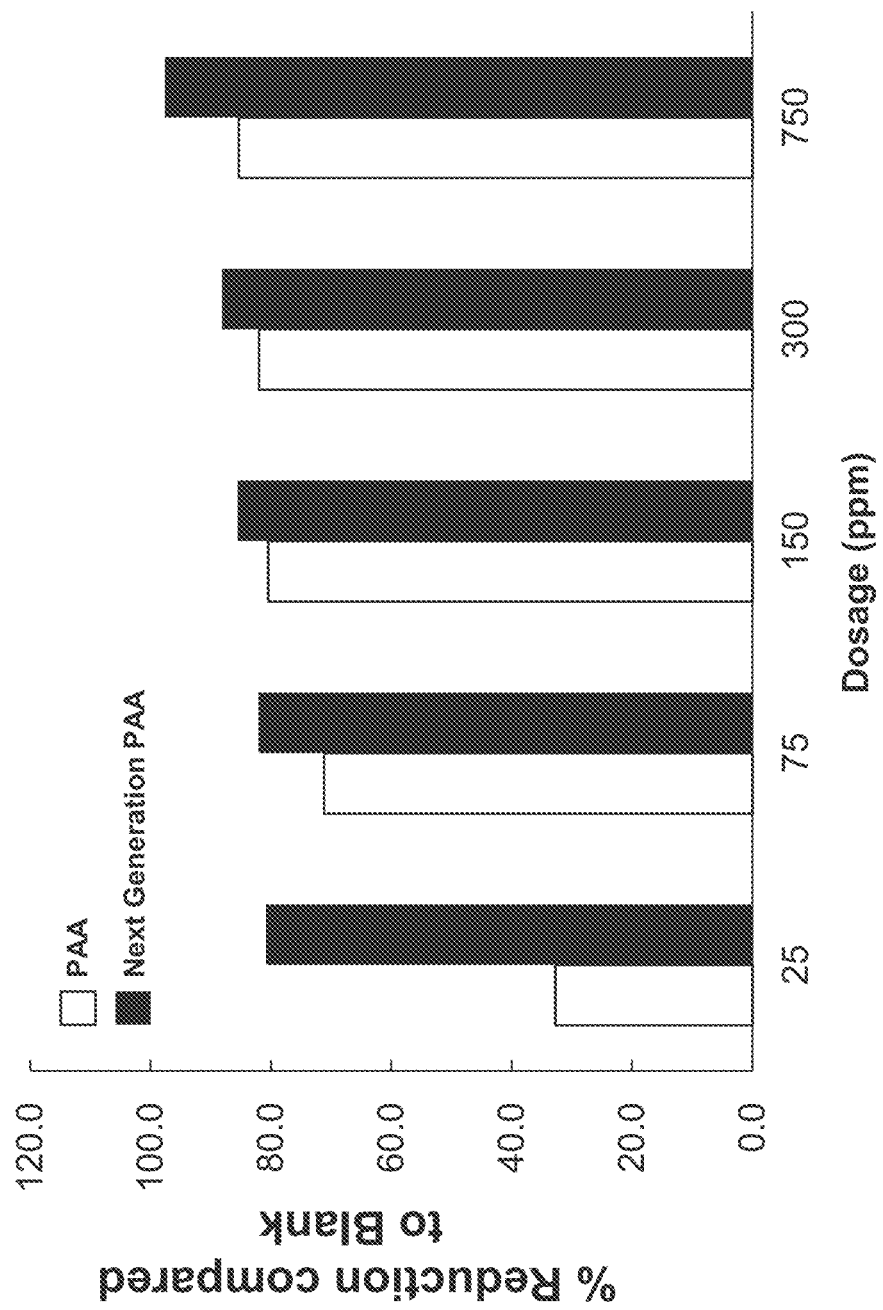
FIG. 4 shows the biocide efficiency of PAA/$H_2O_2$ and PAA/$H_2O_2$/Catalase compositions after a 10 minute contact period according to an embodiment of the invention.
Figure 5:
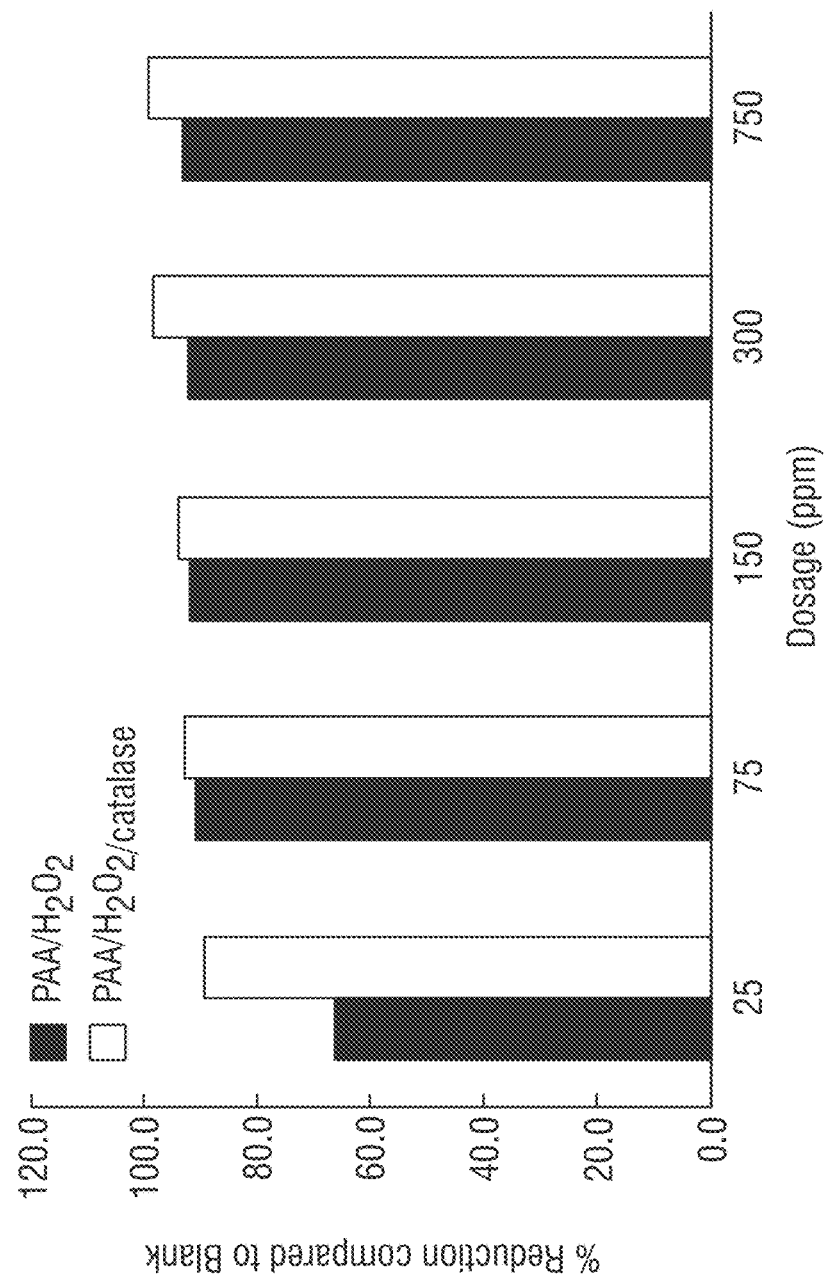
FIG. 5 shows the biocide efficiency of PAA/$H_2O_2$ and PAA/$H_2O_2$/Catalase compositions after a 60 minute contact period according to an embodiment of the invention.

Results. Planktonic kill studies demonstrate the addition of catalase increased microbial kill efficiency (FIGS. 4 and 5). For low dosage application of PAA/H$_2$O$_2$ (25 ppm), the addition of 1000 ppm of catalase increased the biocide efficiency by 48% after 10 minutes of treatment (23% after 60 minutes). The data from FIGS. 4 and 5 are also shown in Tables 3A and 3B (respectively).

TABLE 3A (10 minute contact)

| Dosage (ppm) | % Reduction compared to blank (PAA/H2O2) | % Reduction compared to blank (PAA/H2O2/catalase) |
|---|---|---|
| 25 | 32.7 | 80.8 |
| 75 | 71.2 | 82.1 |
| 100 | 80.5 | 85.5 |
| 300 | 82 | 88.1 |
| 750 | 85.3 | 97.6 |

TABLE 3B (60 minute contact)

| Dosage (ppm) | % Reduction compared to blank (PAA/H2O2) | % Reduction compared to blank (PAA/H2O2/catalase) |
|---|---|---|
| 25 | 66.6 | 89.6 |
| 75 | 90.8 | 92.8 |

TABLE 3B-continued (60 minute contact)

| Dosage (ppm) | % Reduction compared to blank (PAA/H2O2) | % Reduction compared to blank (PAA/H2O2/catalase) |
|---|---|---|
| 100 | 91.6 | 94 |
| 300 | 92.4 | 98.4 |
| 750 | 93.4 | 99.3 |

Example 5

Additional biocide testing was completed to assess the use of peracid and catalase compositions for water treatments used in oil fracking. The use of the commercially-available approximately 15 wt-% peracid (POAA) composition EnviroSan (Ecolab, Inc., St. Paul, Minn.) with and without catalase was evaluated for biocide efficacy in water treatments for oil fracking. In particular, an EnviroSan stock solution (approximately 1400 ppm POAA) with and without catalase was evaluated.

EnviroSan stock solutions with catalase were prepared as follows: 1 gram of EnviroSan (POAA) was added to 99 gram of deionized water in a beaker. With stirring, 100 µl of Optimase CA 400 L (catalase) was added through a syringe, and the stirring was continued for another 6.5 minutes. The subsequent assay (QATM 317) indicates that the resulting solution contains ~1400 ppm peracetic acid, and no detectable H$_2$O$_2$. The stock solution of EnviroSan with catalase is stable for at least 30 minutes without detectable changes on the level of POAA and/or H$_2$O$_2$.

A test system of *Pseudomonas aeruginosa* (ATCC 15442) and natural water bacterial populations was employed. *P. aeruginosa* were inoculated at ambient (18-22° C.) temperature using tryptone glucose extract (TGE) agar plating media and incubated at 35° C. for 48 hours.

Water mixtures as outlined in Table 3A were provided (showing the percentage of 100 mL of each water sample type). The various test substances and the amount of chemistry added to 10 mL of inoculated water sample to achieve 20 ppm residual POAA after 5 minutes within the water mixture are shown in Table 4B.

TABLE 4A

| Water Type | A | B | C* | D | E* | F | G* |
|---|---|---|---|---|---|---|---|
| Fresh | 100% | 90% | 90% | 80% | 80% | 70% | 70% |
| Produced | | 10% | 10% | 20% | 20% | 30% | 30% |

*Solutions pretreated with 300 ppm EnviroSan more than 24 hours before micro evaluation

TABLE 4B

| Water Type | A | B | C* | D | E* | F | G* |
|---|---|---|---|---|---|---|---|
| Vol. 1% Stock | 1701 μL | 320 μL | 320 μL | 600 μL | 600 μL | 960 μL | 960 μL |
| ppm POAA | 25 ppm | 46 ppm | 46 ppm | 87 ppm | 87 ppm | 140 ppm | 140 ppm |

Testing methods. Prior (24 hours) to micro testing, water mixtures C, E and G were mixed and pretreated with 300 ppm EnviroSan. Water samples were dispensed into sterile 250 mL Erlenmeyer flasks according to Table 4A, ensuring each flask contained 100 mL total of test water and mixed water types were completely homogeneous. Test water mixture was dispensed (24.75 mL) into a centrifuge tube and 0.25 mL of a $10^8$ CFU/mL culture of *P. aeruginosa* was added and mixed thoroughly. 1 mL of inoculated water mixture was serial diluted in PBDW. 10 mL of the inoculated water mixture was dispensed into 2 individual test tubes, where the appropriate volume of the EnviroSan solution with or without catalase (Table 4B) was added to achieve 20 ppm POAA residual to each test tube in timed intervals and mixed. The methods of Example 5 were employed to make the EnviroSan with catalase stock solutions. Then neutralized 1 mL samples in 9 mL of 0.5% sodium thiosulfate were obtained after 2.5 minutes, as well as 5 minutes.

Results. Aerobic bacterial populations (CFU/mL) present in water sample mixtures (both not pretreated and pretreated with 300 ppm EnviroSan) after inoculation with a *P. aeruginosa* culture, as well as survivors present 2.5 minutes and 5 minutes after the addition of EnviroSan POAA±catalase were evaluated as shown in Table 5.

TABLE 5

| Water Sample Type | Test Substance | Exposure Time | CFU/mL | $Log_{10}$ Growth | Av. $Log_{10}$ Growth | $Log_{10}$ Reduction |
|---|---|---|---|---|---|---|
| 100% Fresh | | After Inoculation | 6.90E+06 | 6.84 | 6.84 | |
| | EnviroSan 25 ppm POAA | 2.5 minutes | 1.00E+01 | 1.00 | 1.00 | 5.84 |
| | | 5 minutes | 8.00E+01 | 1.90 | 1.90 | 4.94 |
| | | 15 minutes | 6.00E+01 | 1.78 | 1.78 | 5.06 |
| | | 30 minutes | 2.00E+01 | 1.30 | 1.30 | 5.54 |
| | EnviroSan 25 ppm POAA + Catalase | 2.5 minutes | 7.00E+01 | 1.85 | 1.85 | 4.99 |
| | | 5 minutes | 4.00E+01 | 1.60 | 1.60 | 5.24 |
| | | 15 minutes | 3.00E+01 | 1.48 | 1.48 | 5.36 |
| | | 30 minutes | 2.00E+01 | 1.30 | 1.30 | 5.54 |
| 90% Fresh/ 10% Produced | | After Inoculation | 1.05E+07 | 7.02 | 7.02 | |
| | EnviroSan 46 ppm POAA | 2.5 minutes | 1.00E+01 | 1.00 | 1.00 | 6.02 |
| | | | 1.00E+01 | 1.00 | | |
| | | 5 minutes | 3.00E+01 | 1.48 | 1.24 | 5.78 |
| | | | 1.00E+01 | 1.00 | | |
| | | After Inoculation | 6.90E+06 | 6.84 | 6.84 | |
| | EnviroSan 46 ppm POAA + Catalase | 2.5 minutes | 1.00E+01 | 1.00 | 1.00 | 6.02 |
| | | | 1.00E+01 | 1.00 | | |
| | | 5 minutes | 2.00E+01 | 1.30 | 1.15 | 5.87 |
| | | | 1.00E+01 | 1.00 | | |
| 90/10 24 hour Pretreatment by 300 ppm EnviroSan Product | EnviroSan 46 ppm POAA | After Inoculation | 1.03E+07 | 7.01 | 7.01 | |
| | | 2.5 minutes | 4.00E+01 | 1.60 | 1.45 | 5.56 |
| | | | 2.00E+01 | 1.30 | | |
| | | 5 minutes | 1.00E+01 | 1.00 | 1.00 | 6.01 |
| | | | 1.00E+01 | 1.00 | | |
| 80% Fresh/ 20% Produced | | After Inoculation | 1.00E+06 | 6.00 | 6.00 | |
| | EnviroSan 87 ppm POAA | 2.5 minutes | 1.00E+01 | 1.00 | 1.50 | 4.50 |
| | | | 1.00E+02 | 2.00 | | |
| | | 5 minutes | 6.00E+01 | 1.78 | 1.74 | 4.26 |
| | | | 5.00E+01 | 1.70 | | |
| | | After Inoculation | 1.00E+06 | 6.00 | 6.00 | |
| | EnviroSan 87 ppm POAA + Catalase | 2.5 minutes | 4.00E+01 | 1.60 | 1.30 | 4.70 |
| | | | 1.00E+01 | 1.00 | | |
| | | 5 minutes | 4.00E+01 | 1.60 | 1.69 | 4.31 |
| | | | 6.00E+01 | 1.78 | | |
| 80/20 24 hour Pretreatment by 300 ppm EnviroSan Product | | After Inoculation | 1.00E+06 | 6.00 | 6.00 | |
| | EnviroSan 87 ppm POAA | 2.5 minutes | 2.00E+01 | 1.30 | 1.15 | 4.85 |
| | | | 1.00E+01 | 1.00 | | |
| | | 5 minutes | 2.00E+01 | 1.30 | 1.15 | 4.85 |
| | | | 1.00E+01 | 1.00 | | |

TABLE 5-continued

| Water Sample Type | Test Substance | Exposure Time | CFU/mL | Log₁₀ Growth | Av. Log₁₀ Growth | Log₁₀ Reduction |
|---|---|---|---|---|---|---|
| 70% Fresh/ 30% Produced | | After Inoculation | 5.90E+06 | 6.77 | 6.77 | |
| | EnviroSan 140 ppm | 2.5 minutes | 5.00E+01 7.00E+01 | 1.70 1.85 | 1.77 | 5.00 |
| | POAA | 5 minutes | 5.00E+01 5.00E+01 | 1.70 1.70 | 1.70 | 5.07 |
| | | After Inoculation | 6.00E+05 | 5.78 | 5.78 | |
| | EnviroSan 140 ppm | 2.5 minutes | 2.00E+01 5.00E+01 | 1.30 1.70 | 1.50 | 5.27 |
| | POAA + Catalase | 5 minutes | 4.00E+01 1.00E+01 | 1.60 1.00 | 1.30 | 5.47 |
| 70/30 24 hour Pretreatment by 300 ppm EnviroSan Product | | After Inoculation | 1.22E+07 | 7.09 | 7.09 | |
| | EnviroSan 140 ppm | 2.5 minutes | 1.00E+01 1.00E+01 | 1.00 1.00 | 1.00 | 6.09 |
| | POAA | 5 minutes | 1.00E+01 1.00E+01 | 1.00 1.00 | 1.00 | 6.09 |

Figure 6:
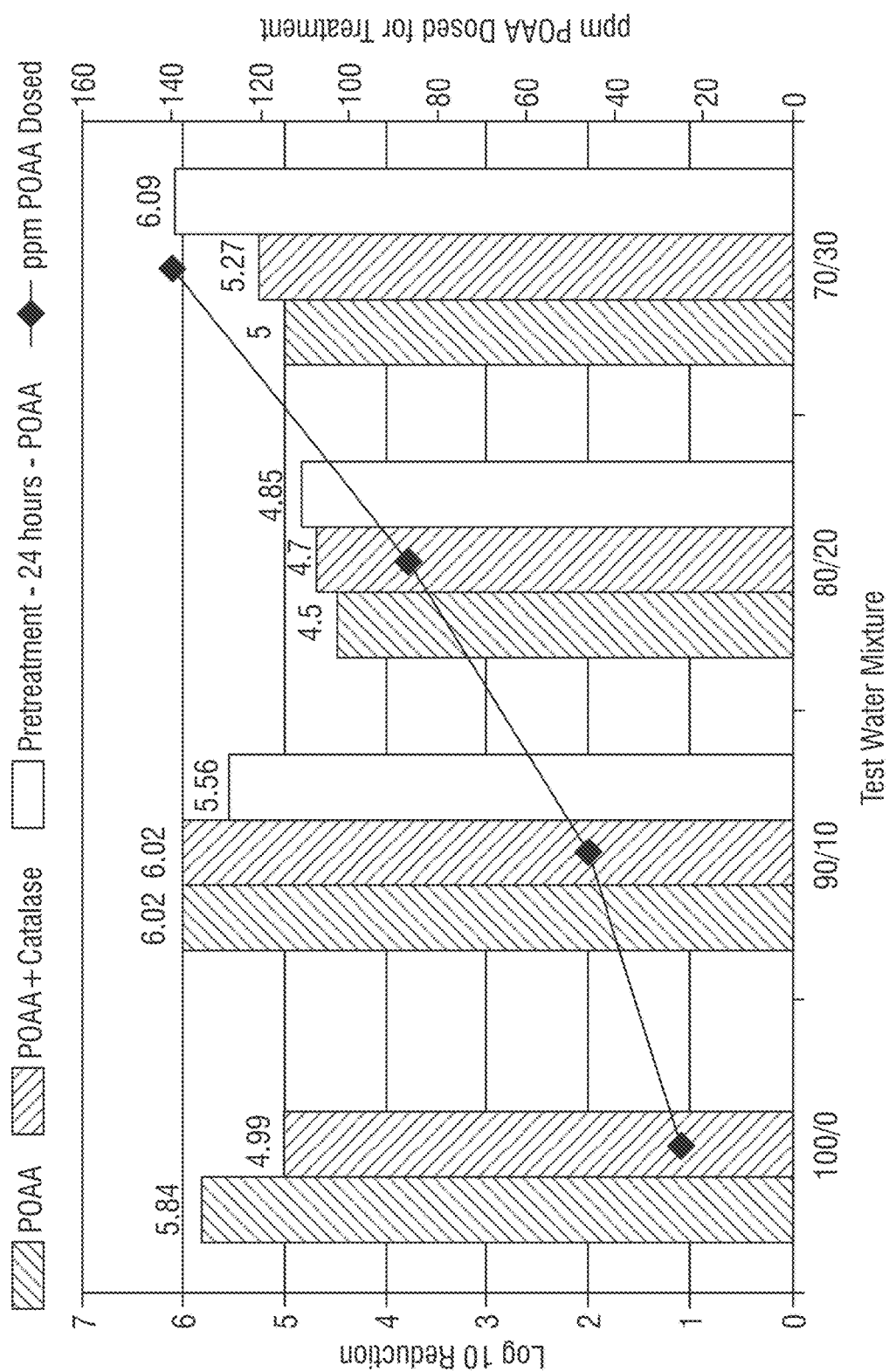
FIG. 6 shows the average log reduction generated after a 2.5 minute exposure time to varying concentrations of POAA to achieve 20 ppm residual POAA within fracking water mixtures.

The average log reduction generated after a 2.5 minute exposure is shown (FIG. 6) at varying concentrations of POAA required to achieve 20 ppm residual POAA after 5 minutes within its respective fracking water mixture. Across all tested fracking water mixtures, there does not appear to be a consistent trend to indicate that there are significant differences in efficacy generated between treatment of mixtures with POAA alone vs. POAA+catalase. The results indicate there is not a significant difference in bacterial reductions caused by pretreatment of the water mixtures 24 hours in advance with 300 ppm EnviroSan product, demonstrating the reduction of hydrogen peroxide with the catalase does not negatively impact micro efficacy.

Without being limited to a theory of the invention, it is likely the dosing of POAA chemistry is sufficiently high to generate significant kill by itself, without the potential benefits of water pretreatment or EnviroSan pre-reduction by catalase.

Example 6

Additional microbial testing was conducted to evaluate whether fracking waters treated with EnviroSan (POAA) pre-reduced with catalase (as shown in Example 5 to have significantly reduced consumption of POAA) result in improved micro efficacy. To evaluate improvements in micro efficacy, all water mixtures were treated with the same initial concentration of POAA EnviroSan (30 or 40 ppm) plus catalase, instead of aiming for a residual POAA level and adjusting initial dosing according to the amount of produced water present.

The test systems (*P. aeruginosa* and natural water) described in Example 5 were utilized. Water mixtures as outlined in Table 6 were provided (showing the percentage of 100 mL of each water sample type).

TABLE 6

| Water Type | A | B | C | D |
|---|---|---|---|---|
| Fresh | 100% | 90% | 80% | 70% |
| Produced | | 10% | 20% | 30% |

Water samples were dispensed into sterile 250 mL Erlenmeyer flasks according to Table 6, ensuring each flask contained 100 mL total of test water and mixed water types were completely homogeneous. 50 mL was saved for titration and 50 mL was used for micro evaluation. Test water mixture was dispensed (24.75 mL) into a centrifuge tube and 0.25 mL of a $10^8$ CFU/mL culture of *P. aeruginosa* was added and mixed thoroughly. 1 mL of inoculated water mixture was serial diluted in PBDW. 10 mL of the inoculated water mixture was dispensed into 2 individual test tubes, where the appropriate volume of the EnviroSan 1 stock solution with catalase was added to achieve 30 ppm or 40 ppm POAA to each test tube in timed intervals and mixed. The methods of Example 5 were employed to make the EnviroSan with catalase stock solutions. Then neutralized 1 mL samples in 9 mL of 0.5% sodium thiosulfate were obtained after 2.5 minutes, as well as 5 minutes. Results: Table 7 shows the summary of aerobic bacterial population (CFU/mL) present in water sample mixtures before and after inoculation with a *P. aeruginosa* culture, as well as survivors present 2.5 minutes and 5 minutes after the addition of 30 ppm or 40 ppm POAA+catalase. In addition, the bottom portion of the table summarizes data for the treatment of inoculated fresh water with 30 ppm and 40 ppm POAA alone as a comparison to those pre-reduced with catalase.

TABLE 7

| Water Sample Type | Test Substance | Exposure Time | CFU/mL | Log₁₀ Growth | Av. Log₁₀ Growth | Log₁₀ Reduction |
|---|---|---|---|---|---|---|
| Fresh Pond Water | | Before Inoculation | 1.02E+03 | 3.01 | 3.01 | |
| | | After Inoculation | 1.01E+08 | 8.00 | 8.00 | |
| | EnviroSan 30 ppm | 2.5 minutes | 3.80E+04 1.10E+04 | 4.58 4.04 | 4.31 | 3.69 |

TABLE 7-continued

| Water Sample Type | Test Substance | Exposure Time | CFU/mL | Log$_{10}$ Growth | Av. Log$_{10}$ Growth | Log$_{10}$ Reduction |
|---|---|---|---|---|---|---|
| | POAA + Catalase | 5 minutes | 2.04E+03<br>4.00E+01 | 3.31<br>1.60 | 2.46 | 5.55 |
| | EnviroSan 40 ppm | 2.5 minutes | 1.00E+04<br>1.15E+05 | 4.00<br>5.06 | 4.53 | 3.47 |
| | POAA + Catalase | 5 minutes | 2.00E+01<br>1.00E+01 | 1.30<br>1.00 | 1.15 | 6.85 |
| 90 Fresh/ 10 Produced | | Before Inoculation | 1.10E+05 | 5.04 | 5.04 | |
| | | After Inoculation | 9.90E+07 | 8.00 | 8.00 | |
| | EnviroSan 30 ppm | 2.5 minutes | 6.00E+03<br>5.00E+01 | 3.78<br>1.70 | 2.74 | 5.26 |
| | POAA + Catalase | 5 minutes | 1.00E+01<br>2.50E+02 | 1.00<br>2.40 | 1.70 | 6.30 |
| | EnviroSan 40 ppm | 2.5 minutes | 1.37E+03<br>4.90E+02 | 3.14<br>2.69 | 2.91 | 5.08 |
| | POAA + Catalase | 5 minutes | 6.00E+01<br>6.00E+01 | 1.78<br>1.78 | 1.78 | 6.22 |
| 80 Fresh/20 minutes Produced | | Before Inoculation | 1.80E+05 | 5.26 | 5.26 | |
| | | After Inoculation | 8.50E+07 | 7.93 | 7.93 | |
| | EnviroSan 30 ppm | 2.5 minutes | 4.00E+02<br>7.00E+01 | 2.60<br>1.85 | 2.22 | 5.71 |
| | POAA + Catalase | 5 minutes | 2.60E+02<br>1.00E+01 | 2.41<br>1.00 | 1.71 | 6.22 |
| | EnviroSan 40 ppm | 2.5 minutes | 1.00E+01<br>5.00E+01 | 1.00<br>1.70 | 1.35 | 6.58 |
| | POAA + Catalase | 5 minutes | 6.00E+01<br>1.00E+01 | 1.78<br>1.00 | 1.39 | 6.54 |
| 70 Fresh/ 30 Produced | | Before Inoculation | 2.30E+05 | 5.36 | 5.36 | |
| | | After Inoculation | 9.50E+07 | 7.98 | 7.98 | |
| | EnviroSan 30 ppm | 2.5 minutes | 1.00E+01<br>1.00E+01 | 1.00<br><1.00 | 1.00 | 6.98 |
| | POAA + Catalase | 5 minutes | 1.00E+01<br>1.00E+01 | <1.00<br><1.00 | <1.00 | >6.98 |
| | EnviroSan 40 ppm | 2.5 minutes | 1.00E+01<br>1.00E+01 | 1.00<br>1.00 | 1.00 | 6.98 |
| | POAA + Catalase | 5 minutes | 2.00E+01<br>3.00E+01 | 1.30<br>1.48 | 1.39 | 6.59 |
| Fresh Pond Water | | Before Inoculation | 1.02E+03 | 3.01 | 3.01 | |
| | | After Inoculation | 1.01E+08 | 8.00 | 8.00 | |
| | EnviroSan 30 ppm | 2.5 minutes | 2.35E+03<br>2.10E+04 | 3.37<br>4.32 | 3.85 | 4.16 |
| | POAA | 5 minutes | 8.00E+01<br>9.00E+01 | 1.90<br>1.95 | 1.93 | 6.08 |
| | EnviroSan 40 ppm | 2.5 minutes | 2.00E+04<br>4.32E+03 | 4.30<br>3.64 | 3.97 | 4.04 |
| | POAA | 5 minutes | 1.20E+02<br>3.00E+01 | 2.08<br>1.48 | 1.78 | 6.23 |

Titration data showing POAA consumption was also analyzed and shown in Table 8. The titration data indicates the addition of catalase to the EnviroSan test substance significantly lowers the degradation rate of POAA within the water mixture over 5 minutes as compared to equivalent dosing of chemistry not pre-reduced with catalase.

TABLE 8

| Water Mixture | Desired Concentration | Actual Titrated Concentration (ppm POAA) | |
|---|---|---|---|
| | | 1 minute | 5 minutes |
| 100% Fresh | 30 ppm POAA + Catalase | 25 ppm | 27 ppm |
| | 40 ppm POAA + Catalase | 35 ppm | 36 ppm |
| 90% Fresh/10% Produced | 30 ppm POAA + Catalase | 26 ppm | 27 ppm |
| | 40 ppm POAA + Catalase | 34 ppm | 36 ppm |
| | 30 ppm POAA | 21 ppm | 8 ppm |
| | 40 ppm POAA | 30 ppm | 16 ppm |
| 80% Fresh/20% Produced | 30 ppm POAA + Catalase | 23 ppm | 24 ppm |

TABLE 8-continued

| Water Mixture | Desired Concentration | Actual Titrated Concentration (ppm POAA) | |
|---|---|---|---|
| | | 1 minute | 5 minutes |
| | 40 ppm POAA + Catalase | 31 ppm | 33 ppm |
| | 30 ppm POAA | 13 ppm | 0 ppm |
| | 40 ppm POAA | 21 ppm | 2 ppm |
| 70% Fresh/30% Produced | 30 ppm POAA + Catalase | 24 ppm | 42 ppm |
| | 40 ppm POAA + Catalase | 18 ppm | 33 ppm |
| | 30 ppm POAA | 7 ppm | 0 ppm |
| | 40 ppm POAA | 12 ppm | 0 ppm |

Figure 7:
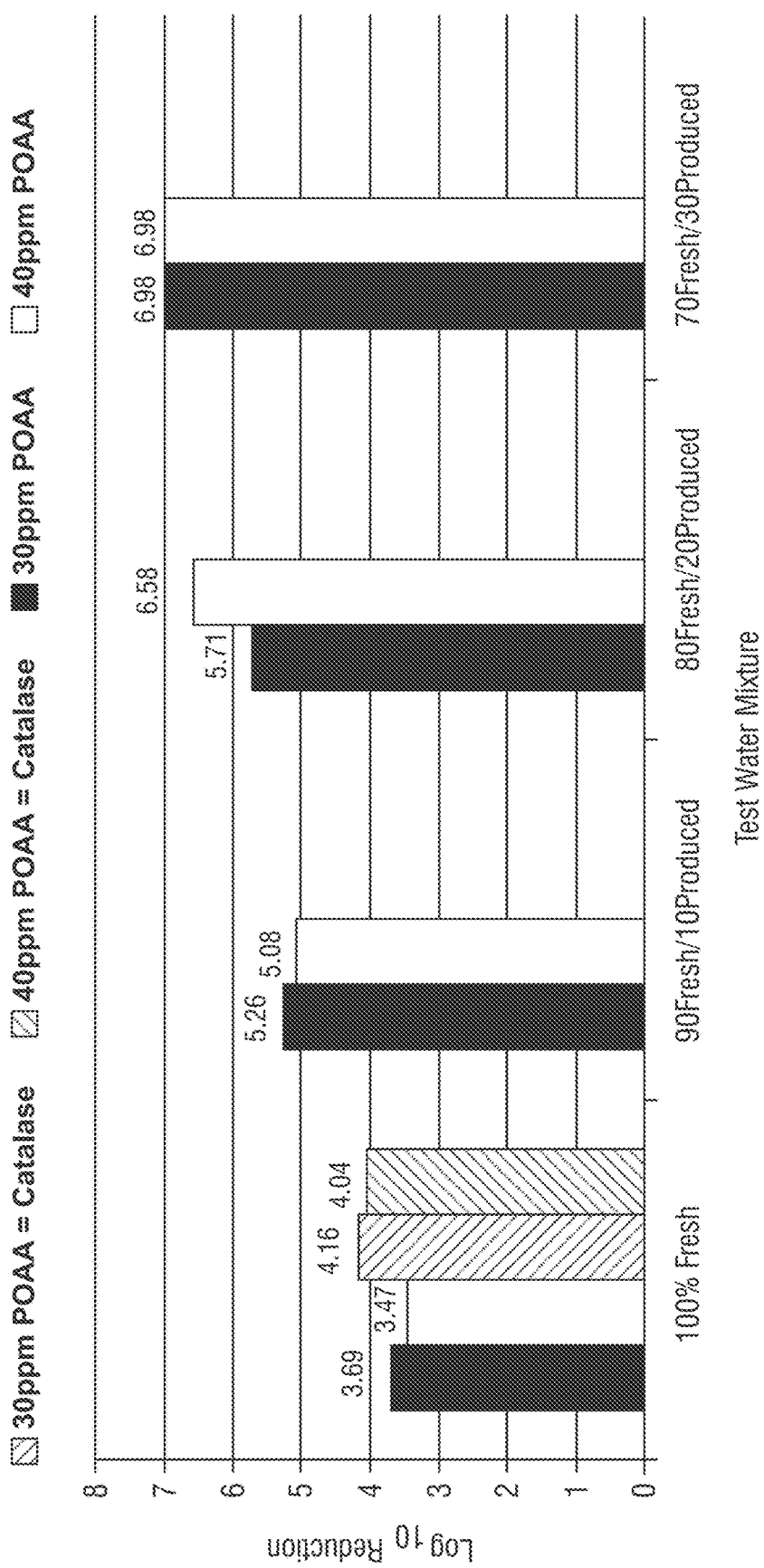
FIG. 7 shows the average log reduction generated after a 2.5 minute exposure time to 30 ppm or 40 ppm POAA EnviroSan with or without catalase in different fracking water mixtures according to embodiments of the invention.
Figure 8:
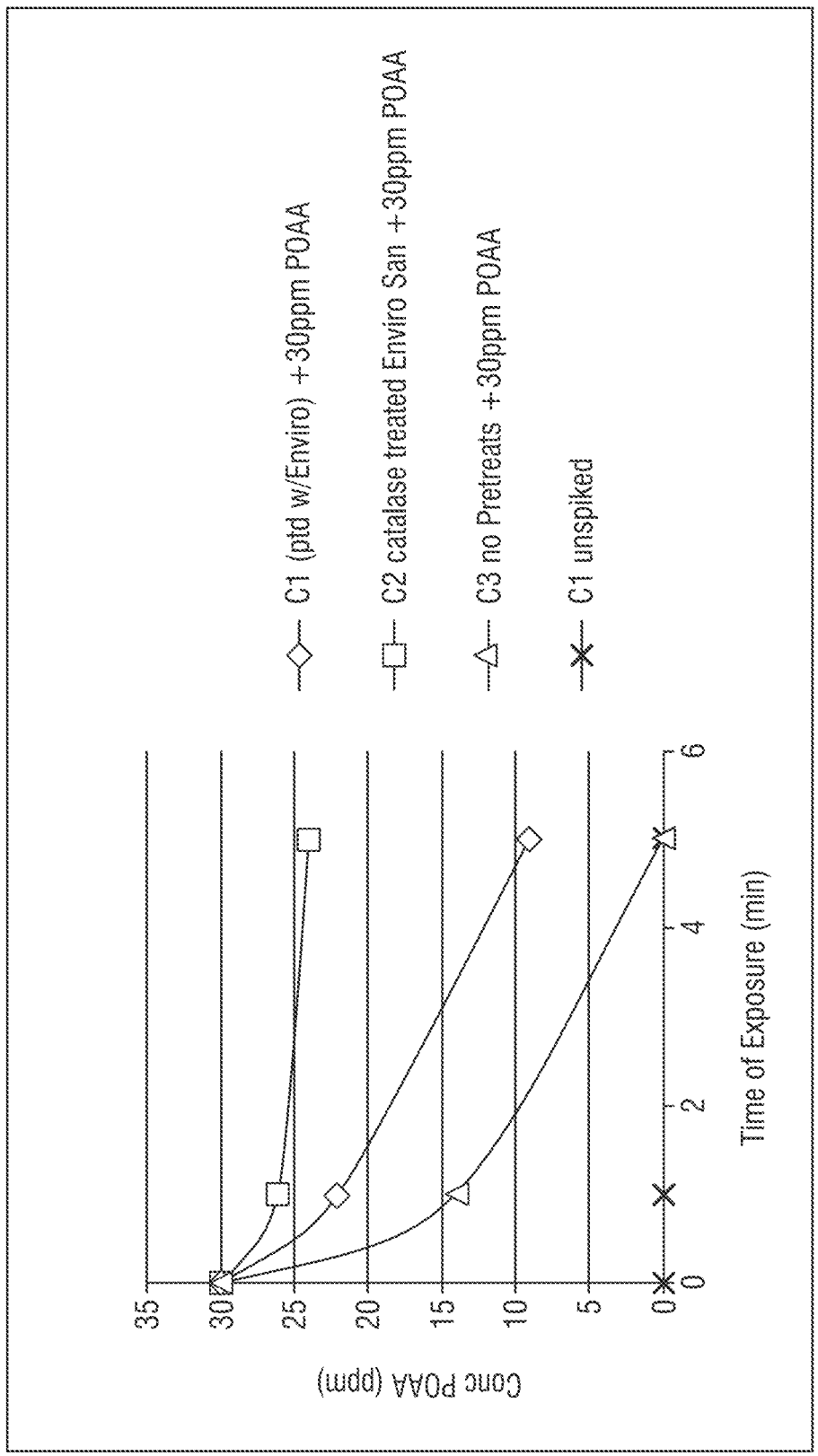
FIG. 8 shows titration data of POAA in catalase treated (and untreated) solutions of the EnviroSan test substance according to embodiments of the invention.

The average log reduction generated after a 2.5 minute exposure time to 30 ppm or 40 ppm POAA EnviroSan with or without catalase in different fracking water mixtures is shown in Table 8 and FIG. 7. The addition of catalase to the EnviroSan test substance appears to have no impact on efficacy generated against organisms present in the inoculated fresh water samples. The data also suggests that with increasing amounts of produced water within the tested water mixture, there is increased efficacy generated within the 2.5 and 5 minute exposure times when treated with EnviroSan pre-reduced with catalase.

Example 7

Additional micro efficacy performance was evaluated to confirm the improved micro efficacy observed in Example 6 when using increasing amounts of produced water with the dosing static initial concentrations of POAA (30 ppm or 40 ppm) with catalase. Improved micro efficacy with increased amounts of produced water present in a mixture is a highly counterintuitive result and was unexpected. Under normal conditions, it would be expected to have decreased micro efficacy as the amount of produced water (e.g. recycled) increases and the amount of POAA remains static as a result of the increased contamination found in produced water as opposed to fresh water sources. As a result, subsequent evaluation observed the activity of the water itself against a spiked culture of *P. aeruginosa* over a 1 hour exposure period to determine whether the produced water itself has an antimicrobial present.

All water mixtures were treated with an initial concentration of 30 ppm POAA EnviroSan, both with and without the addition of catalase. The data set evaluates whether there is a significant difference in micro activity generated between treatments of EnviroSan alone vs. EnviroSan pre-reduced with catalase.

All ratios of fracking water mixtures tested (100/0, 90/10, 80/20 & 70/30) were freshly mixed solutions, as well as solutions mixed and pretreated with 500 ppm EnviroSan product more than 1 hour before the start of the micro evaluation, in order to observe if a pretreatment step is of value for micro performance compared to those mixtures not pretreated. The test system (*P. aeruginosa* and natural water) described in Example 5 was again utilized. Water mixtures as outlined in Table 9 were provided (showing the percentage of 100 mL of each water sample type).

TABLE 9

| Water Type | A | B | C* | D | E* | F | G* |
|---|---|---|---|---|---|---|---|
| Fresh | 100% | 90% | 90% | 80% | 80% | 70% | 70% |
| Produced | | 10% | 10% | 20% | 20% | 30% | 30% |

*Solutions pretreated with 500 ppm EnviroSan more than 1 hour before micro evaluation.

The testing methods of Example 5 were utilized for the chemically treated water samples, differing only in the combination of the 10 mL inoculated water mixtures with appropriate volumes of the EnviroSan with or without catalase to achieve 30 ppm POAA residual to each test tube in timed intervals and mixed. The methods of Example 5 were employed to make the EnviroSan with catalase stock solutions. In comparison, for the water samples that were not chemically treated, 9.9 mL of test water mixture was dispensed into 2 individual test tubes. 0.10 mL of an approximate $10^8$ CFU/mL culture of *P. aeruginosa* was added in timed intervals and mixed thoroughly. Then 1 mL samples were neutralized in 9 mL of 0.5% sodium thiosulfate, followed by serial dilution and enumeration after 2.5 minutes, 5 minutes and 60 minute exposure times.

Table 10 shows a summary of aerobic bacterial population (CFU/mL) present in the water sample mixtures (both not pretreated and pretreated with 500 ppm EnviroSan) before and after inoculation with a *P. aeruginosa* culture, as well as survivors present 2.5 minutes and 5 minutes after the addition of 30 ppm POAA with or without catalase. In addition, data for enumeration of water samples for antimicrobial activity against *P. aeruginosa* over 60 minutes exposure are also summarized in Table 10.

TABLE 10

| Water Sample Type | Test Substance | Exposure Time | CFU/mL | $Log_{10}$ Growth | Av. $Log_{10}$ Growth | $Log_{10}$ Reduction |
|---|---|---|---|---|---|---|
| *Pseudomonas aeruginosa* ATCC 15442 | | | | | | |
| Fresh Pond Water | | Before Inoculation | 3.10E+04 | 4.49 | 4.49 | |
| | | After Inoculation | 7.30E+07 | 7.86 | 7.92 | |
| | | | 9.50E+07 | 7.98 | | |
| | EnviroSan 30 ppm POAA + Catalase | 2.5 minutes | 1.99E+03 | 3.30 | 3.30 | 4.62 |
| | | 5 minutes | 5.00E+01 | 1.70 | 1.70 | 6.22 |
| | EnviroSan 30 ppm POAA | 2.5 minutes | 1.90E+03 | 3.28 | 3.28 | 4.64 |
| | | 5 minutes | 4.40E+01 | 1.64 | 1.64 | 6.28 |
| | No Chemical Treatment | 2.5 minutes | 5.24E+07 | 7.72 | 7.72 | 0.20 |
| | | 5 minutes | 4.28E+07 | 7.63 | 7.63 | 0.29 |
| | | 60 minutes | 5.64E+07 | 7.75 | 7.75 | 0.17 |

TABLE 10-continued

| Water Sample Type | Test Substance | Exposure Time | CFU/mL | Log$_{10}$ Growth | Av. Log$_{10}$ Growth | Log$_{10}$ Reduction |
|---|---|---|---|---|---|---|
| 90 Fresh/ 10 Produced | | Before Inoculation | 1.22E+04 | 4.09 | 4.09 | |
| | | After Inoculation | 7.10E+07 | 7.85 | 7.80 | |
| | | | 5.70E+07 | 7.76 | | |
| | EnviroSan | 2.5 minutes | 3.30E+02 | 2.52 | 2.52 | 5.29 |
| | 30 ppm POAA + Catalase | 5 minutes | 7.00E+01 | 1.85 | 1.85 | 5.96 |
| | EnviroSan | 2.5 minutes | 5.30E+04 | 4.72 | 4.72 | 3.08 |
| | 30 ppm POAA | 5 minutes | 8.00E+03 | 3.90 | 3.90 | 3.90 |
| | No Chemical | 2.5 minutes | 5.56E+07 | 7.75 | 7.75 | 0.06 |
| | Treatment | 5 minutes | 5.04E+07 | 7.70 | 7.70 | 0.10 |
| | | 60 minutes | 5.24E+07 | 7.72 | 7.72 | 0.08 |
| 90 Fresh/ 10 Produced Pretreated with 500 ppm EnviroSan | | Before Inoculation | 1.20E+01 | 1.08 | 1.08 | |
| | | After Inoculation | 6.70E+07 | 7.83 | 7.85 | |
| | | | 7.60E+07 | 7.88 | | |
| | EnviroSan | 2.5 minutes | 6.00E+01 | 1.78 | 1.78 | 6.08 |
| | 30 ppm POAA + Catalase | 5 minutes | 5.00E+01 | 1.70 | 1.70 | 6.15 |
| | EnviroSan | 2.5 minutes | 6.00E+01 | 1.78 | 1.78 | 6.08 |
| | 30 ppm POAA | 5 minutes | 3.00E+01 | 1.48 | 1.48 | 6.38 |
| 80 Fresh/ 20 Produced | | Before Inoculation | 1.39E+04 | 4.14 | 4.14 | |
| | | After Inoculation | 6.50E+07 | 7.81 | 7.84 | |
| | | | 7.20E+07 | 7.86 | | |
| | EnviroSan | 2.5 minutes | 1.30E+02 | 2.11 | 2.11 | 5.72 |
| | 30 ppm POAA + Catalase | 5 minutes | 3.00E+01 | 1.48 | 1.48 | 6.36 |
| | EnviroSan | 2.5 minutes | 4.48E+05 | 5.65 | 5.65 | 2.18 |
| | 30 ppm POAA | 5 minutes | 2.86E+05 | 5.46 | 5.46 | 2.38 |
| | No Chemical | 2.5 minutes | 5.00E+07 | 7.70 | 7.70 | 0.14 |
| | Treatment | 5 minutes | 5.32E+07 | 7.73 | 7.73 | 0.11 |
| | | 60 minutes | 4.64E+07 | 7.67 | 7.67 | 0.17 |
| 80 Fresh/ 20 Produced Pretreated with 500 ppm EnviroSan | | Before Inoculation | 2.50E+01 | 1.40 | 1.40 | |
| | | After Inoculation | 5.70E+07 | 7.76 | 7.82 | |
| | | | 7.70E+07 | 7.89 | | |
| | EnviroSan | 2.5 minutes | 5.00E+01 | 1.70 | 1.70 | 6.12 |
| | 30 ppm POAA + Catalase | 5 minutes | 4.00E+01 | 1.60 | 1.60 | 6.22 |
| | EnviroSan | 2.5 minutes | 1.50E+03 | 3.18 | 3.18 | 4.65 |
| | 30 ppm POAA | 5 minutes | 6.00E+01 | 1.78 | 1.78 | 6.04 |
| 70 Fresh/ 30 Produced | | Before Inoculation | 1.61E+04 | 4.21 | 4.21 | |
| | | After Inoculation | 6.70E+07 | 7.83 | 7.83 | |
| | | | 6.90E+07 | 7.84 | | |
| | EnviroSan | 2.5 minutes | 3.40E+02 | 2.53 | 2.53 | 5.30 |
| | 30 ppm POAA + Catalase | 5 minutes | 7.00E+01 | 1.85 | 1.85 | 5.99 |
| | EnviroSan | 2.5 minutes | 9.00E+05 | 5.95 | 5.95 | 1.88 |
| | 30 ppm POAA | 5 minutes | 8.00E+05 | 5.90 | 5.90 | 1.93 |
| | No Chemical | 2.5 minutes | 5.48E+07 | 7.74 | 7.74 | 0.09 |
| | Treatment | 5 minutes | 4.56E+07 | 7.66 | 7.66 | 0.17 |
| | | 60 minutes | 4.72E+07 | 7.67 | 7.67 | 0.16 |
| 70 Fresh/ 30 Produced Pretreated with 500 ppm EnviroSan | | Before Inoculation | 4.10E+01 | 1.61 | 1.61 | |
| | | After Inoculation | 6.40E+07 | 7.81 | 7.82 | |
| | | | 6.90E+07 | 7.84 | | |
| | EnviroSan | 2.5 minutes | 9.60E+02 | 2.98 | 2.98 | 4.84 |
| | 30 ppm POAA + Catalase | 5 minutes | 7.50E+02 | 2.88 | 2.88 | 4.95 |
| | EnviroSan | 2.5 minutes | 1.30E+04 | 4.11 | 4.11 | 3.71 |
| | 30 ppm POAA | 5 minutes | 5.64E+03 | 3.75 | 3.75 | 4.07 |
| Sterile DI Water | No Chemical Treatment | 2.5 minutes | 5.52E+07 | 7.74 | 7.74 | |
| | | 5 minutes | 5.84E+07 | 7.77 | 7.77 | |
| | | 60 minutes | 5.16E+07 | 7.71 | 7.71 | |

The water sample mixtures according to this study are summarized in Tables 11A-B, showing the water sample mixtures and chemical treatments (Table 10A) and the titrated concentrations of POAA (Table 11B).

TABLE 11A

| Water Sample Mixture | | Treatment |
|---|---|---|
| C1 | 80/20 Pretreated with 500 ppm EnviroSan ≥ 1 hour before study | 30 ppm POAA EnviroSan |
| C2 | 80/20 | 30 ppm POAA EnviroSan + Catalase |
| C3 | 80/20 | 30 ppm POAA EnviroSan |
| C4 | 80/20 | No Chemical Treatment |

TABLE 11B

| | Titrated Concentration (ppm POAA) | | |
|---|---|---|---|
| Test Solution | 0 minutes | 1 minute | 5 minutes |
| C1 | 30 ppm | 22 ppm | 9 ppm |
| C2 | 30 ppm | 26 ppm | 24 ppm |
| C3 | 30 ppm | 14 ppm | 0 ppm |
| C4 | 0 ppm | 0 ppm | 0 ppm |

The titration data confirms that the addition of catalase to the EnviroSan test substance significantly lowers the degradation rate of POAA within the water mixture over 5 minutes as compared to equivalent dosing of chemistry not pre-reduced with catalase. In addition, water pretreated with $H_2O_2$ 1 hour prior to testing slightly reduces POAA degradation, as well, however not nearly as significantly as using pre-reduced EnviroSan by catalase as the test substance.

Table 11C show the use of 30 ppm POAA with/without catalase treatment compared for micro performance at both 2.5 and 5.0 minutes exposure times. Upon addition of 10-30% reuse water a defined drop in antimicrobial performance was observed over both 2.5 and 5 minutes as peracid was rapidly consumed if not pretreated with catalase. A residual of 30 ppm POAA at 5 minutes was needed to achieve the desired antimicrobial performance.

TABLE 11C

| Holding Tank Pretreatment | Percentage Reuse $H_2O$ | Slick Water Treatment | | Avg. $Log_{10}$ Reduction | |
|---|---|---|---|---|---|
| | | | | 2.5 minutes | 5 minutes |
| None | 0% | 30 ppm PAA | Catalase | 4.62 | 6.22 |
| | | | NO Catalase | 4.64 | 6.32 |
| None | 10% | 30 ppm PAA | Catalase | 5.29 | 5.96 |
| | | | NO Catalase | 3.09 | 3.91 |
| None | 20% | 30 ppm PAA | Catalase | 5.73 | 6.36 |
| | | | NO Catalase | 2.19 | 2.38 |
| None | 30% | 30 ppm PAA | Catalase | 5.30 | 5.98 |
| | | | NO Catalase | 1.88 | 1.93 |

Figure 9:
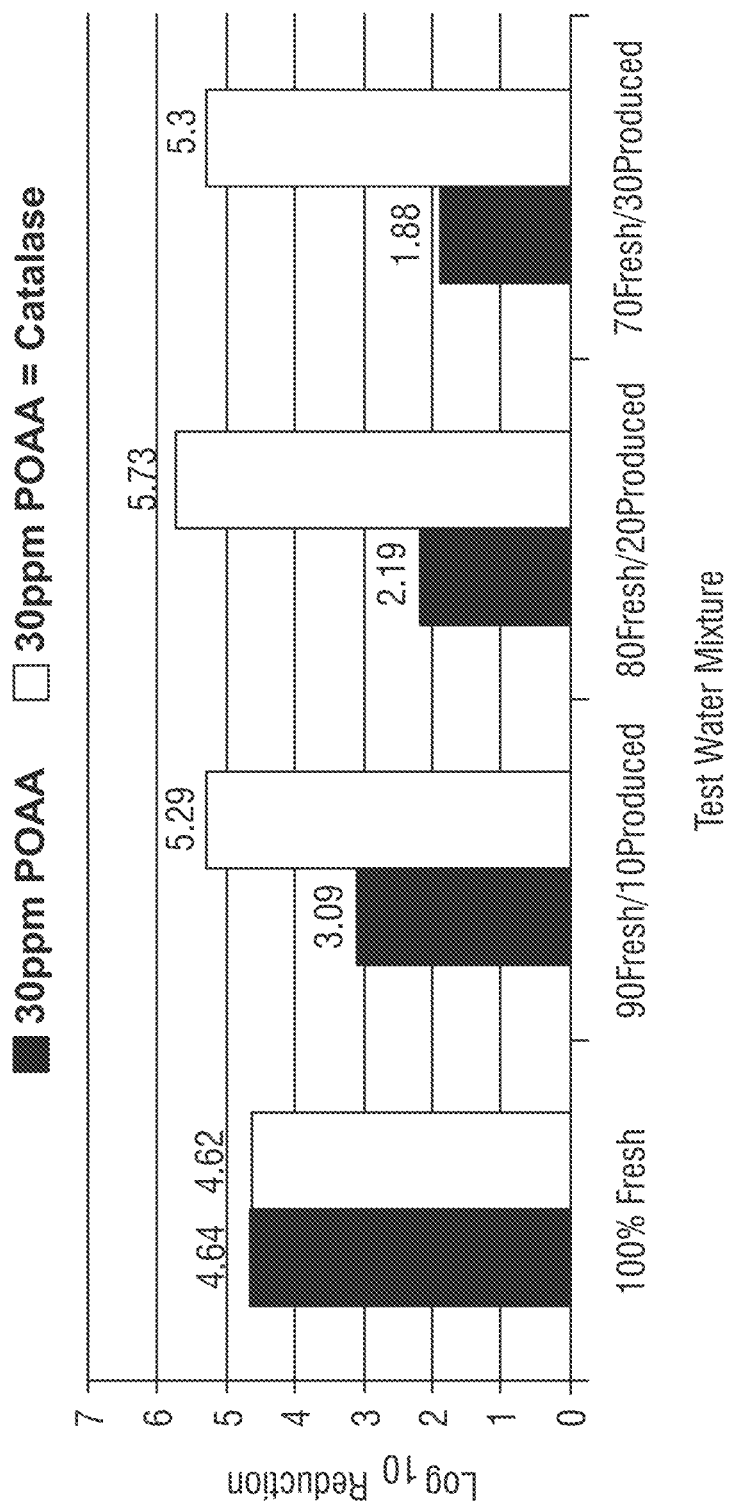
FIG. 9 shows the average log reduction generated after a 2.5 minute exposure time to 30 ppm POAA EnviroSan with or without catalase pretreatment in different fracking water mixtures according to the invention.
Figure 10:
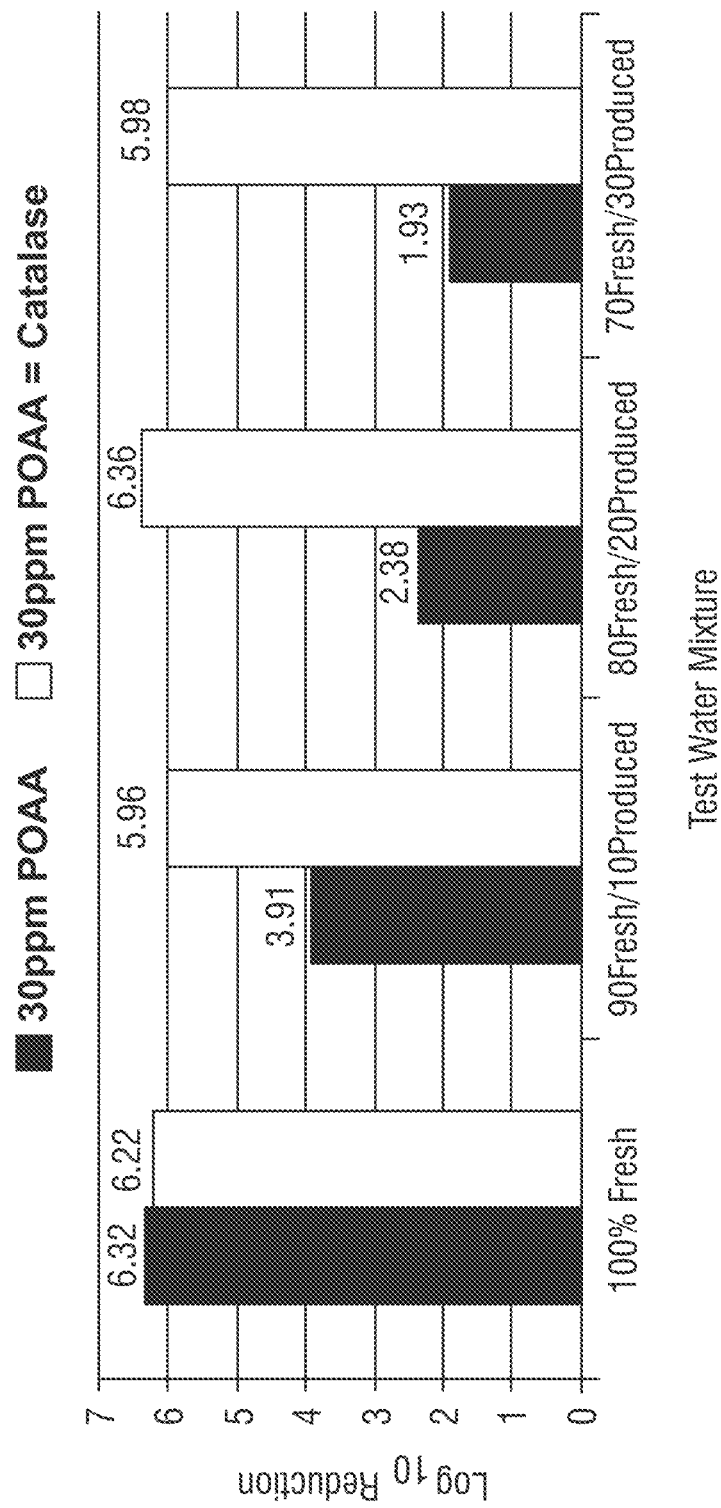
FIG. 10 shows the average log reduction generated after a 5 minute exposure time to 30 ppm POAA EnviroSan with or without catalase pretreatment in different fracking water mixtures according to the invention.

Data showed that in the absence of reuse water (contaminated water) at 30 ppm POAA with/without catalase treatment both achieved desired antimicrobial performance. FIGS. 9 and 10 confirm the findings of no difference in micro efficacy between fresh water samples treated with 30 ppm POAA alone vs. 30 ppm POAA+catalase at 2.5 minutes (FIG. 9) and 5 minutes (FIG. 10). It is thought that the use of fresh water does not interfere with the stability of the POAA and therefore the micro efficacy of the POAA in solution of fresh waters.

Figure 11:
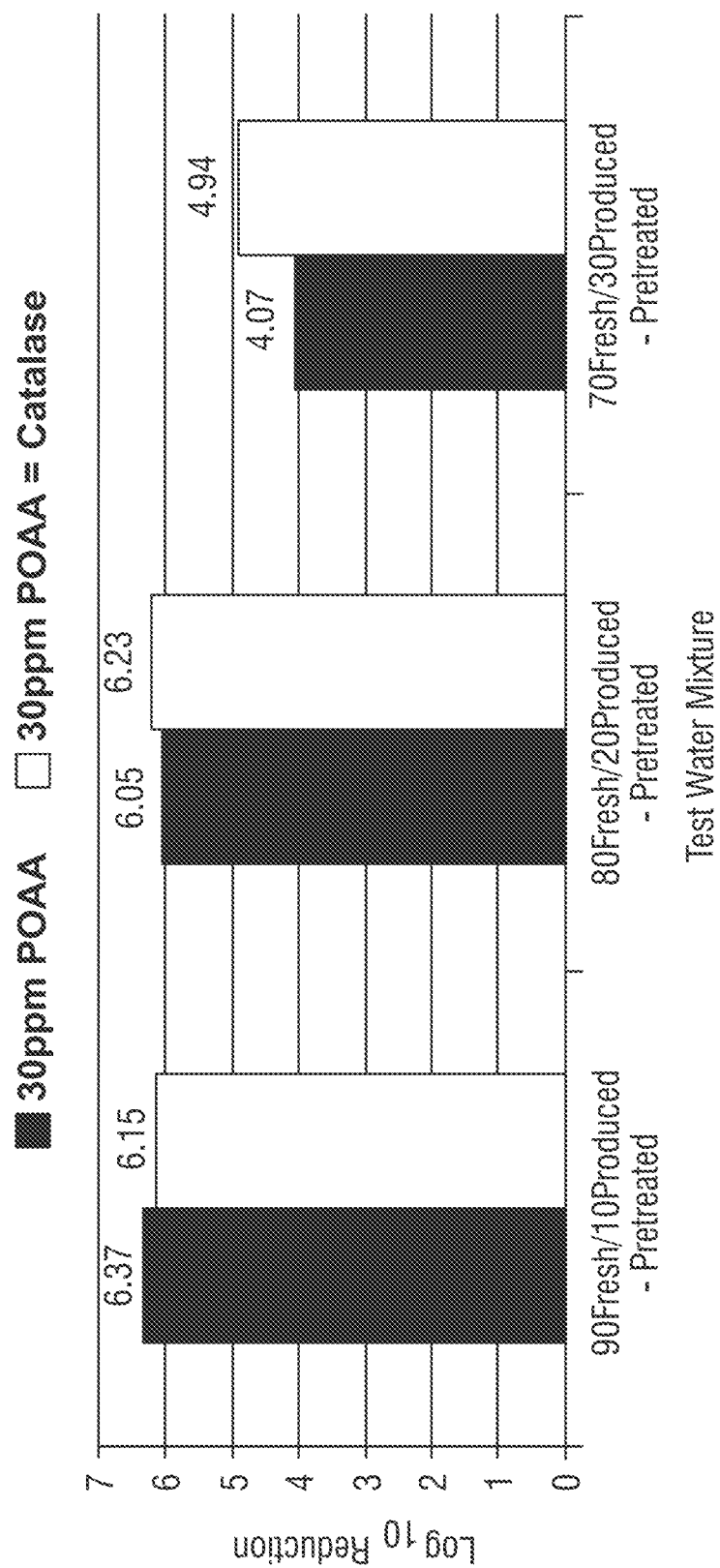
FIG. 11 shows the average log reduction generated after a 5 minute exposure time to 30 ppm POAA EnviroSan with or without catalase in different fracking water mixtures that were pretreated with 500 ppm EnviroSan product more than 1 hour before micro testing.

The data confirm there is a significant difference in activity generated by POAA vs. POAA+catalase in tested water mixtures containing produced water. On average, there was at least a 2 log greater reduction observed for samples treated with POAA+catalase, than samples treated with POAA alone at the same time point (FIG. 11). This confirms the enhanced POAA stability and concomitant micro efficacy in reuse waters with reduced hydrogen peroxide.

Figure 12:
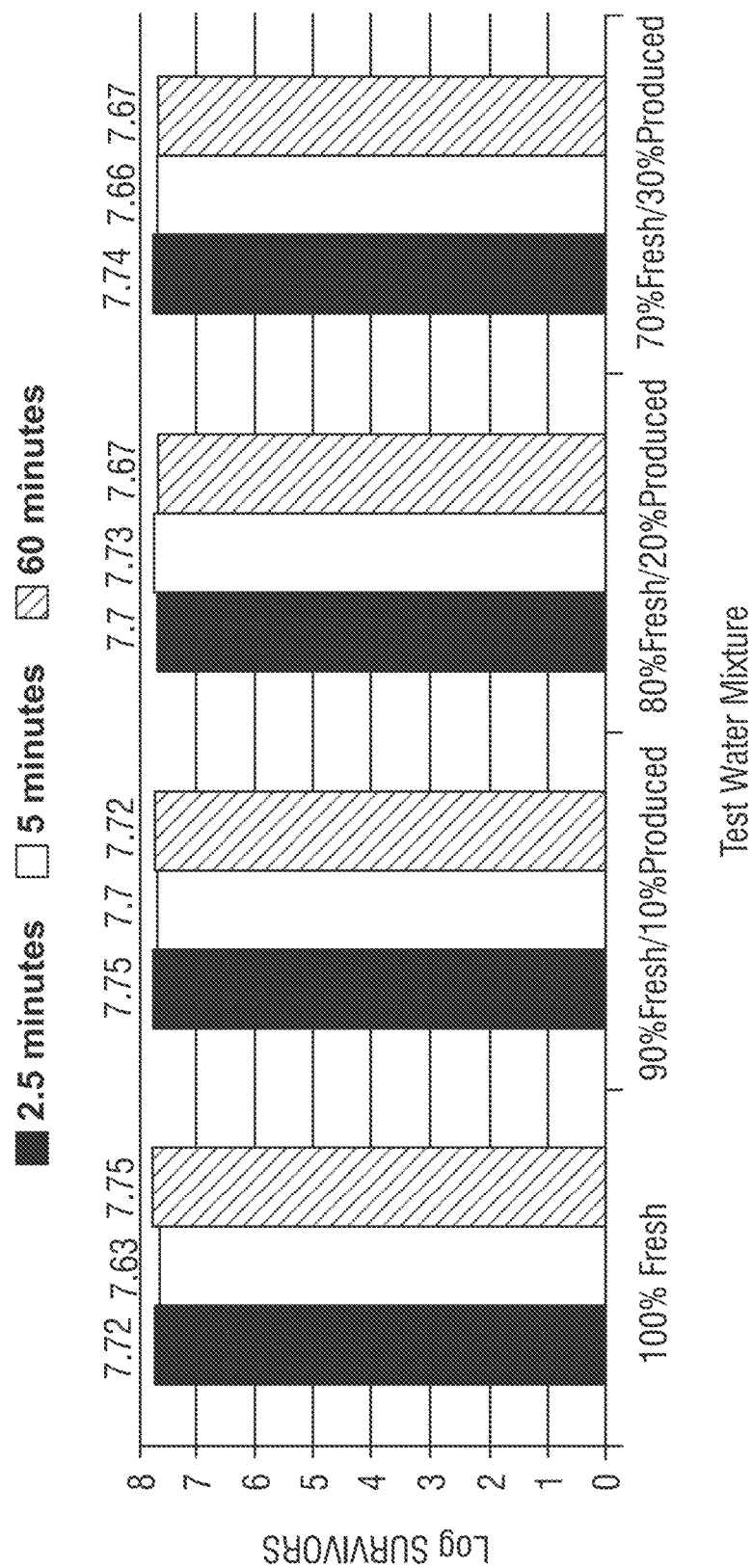
FIG. 12 shows the log survivors present 2.5, 5 and 60 minutes after the addition of a *P. aeruginosa* culture into different mixtures of fracking water according to embodiments of the invention.

However, with the pretreatment of water mixtures by 500 ppm EnviroSan more than 1 hour prior to testing, the differences in efficacy observed between POAA alone vs. POAA+catalase treatments were eliminated (FIG. 12). The log survivors present 2.5, 5 and 60 minutes after the addition of a *P. aeruginosa* culture into different mixtures of fracking water were nearly equivalent with the pretreatment of at least an hour before testing, thus confirming the water alone does not have any antimicrobial properties.

Example 8

A micro efficacy comparison of POAA added at levels to target 30 ppm POAA residuals at 5 minutes versus POAA pretreated with catalase was conducted as set forth in Table 12.

TABLE 12

| Holding Tank Treatment | Percentage Reuse $H_2O$ | Slick Water Treatment | | Avg. $Log_{10}$ Reduction | |
|---|---|---|---|---|---|
| | | | | 2.5 minutes | 5 minutes |
| None | 10% | 30 ppm PAA | Catalase | 5.29 | 5.96 |
| | | 46 ppm PAA | NO Catalase | 4.32 | 4.72 |
| None | 20% | 30 ppm PAA | Catalase | 5.73 | 6.36 |
| | | 86 ppm PAA | NO Catalase | 4.57 | 4.64 |
| None | 30% | 30 ppm PAA | Catalase | 5.30 | 5.98 |
| | | 138 ppm PAA | NO Catalase | 4.12 | 5.00 |

Figure 13:
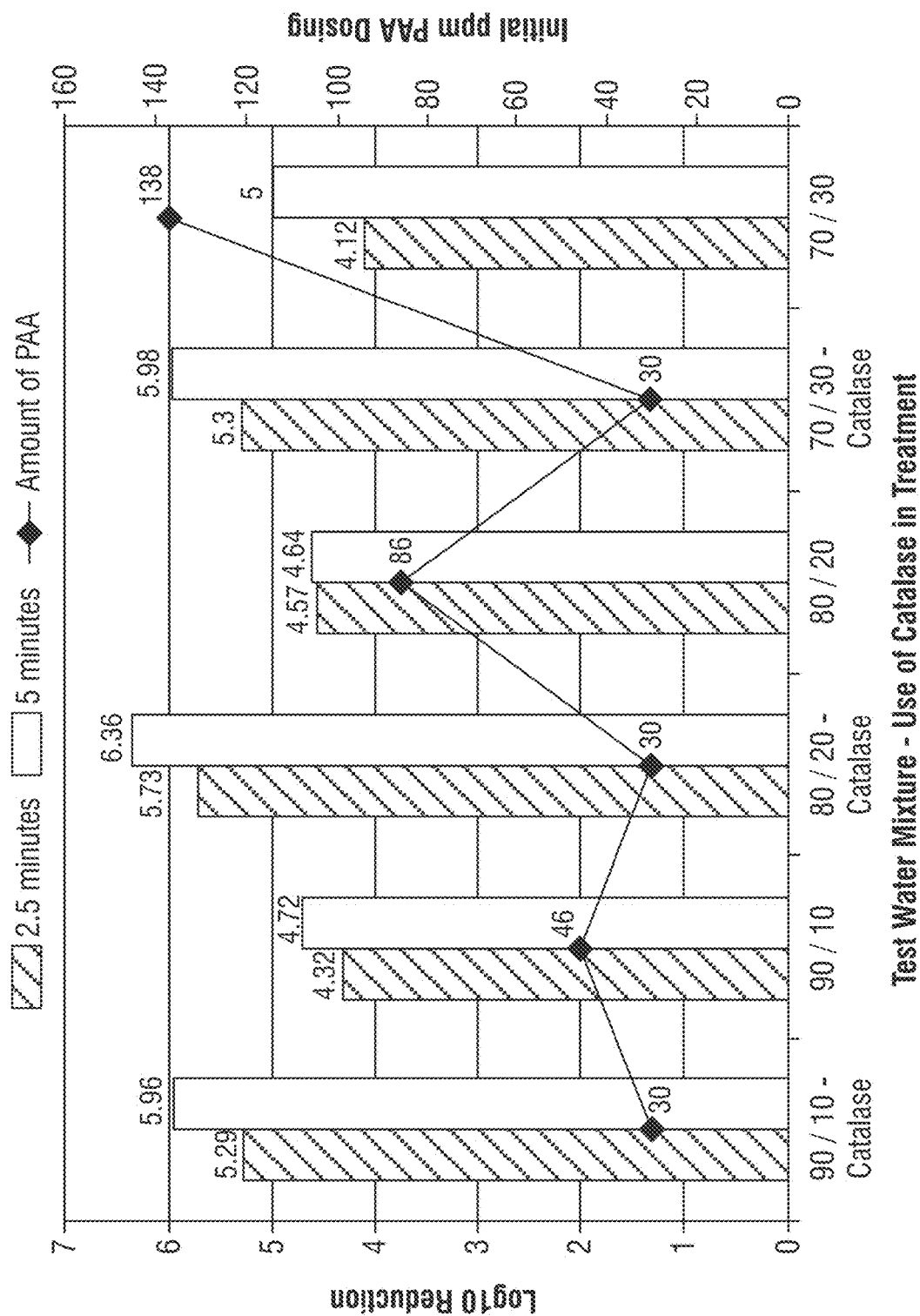
FIG. 13 shows the average log reduction generated after a 2.5 and 5 minute exposure times to 30 ppm PAA with catalase against increasing levels of PAA alone in various fracking water mixtures.

This data further confirms there is an improvement in the micro efficacy of POAA treated with catalase as opposed to POAA alone in all tested water mixtures containing at least 10% produced water. (FIG. 13). This confirms the enhanced POAA stability and concomitant micro efficacy in reuse waters with reduced hydrogen peroxide.

Example 9

Figure 14:
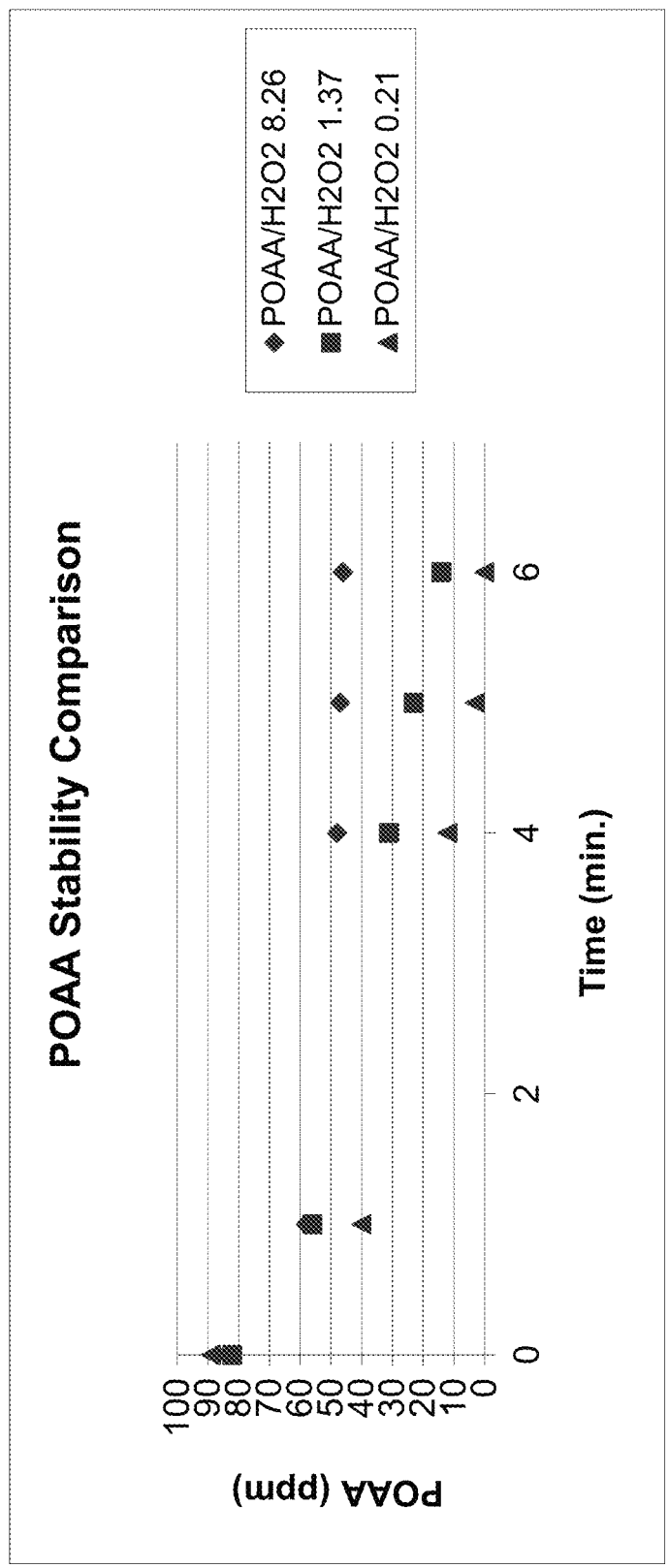
FIG. 14 shows the impact of POAA to $H_2O_2$ ratio on the stability of POAA according to embodiments of the invention.

The impact of peracid to hydrogen peroxide ratio on the stability of the peracid in produced waters was evaluated. Various commercially available peracid use solutions were employed having the peracid to hydrogen peroxide ratios set forth in Table 13. FIG. 14 shows the increased ratio of peracid to hydrogen peroxide improves peracid stability.

TABLE 13

| Time (min.) | Sample | | |
|---|---|---|---|
| | (1) POAA/$H_2O_2$ 8.26 | (2) POAA/$H_2O_2$ 1.37 | (3) POAA/$H_2O_2$ 0.21 |
| 0 | 87 | 82 | 89 |
| 1 | 58 | 56 | 40 |
| 4 | 48 | 31 | 12 |
| 5 | 47 | 23 | 3 |
| 6 | 46 | 14 | 0 |

Example 10

The effect of catalase on the peracid stability within treated waters was further evaluated. Water blends of 80/20 (80% fresh water/20% produced water) were employed to analyze the impact on various treatment sequences set forth in Table 14.

TABLE 14

| Treatment Sequence | Water Blends | Catalase RM Conc (ppm): CA 400 | Theoretical Initial POAA (ppm) | POAA Meas'd. at 1 min. (ppm) | POAA Meas'd. at 4 min. (ppm) | POAA Meas'd. at 5 min. (ppm) | POAA Meas'd. at 6 min. (ppm) | Req'd. Enviro San (14.5% POAA, ppm w/w) |
|---|---|---|---|---|---|---|---|---|
| Simult. Add | 80/20 | 100 | 82 | 66 | 61 | 65 | 58 | 566 |
| NA | 80/20 | 0 | 82 | 56 | 31 | 23 | 17 | 566 |
| Simult. Add | 80/20 | 10 | 82 | 63 | 34 | 31 | 26 | 566 |
| Pretreated | 80/20 | 10 | 82 | 76 | 75 | 75 | 75 | 566 |

Figure 15:
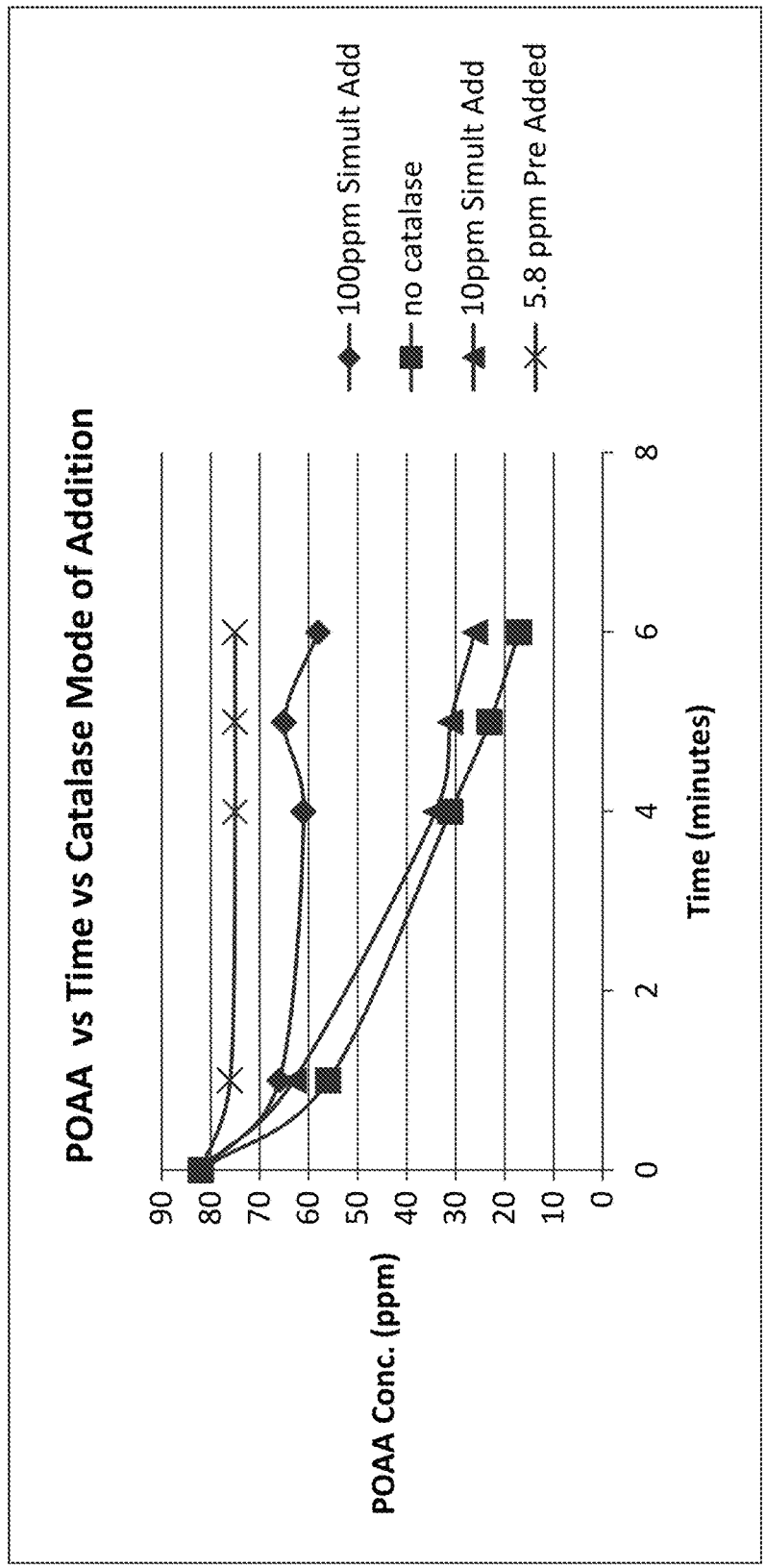
FIGS. 15-16 show the impact of catalase addition on the peracid stability within treatment waters according to the invention.

As shown in FIG. 15, the most stable peracid systems were pretreated with catalase prior to addition to the blended water sources. Use of 10× the catalase yielded inferior results in comparison to the pretreatment with catalase demonstrating a clear benefit to pretreatment according to the invention when using blended compositions. The composition not containing catalase demonstrated rapid POAA degradation.

Due to the efficacious results shown in FIG. 15, the same methods were used to further evaluate a pretreatment using a lower concentration of the catalase as shown in Table 15.

TABLE 15

| Treatment Sequence | Water Blends | Catalase RM Conc (ppm): CA 400 | Theoretical Initial POAA (ppm) | POAA Meas'd. at 1 min. (ppm) | POAA Meas'd. at 4 min. (ppm) | POAA Meas'd. at 5 min. (ppm) | POAA Meas'd. at 6 min. (ppm) |
|---|---|---|---|---|---|---|---|
| Simult. Add | 80/20 | 100 | 82 | 66 | 61 | 65 | 58 |
| NA | 80/20 | 0 | 82 | 56 | 31 | 23 | 17 |
| Simult. Add | 80/20 | 10 | 82 | 63 | 34 | 31 | 26 |
| Pretreated | 80/20 | 5.8 | 82 | 76 | 75 | 75 | 75 |

Figure 16:
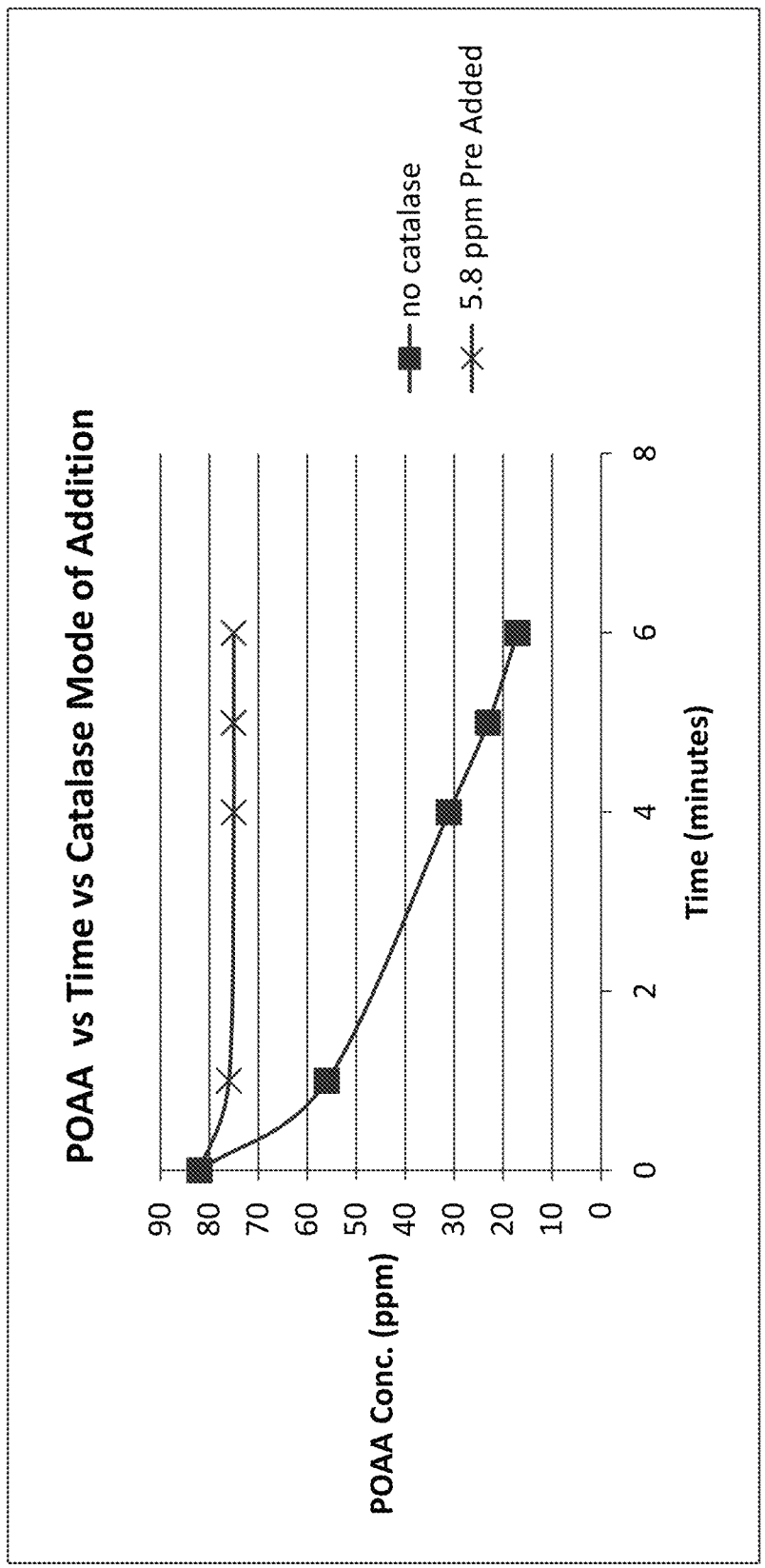

As shown in FIG. 16, the decreased catalase used in the pretreated peracid composition again outperformed the simultaneous addition of catalase to a peracid system and/or no catalase system.

Example 11

Figure 17:
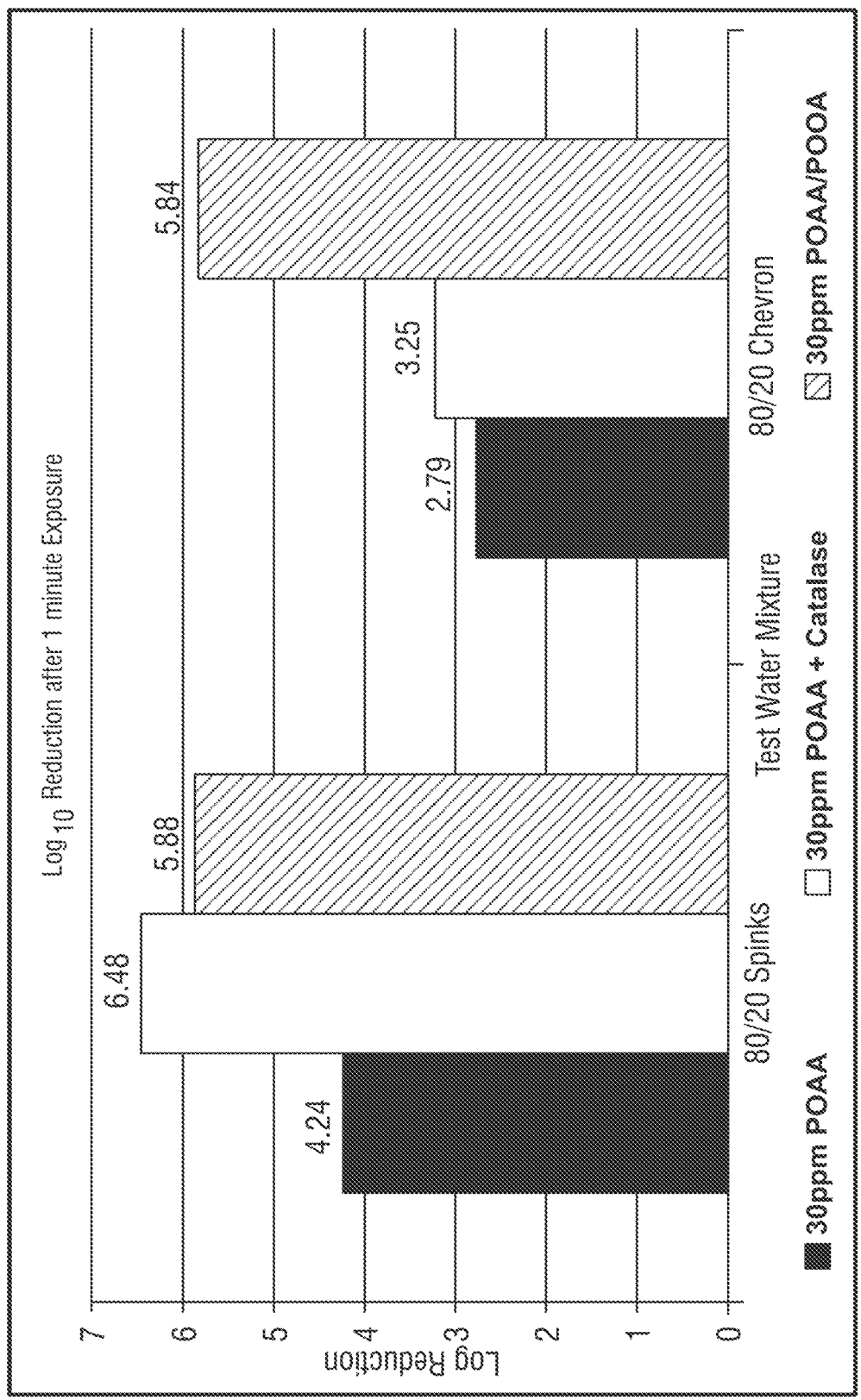
FIG. 17 shows the synergy of mixed peracid antimicrobial efficacy with blends of water sources according to embodiments of the invention.

The micro efficacy of a 30 ppm POAA (EnviroSan) composition, a 30 ppm POAA (EnviroSan) with catalase composition and a 30 ppm mixed peracetic acid and peroctanoic acid peracid composition (POAA/POOA) were compared (FIG. 17). The micro efficacy was evaluated using 80% fresh water/20% produced water system from and oil- and gas-field operation.

The mixed POAA/POOA composition demonstrated improvements over use of the 30 ppm POAA composition alone. The same ppm peracid provided significantly improved results and therefore would enable use at significantly lower dosages, demonstrating synergy in a mixed peracid composition.

Example 12

The compatibility between peracetic acid and catalase compositions and components of gel frac fluids were evaluated. The changes in viscosity of the gel fluid upon addition of peracetic acid with and without catalase were evaluated. Linear guar slurries were initially prepared by hydration of guar polymers in standard 5-speed Waring blender. Deionized water was added and the mixture was stirred until a homogeneous mixture was obtained. The linear gels were cross-linked in the presence of borate based cross-linker activators and peracetic acid with and without catalase. The viscosity of the fluids was subsequently monitored at 275° F. for 200 minutes using a Grace 5500 rheometer with a RIBS rotor-bob configuration.

Figure 18:
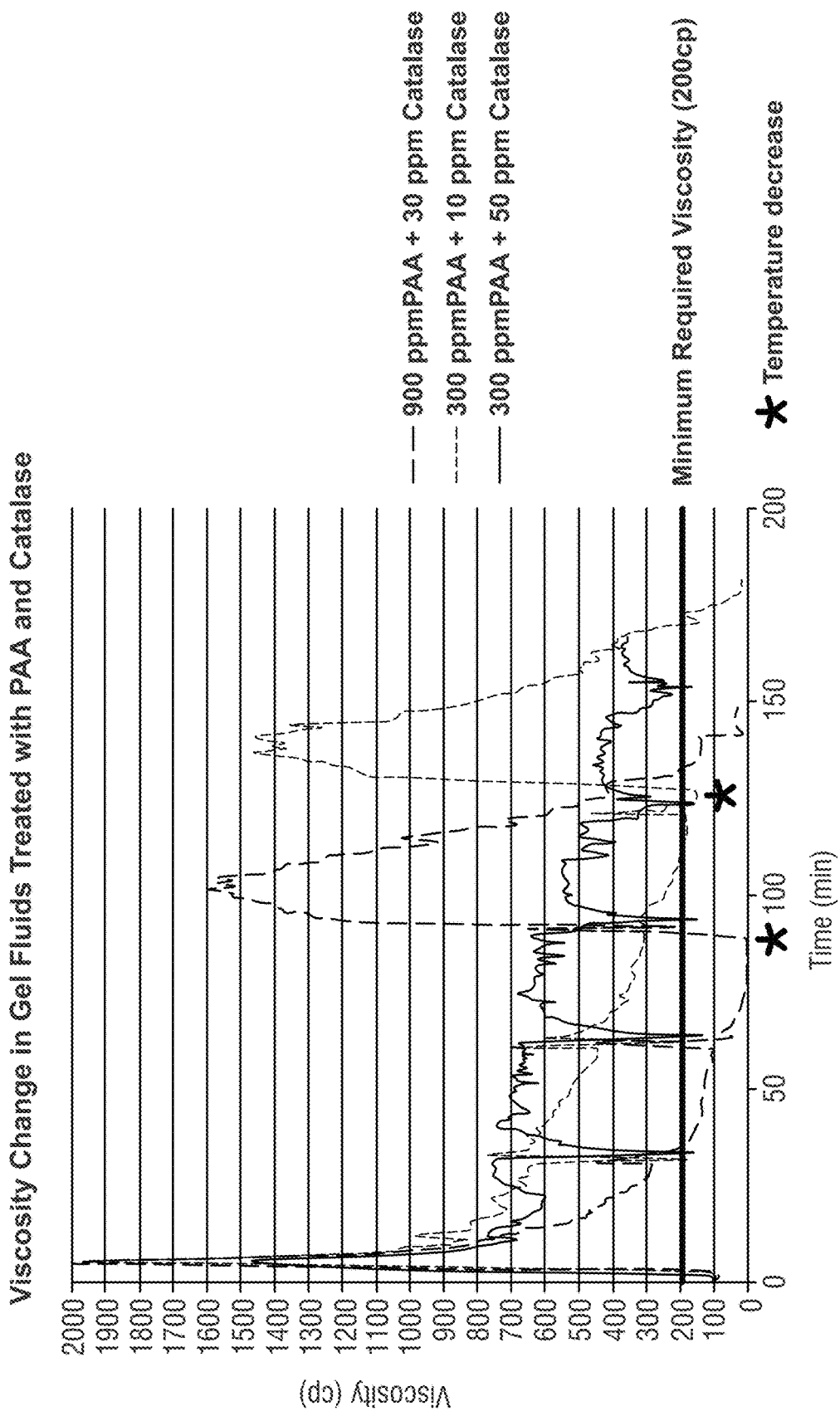
FIG. 18 shows the compatibility of peracid and catalase compositions for use in gel formation for gel frac fluids according to embodiments of the invention.

The pass/fail criteria of the test were established as the fluids maintaining a minimum viscosity of 200 cP for 120 minutes at 275° F. The results shown in FIG. 18 demonstrate that varying concentrations of peracetic acid between 1 ppm and 1000 ppm along with varying concentrations of catalase between 1 ppm and 200 ppm were tested. FIG. 18 shows that hydrogen peroxide removal is critical for the viscosity of the gel to remain above 200 cP for the required time. Excess peracetic acid and hydrogen peroxide (e.g. insufficient catalase) in a system failed to sustain the viscosity above 200 cP for the required time. Testing could not be performed with peracetic acid and hydrogen peroxide alone (i.e. without catalase or other peroxide-reducing agent) as the product prevented a gel from being formed. This is considered a fail and would not be compatible for field use.

Example 13

The concentration of peracid compositions was evaluated to determine the peroxide-reducing capability of enzymes. A catalase enzyme was evaluated for efficacy in reducing hydrogen peroxide at varying concentrations under increasingly concentrated peracid compositions. The commercially-available peracid (POAA) composition EnviroSan (Ecolab, Inc., St. Paul, Minn.) was evaluated using catalase enzymes added to 2%, 3%, and 5% peracid compositions. The catalase enzymes were added to the POAA solution and gently stirred under ambient conditions. After the addition of catalase, the stirring was discontinued, and the samples were taken for iodometric assay.

As shown in Table 16, the peroxide-reducing enzymes demonstrated efficacy in removing hydrogen peroxide from the peracid composition at peracid levels as high as 3% POAA; however no impact was observed at the level of 5% POAA.

TABLE 16

| Time (min.) | 2% POAA 1500 ppm Catalase | 3% POAA 1500 ppm Catalase | 3% POAA 2500 ppm Catalase | 5% POAA 1500 ppm Catalase |
|---|---|---|---|---|
| 0 | 2.0% POAA 1.36% H2O2 | 3.0% POAA 2.04% H2O2 | 2.0% POAA 2.04% H2O2 | 5.0% POAA 3.40% H2O2 |
| 6.5 | 2.05% POAA 0.08% H2O2 | 2.97% POAA 0.33% H2O2 | 2.99% POAA 0.33% H2O2 | 4.96% POAA 3.81% H2O2 |
| 10 | NA | 2.83% POAA 0.23% H2O2 | 2.95% POAA 0.23% H2O2 | NA |
| 15 | NA | 2.95% POAA 0.21% H2O2 | 2.87% POAA 0.21% H2O3 | NA |

Example 14

Differing processes of forming antimicrobial reduced peroxide compositions according to embodiments of the invention were evaluated to determine process effects on the peroxide-reducing capability of enzymes. A first process (A) combined a peracid composition to a solution containing catalase enzyme. To 392 grams of DI water was added 1.5 mL of ES 2000 catalase, then 107.37 grams of EnviroSan (POAA) peracid composition was slowly added to the solution during a period of 5 minutes without stirring.

A second process (B) added a catalase composition to a diluted peracid composition. To the solution of 107.37 grams of EnviroSan (POAA) peracid composition in 392 grams of DI water, 0.5 mL of ES 2000 catalase was added during a period of 5 minutes without stirring.

Figure 19:
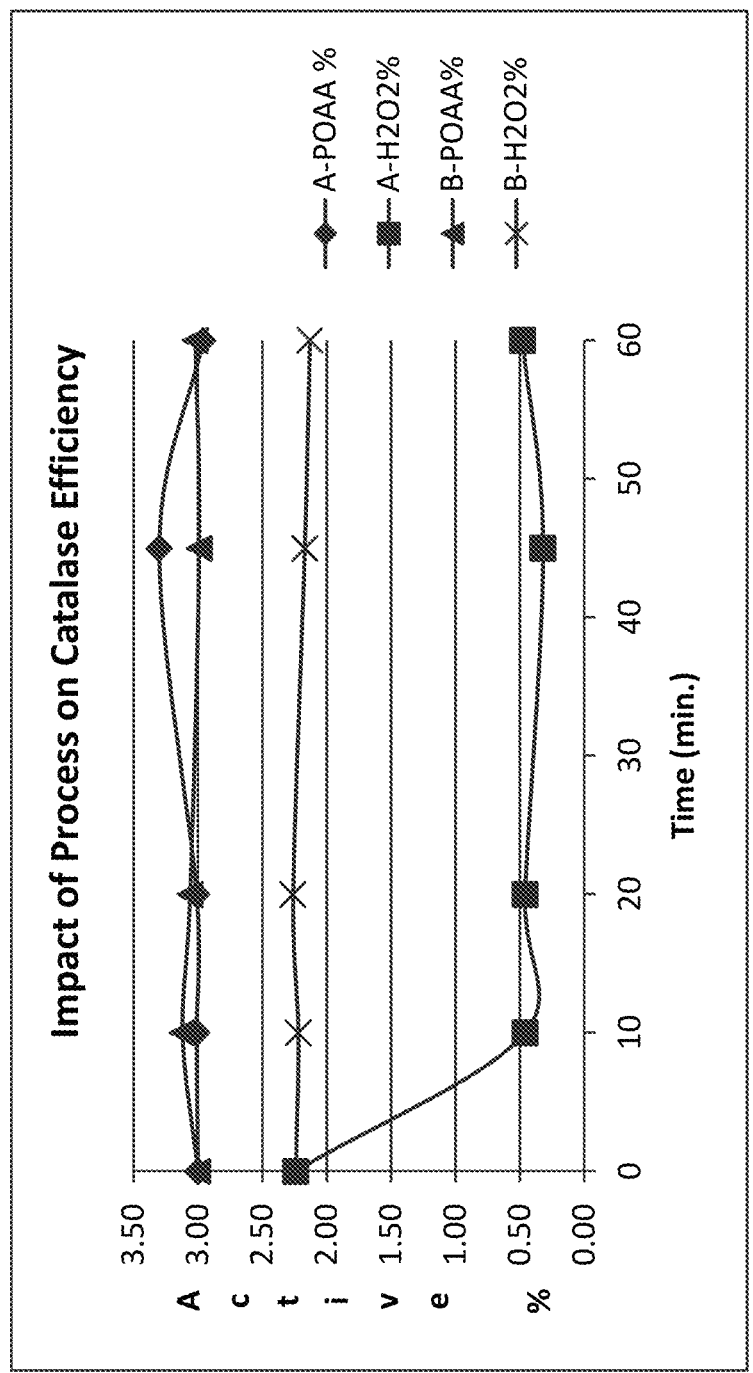
FIG. 19 shows the compatibility of peracid and catalase compositions as a result of processes of combining the same to produce reduced peroxide peracid compositions according to embodiments of the invention.

As shown in Table 17, the process of adding the peroxide-reducing enzymes impacted the efficacy of the hydroxide removal from the POAA peracid compositions. As further shown in FIG. 19, the mixture of POAA and $H_2O_2$ is preferably added to the catalase solution to achieve the maximum efficiency of hydrogen peroxide removal/reduction.

TABLE 17

| Time (min.) | A | | B | |
|---|---|---|---|---|
| | POAA % | H2O2 % | POAA % | H2O2 % |
| 0 | 3.00 | 2.24 | 3.00 | 2.24 |
| 10 | 3.01 | 0.46 | 3.12 | 2.22 |
| 20 | 3.01 | 0.46 | 3.06 | 2.26 |
| 45 | 3.30 | 0.32 | 2.99 | 2.17 |
| 60 | 2.96 | 0.48 | 3.02 | 2.13 |

Example 15

Field of use applications were analyzed to determine the amount of a peroxide-reducing enzyme necessary to obtain desired concentrations of both peracid and hydrogen peroxide in a treated water source. EnviroSan (POAA) peracid composition was added to water to reach the targeted POAA concentrations set forth in Table 18, and the concentration of both POAA and $H_2O_2$ were confirmed by iodometric titration. Then catalase (ES2000) was added to the solution, and the sample was stored under ambient conditions. The concentration of POAA and $H_2O_2$ were monitored by the iodometric conditions.

As shown in Table 18, the pond water with POAA and $H_2O_2$ could be treated with as low as 0.5 ppm catalase within 4 hours. The results further demonstrate that higher levels (concentrations) of catalase work more efficiently in decomposing $H_2O_2$ from the peracid composition. Regardless, approximate 1 ppm catalase is sufficient for treating the water source. In addition, the results show that under the tested ambient conditions, catalase selectively decomposes the $H_2O_2$ without having any negative impact on POAA stability.

TABLE 18

| Catalase (ppm) | Time (hr). | POAA (ppm) | H2O2(ppm) |
|---|---|---|---|
| 0.5 | 0 | 14.6 | 12.0 |
| 0.5 | 1 | 15.0 | 7.5 |
| 0.5 | 2 | 14.3 | 6.5 |
| 0.5 | 3.6 | 14.2 | 1.8 |
| 0.5 | 0 | 31.1 | 22.8 |
| 0.5 | 1 | 32.0 | 12.2 |
| 0.5 | 2 | 29.2 | 7.8 |
| 0.5 | 3.6 | 30.6 | 3.4 |
| 1.0 | 0 | 14.8 | 12.6 |
| 1.0 | 1 | 14.6 | 3.7 |
| 1.0 | 2 | 14.2 | 1.1 |
| 1.0 | 3.6 | 15.9 | 0.4 |
| 1.0 | 0 | 30.1 | 23.3 |
| 1.0 | 1 | 31.0 | 7.6 |
| 1.0 | 2 | 29.6 | 2.3 |
| 1.0 | 3.6 | 29.3 | 0.0 |

Example 16

The stability of treated peracid compositions according to the invention was evaluated to determine the impact of acidulants on compositional stability. pH adjustments to POAA compositions were made using various acidulants to decrease the pH of the peracid compositions as a means of pretreating the compositions prior to use according to the various methods of the invention. The EnviroSan (POAA) peracid composition was pretreated with the following materials to assess the impact on the stability of POAA: chlorine dioxide ($ClO_2$), catalase, or nitric acid ($HNO_3$). The following methods were employed to test the stability (as measured by remaining ppm POAA) of the peracid compositions in 20/80 water (produced/5 grain water), as set forth in Table 19.

The chlorine dioxide (100 ppm) was added as a pretreatment to 100 ml of 100% produced water. Two hours elapsed before the 1% EnviroSan was added and POAA stability was tested in the acidified water source to be treated according to the invention.

The catalase pretreatment consisted of adding 1% EnviroSan to 100 ppm catalase. The solution was stirred for 6.5 minutes before POAA stability was tested.

The pretreatment of 100 ml of 100% produced water with the acid (diluted $HNO_3$ to pH 2.5) included stirring the solution magnetically for ~1 hour. Then 20 g of the acidified water to be treated according to the invention was mixed with 80 g of 5 grain water, and the pH of the solution was adjusted from 5.5 to 6.6 before adding the 1% EnviroSan for POAA stability testing.

No acidification and/or pretreatment of the water source was conducted for the Control experiment.

TABLE 19

| Time (min.) | Sample | | | |
|---|---|---|---|---|
| | Control | Catalase Pretreated | $ClO_2$ Pretreated* | Acid pretreated |
| 0 | 27 | 27 | 28 | 28 |
| 1 | 14 | 22 | 28 | 26 |
| 4 | 3 | 20 | 29 | 19 |
| 5 | 2 | 19 | 28 | 22 |
| 6 | 0 | 20 | 29 | 22 |

*Minor interference observed in iodometric titration

Figure 20:
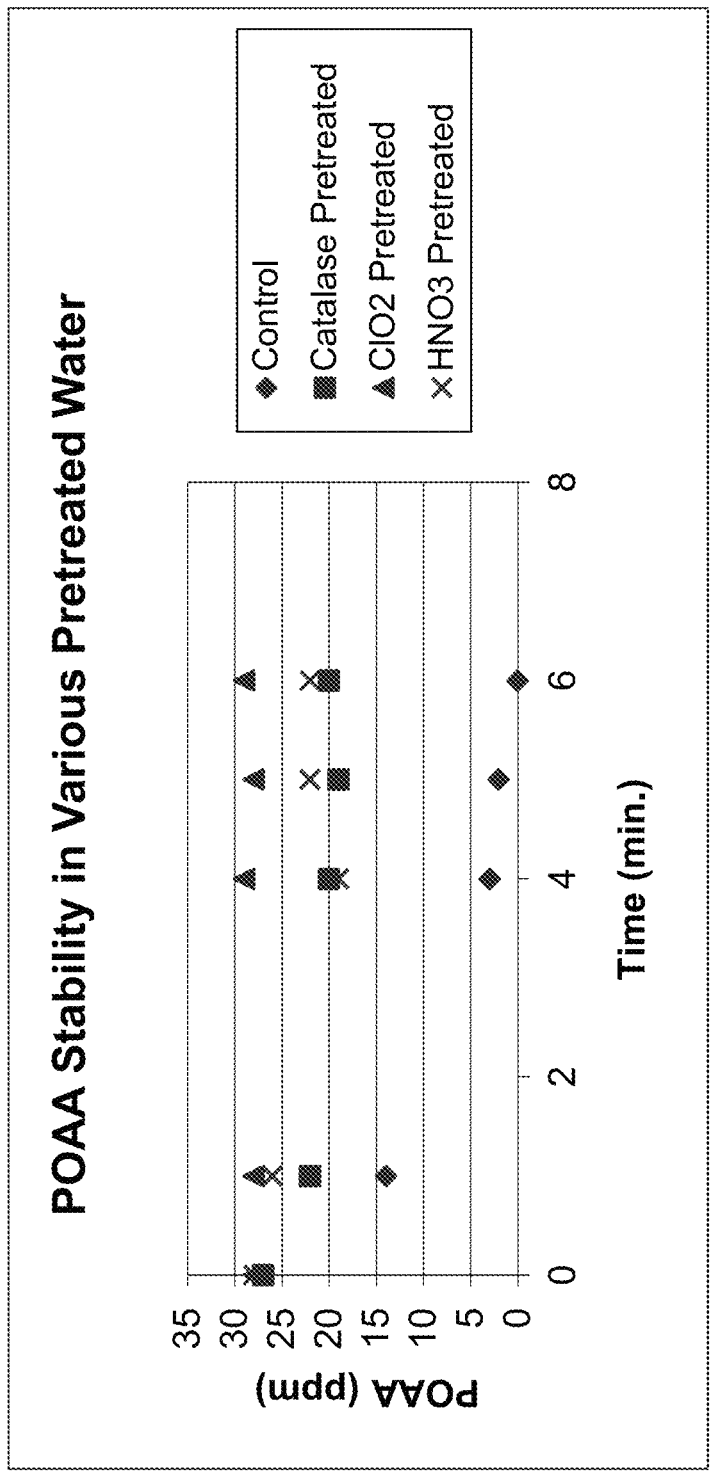
FIG. 20 shows the impact on peracid composition stability in various pretreated contaminated water sources according to embodiments of the invention.

As shown in FIG. 20, there is a clear benefit for use of an acidulant with the treated peracid compositions according to the invention in order to improve the peracid stability.

The improved stability (ppm POAA over elapsed time) shown demonstrates that a pretreatment of a water source to decrease the pH of the water to be acidic, results in prolonged peracid stability.

Example 17

To a water mixture of 80/20 (5 grain/produced water) was added the various peracid compositions with stirring. The level of peracid at specific times was assayed by iodometric titration. The following peracid compositions were employed: EnviroSan: 60 microliter/100 g (POAA, 13.97%, $H_2O_2$, 10.41%); Low Peroxide POAA: 65 microliter/100 g (POAA 12.72, $H_2O_2$, 1.55%); and EnviroSan/HAC (i.e. Acidified EnviroSan): 60 microliter EnviroSan plus 25 microliter/Hac/100 g.

For catalase treatment, 0.3 g of ES 2000 was added to 78.53 g of water, then 21.47 g of EnviroSan was added in the solution without stirring. At the end of the addition the peracid and hydrogen peroxide concentrations were assayed (POAA 2.77%, $H_2O_2$ 0.51%). The results are shown in Table 20.

TABLE 20

| Sample | Time (min.) | W (g) | $V_{(ml.\ 0.1\ N\ Na2S2O3)}$ | POAA (ppm) | pH |
|---|---|---|---|---|---|
| EnviroSan | 0 | | | 94 | 6.30 |
| | 1 | 21.08 | 0.47 | 85 | |

TABLE 20-continued

| Sample | Time (min.) | W (g) | $V_{(ml.\ 0.1\ N\ Na2S2O3)}$ | POAA (ppm) | pH |
|---|---|---|---|---|---|
| | 2 | 18.19 | 0.30 | 63 | |
| | 3 | 17.62 | 0.24 | 52 | |
| | 4 | 20.51 | 0.24 | 44 | |
| | 5 | 21.78 | 0.22 | 38 | |
| Low Peroxide POAA | 0 | | | 90 | 5.42 |
| | 1 | 21.78 | 0.48 | 84 | |
| | 2 | 22.36 | 0.48 | 82 | |
| | 3 | 18.95 | 0.4 | 80 | |
| | 4 | 19.61 | 0.42 | 81 | |
| | 5 | 18.11 | 0.39 | 82 | |
| Envirosan-HAc (i.e. acidified) | 0 | | | 94 | 5.38 |
| | 1 | 21.73 | 0.48 | 84 | |
| | 2 | 17.94 | 0.40 | 85 | |
| | 3 | 17.97 | 0.38 | 80 | |
| | 4 | 18.07 | 0.38 | 80 | |
| | 5 | 21.22 | 0.42 | 75 | |
| EnviroSan (3% POAA)-Catalase | 0 | | | 90 | 6.18 |
| | 1 | 17.92 | 0.38 | 81 | |
| | 2 | 17.96 | 0.34 | 72 | |
| | 3 | 18.5 | 0.32 | 66 | |
| | 4 | 19.75 | 0.31 | 60 | |
| | 5 | 23.97 | 0.36 | 57 | |

Figure 21:
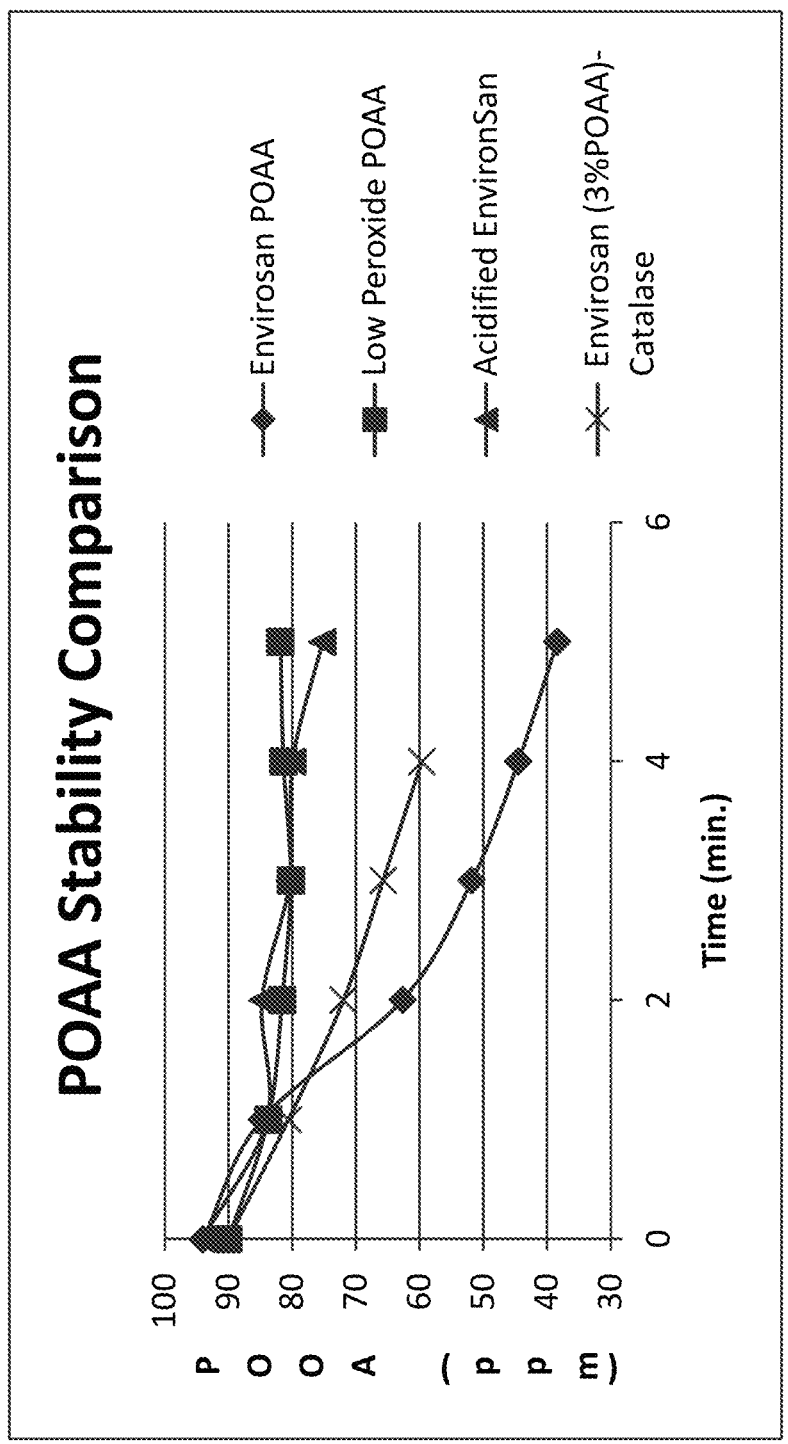
FIG. 21 shows differences in POAA composition stability according to embodiments of the invention.

Again as shown in FIG. 21, there is a clear benefit for use of an acidulant with the treated peracid compositions according to the invention in order to improve the peracid stability.

Example 18

An inorganic metal peroxide-reducing agent was evaluated for its specificity of reducing hydrogen peroxide in peracid compositions in comparison to peracid reduction. As shown in Table 21, various POAA compositions with varying starting concentrations of hydrogen peroxide were contacted with a platinum (Pt) catalyst. The tested compositions were generated as follows: Composition A (2000 ppm POAA plus 250 ppm $H_2O_2$; 0.2166% w/w peracid, 0.0034 wt-% measured $H_2O_2$); Composition B (2000 ppm POAA plus 500 ppm $H_2O_2$; 0.2166% w/w peracid, 0.0094 wt-% measured $H_2O_2$); Composition C (2000 ppm POAA plus 1000 ppm $H_2O_2$; 0.2138% w/w peracid, 0.0340 wt-% measured $H_2O_2$); Composition D (2000 ppm POAA plus 2000 ppm $H_2O_2$; 0.2119% w/w peracid, 0.0540 wt-% measured $H_2O_2$).

A zeolite (i.e. a porous structure that can accommodate a wide variety of cations and are used in formulating catalysts) was used to suspending a sample of an inorganic metal peroxide-reducing agent. The zeolite was saturated with various metal peroxide-reducing agents (as set forth in the various different examples) in a solution of peracetic acid. The zeolites that were employed are commonly used in the industry of hydrocarbon cracking for catalysis. The concentrations of POAA and $H_2O_2$ were then measured with an iodometric titration over time to show the impact of the particular metal peroxide-reducing agent on selective or non-selective degradation of POAA and/or $H_2O_2$.

Figure 22:
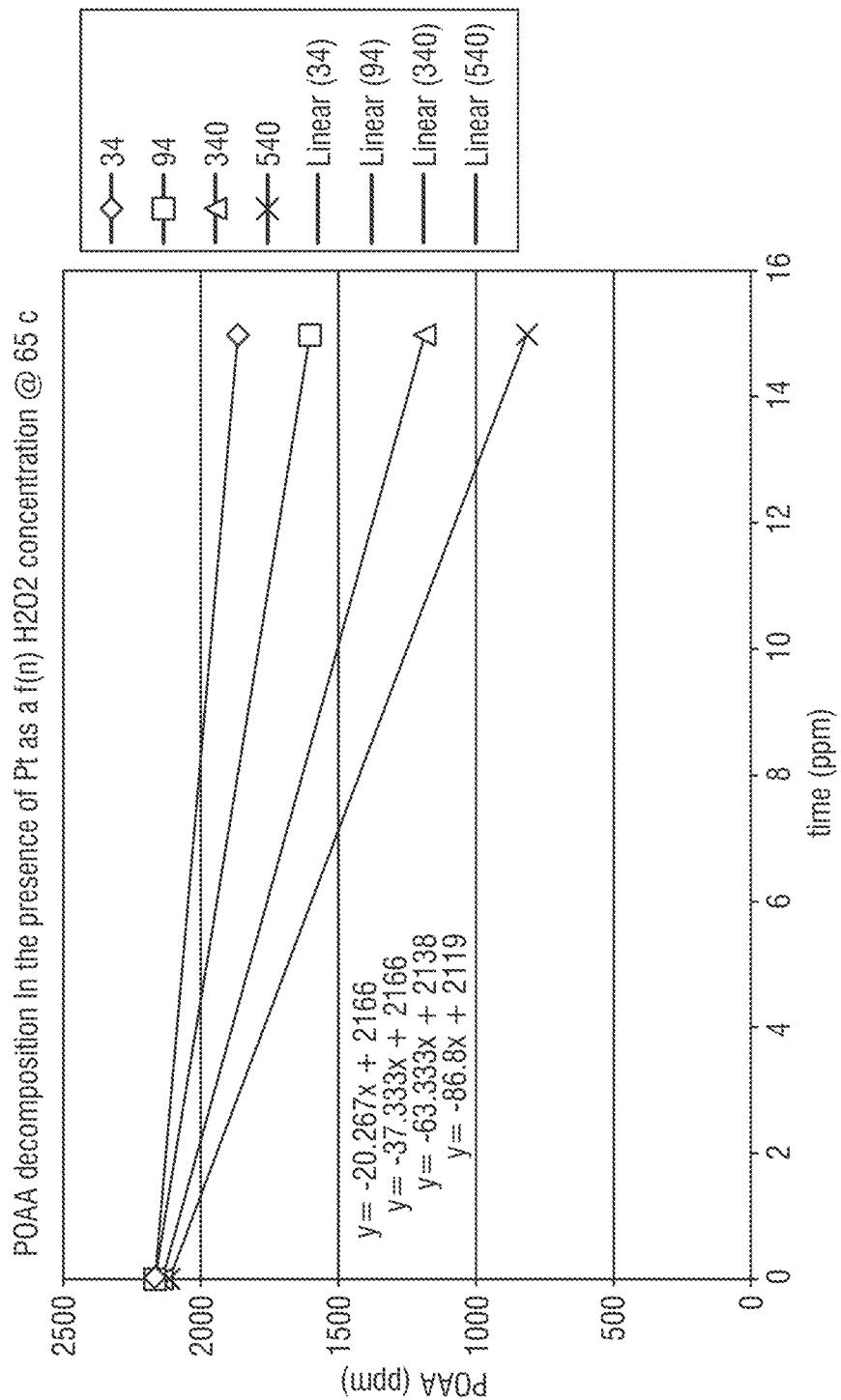
FIG. 22 shows the difference in POAA decomposition within a peracid composition treated with an inorganic metal peroxide-reducing agent, wherein the peracid compositions have varying concentrations of hydrogen peroxide.

Table 21 shows the comparison of the initial POAA concentration and the final POAA concentration after 15 minutes contact with the peroxide-reducing agent according to the invention is shown in FIG. 22.

TABLE 21

| Composition | Peroxide Conc | initial POAA | 15 minute POAA |
|---|---|---|---|
| A | 34 | 2166 | 1862 |
| B | 94 | 2166 | 1606 |

TABLE 21-continued

| Composition | Peroxide Conc | initial POAA | 15 minute POAA |
|---|---|---|---|
| C | 340 | 2138 | 1188 |
| D | 540 | 2119 | 817 |

Figure 23:
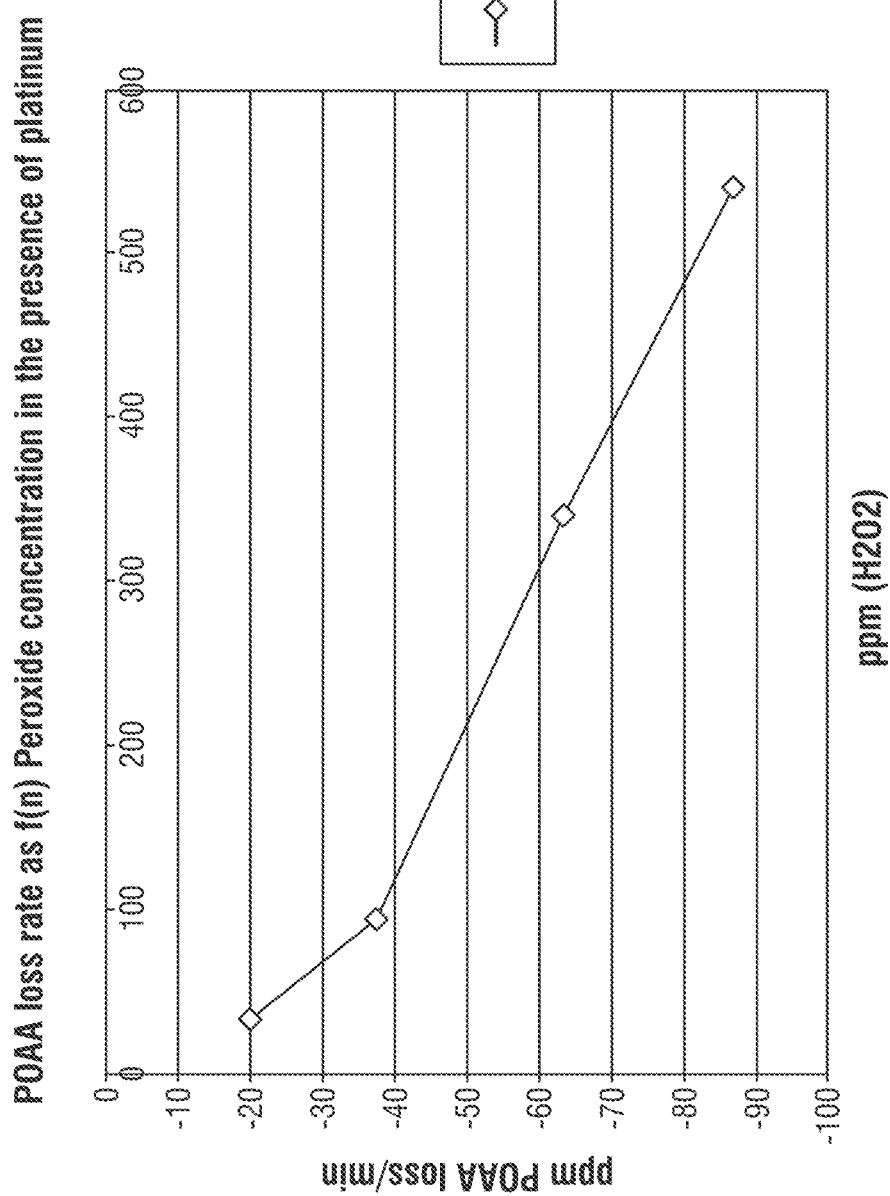
FIG. 23 shows the loss rate of POAA concentration in the presence of a platinum peroxide-reducing agent.

As shown in Table 22, the decomposition rates of the POAA concentration in the various peracid compositions are further shown. As shown in both Table 22 and FIG. 23, as the concentration of hydrogen peroxide increases the POAA loss rate similarly increases. As a result, the peroxide-reducing agent provides a partially selective peroxide decomposition from peracid compositions.

TABLE 22

| ppm $H_2O_2$ | POAA loss rate |
|---|---|
| 34 | −20.267 |
| 94 | −37.333 |
| 340 | −63.33 |
| 540 | −86.8 |

The results demonstrate the partial selectivity of the inorganic peroxide-reducing agent platinum (Pt), suitable for use according to the methods of the invention. The inorganic peroxide-reducing agent was then evaluated in combination with the peroxide-reducing enzyme agent catalase. The 2000 ppm POAA compositions were measured at 0 minutes, 30 minutes, 60 minutes, 120 minutes and 240 minutes, as shown in Table 23 under the various combinations with a catalase peroxide-reducing enzyme.

TABLE 23

| | POAA Concentration | | |
|---|---|---|---|
| Time | Catalase + Pt | Catalase + Pretreated Pt | Catalase only |
| 0 | 1934 | 1934 | 1934 |
| 30 | 1824 | 1784 | 1891 |
| 60 | 1710 | 1615 | 1929 |
| 120 | 1406 | 1210 | 1877 |
| 240 | 874 | 608 | 1568 |

Figure 24:
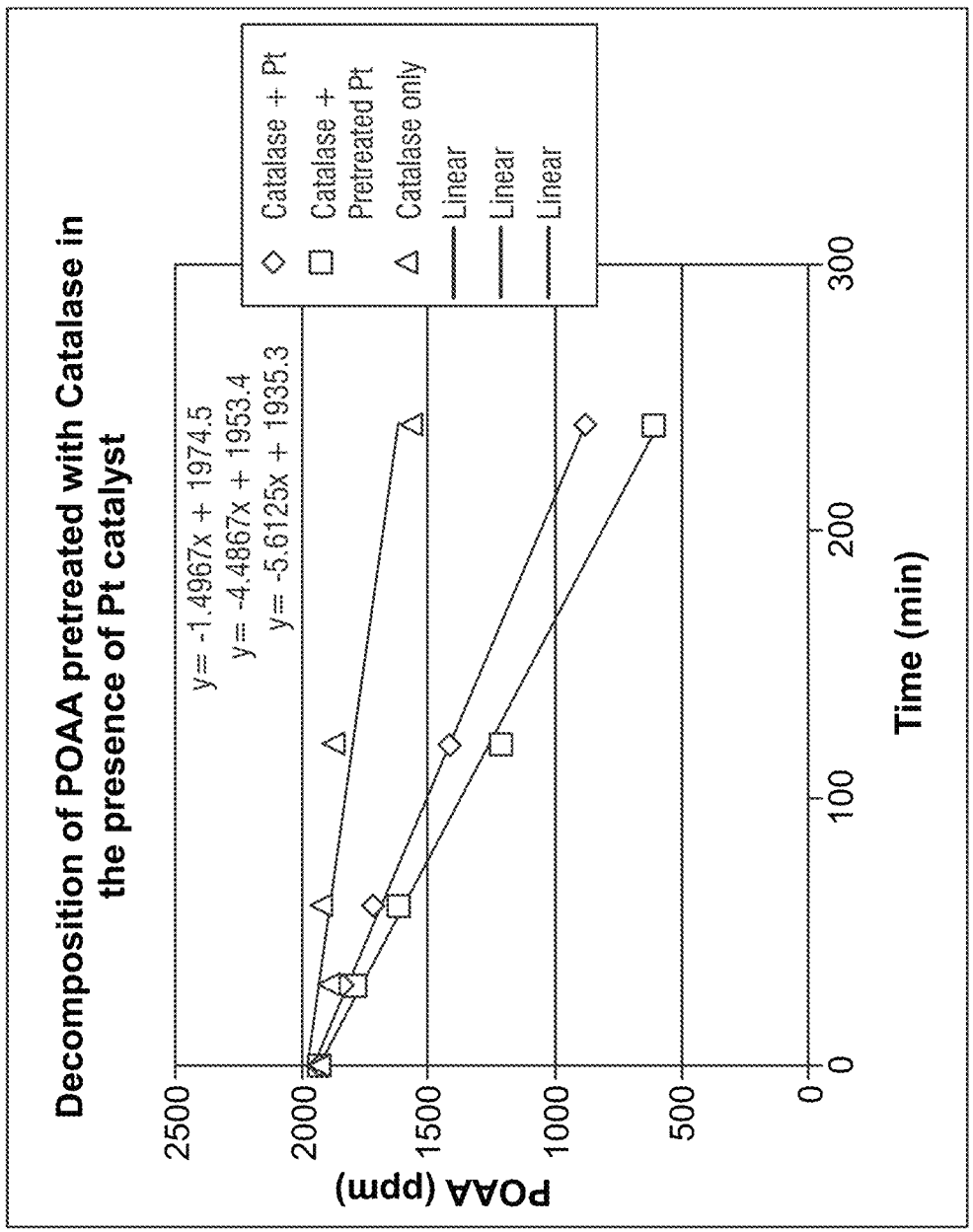
FIG. 24 shows the decomposition of POAA compositions treated with a platinum peroxide-reducing agent (with/without a catalase peroxide-reducing enzyme agent) according to embodiments of the invention.

FIG. 24 graphically shows the results of the decrease in POAA (e.g. peracid decomposition), showing that inorganic peroxide-reducing agent results in less selective hydrogen peroxide reduction or decomposition in comparison to the peroxide-reducing enzyme catalase. However, the inorganic peroxide-reducing agent provides a partially selective peroxide decomposition from peracid compositions.

Example 19

Additional inorganic metals were evaluated for use as solid catalysts for evaluation as peroxide decomposition catalysts according to the methods of the invention. The metals tungsten (W), zirconium (Zr), and ruthenium (Ru) were evaluated to determine whether the metals preferentially reduce hydrogen peroxide concentration over peracid concentration within a peracid composition. Table 24 shows the various formulations evaluated over 4 hours.

TABLE 24

| | control | WZr | | control | WZr | |
|---|---|---|---|---|---|---|
| Time | POAA | POAA | Ru POAA | $H_2O_2$ | $H_2O_2$ | Ru $H_2O_2$ |
| 0 | 1986 | 1986 | 1986 | 1547 | 1547 | 1547 |
| 15 | 1938 | 2252 | 513 | 1539 | 1267 | 0 |
| 60 | 1862 | 1330 | 228 | 1556 | 1071 | 0 |
| 240 | 1539 | 190 | 38 | 1509 | 327 | 0 |

Figure 25:
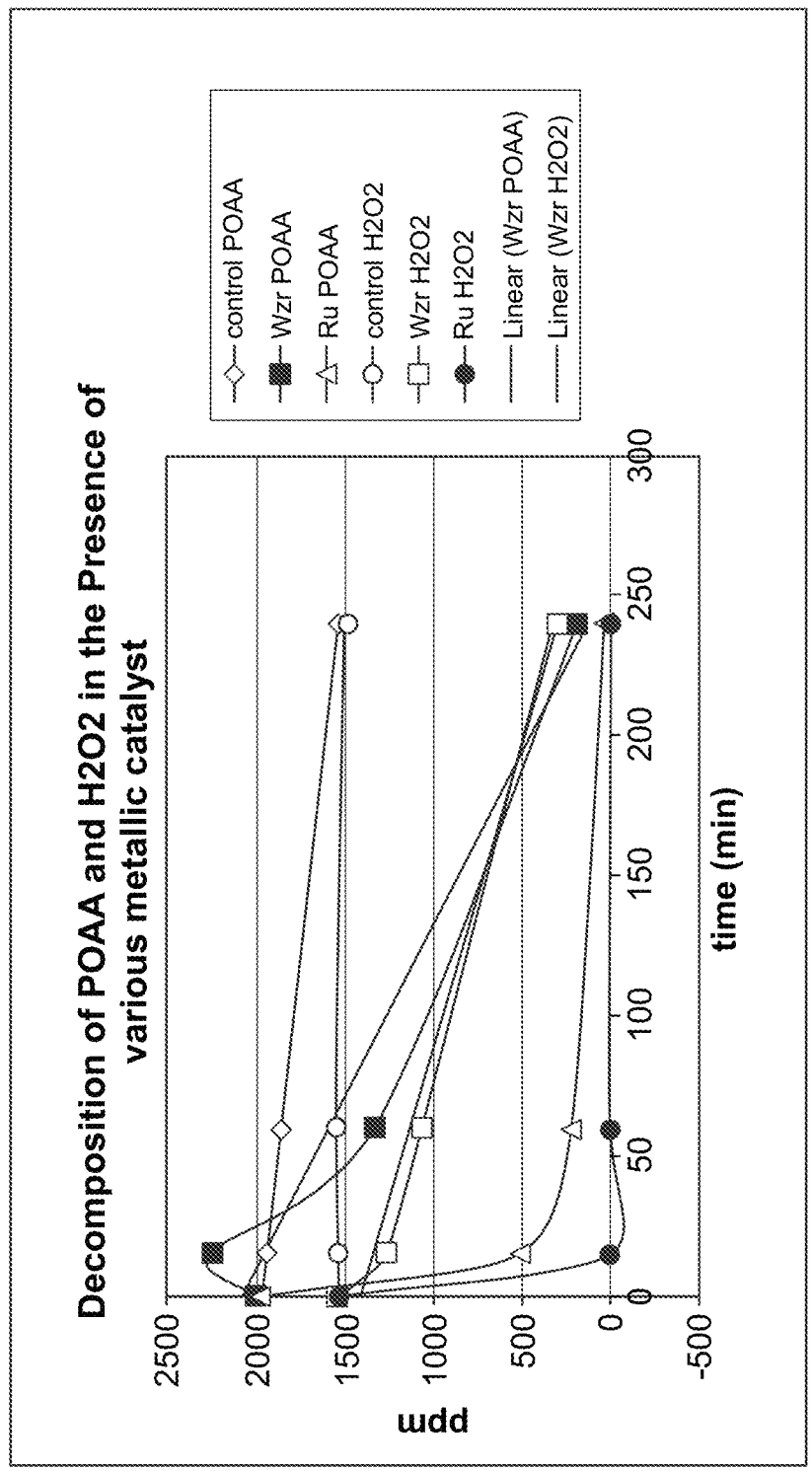
FIG. 25 shows the decomposition of POAA and hydrogen peroxide in peracid compositions treated with various metallic catalysts (e.g. peroxide-reducing agents) according to embodiments of the invention.

As shown in FIG. 25 the decrease in both POAA (e.g. peracid decomposition) and hydrogen peroxide are compared. Both inorganic peroxide-reducing agents resulted in significant decrease in both POAA and hydrogen peroxide, showing only a slight preference in hydrogen peroxide decomposition over POAA.

Example 20

Various additional inorganic metals and metal compounds were further evaluated for use as peroxide decomposition catalysts (e.g. peroxide-reducing agents) according to the methods of the invention. The metals were provided as solid catalysts to POAA solutions.

Table 25 shows the various solutions that were tested against 10 g CoMo, cobalt molybdenum peroxide-reducing agent sample, including a POAA plus catalase peracid composition, hydrogen peroxide plus acetic acid composition, hydrogen peroxide composition.

TABLE 25

| | POAA Concentration | | $H_2O_2$ Concentration | | | |
|---|---|---|---|---|---|---|
| Time | Equil. POAA | POAA + catalase | Equil. POAA | $H_2O_2$ | $H_2O_2$_HOAc | POAA + catalase |
| 0 | 2014 | 2071 | 1836 | 1615 | 1572.5 | 0 |
| 15 | 570 | 136.8 | 54.4 | 1343 | 1462 | 68 |
| 30 | 45.6 | 106.4 | 0 | 1156 | 1351.5 | 6.8 |
| 45 | 0 | 0 | 0 | 994.5 | 1207 | 0 |
| 60 | 0 | 0 | 0 | 841.5 | 1062.5 | 0 |

Figure 26:
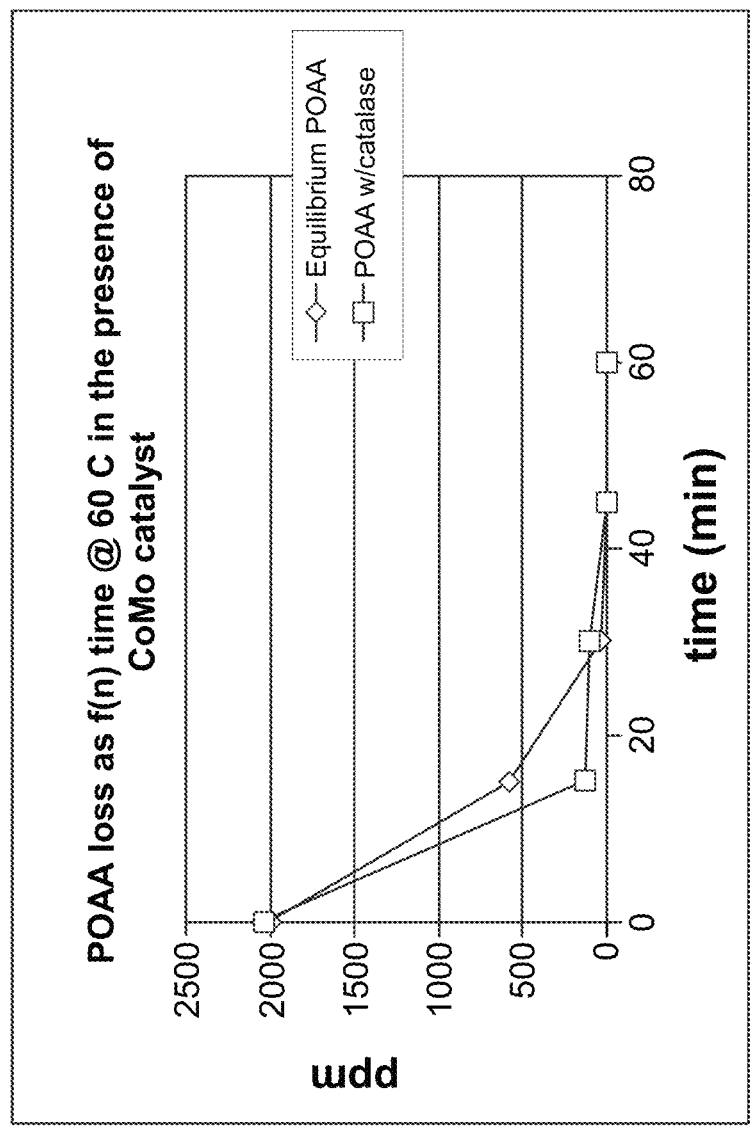
FIGS. 26-27 show POAA loss (FIG. 26) and hydrogen peroxide loss (FIG. 27) as a function of time in the presence of a CoMo peroxide-reducing agent according to embodiments of the invention.
Figure 27:
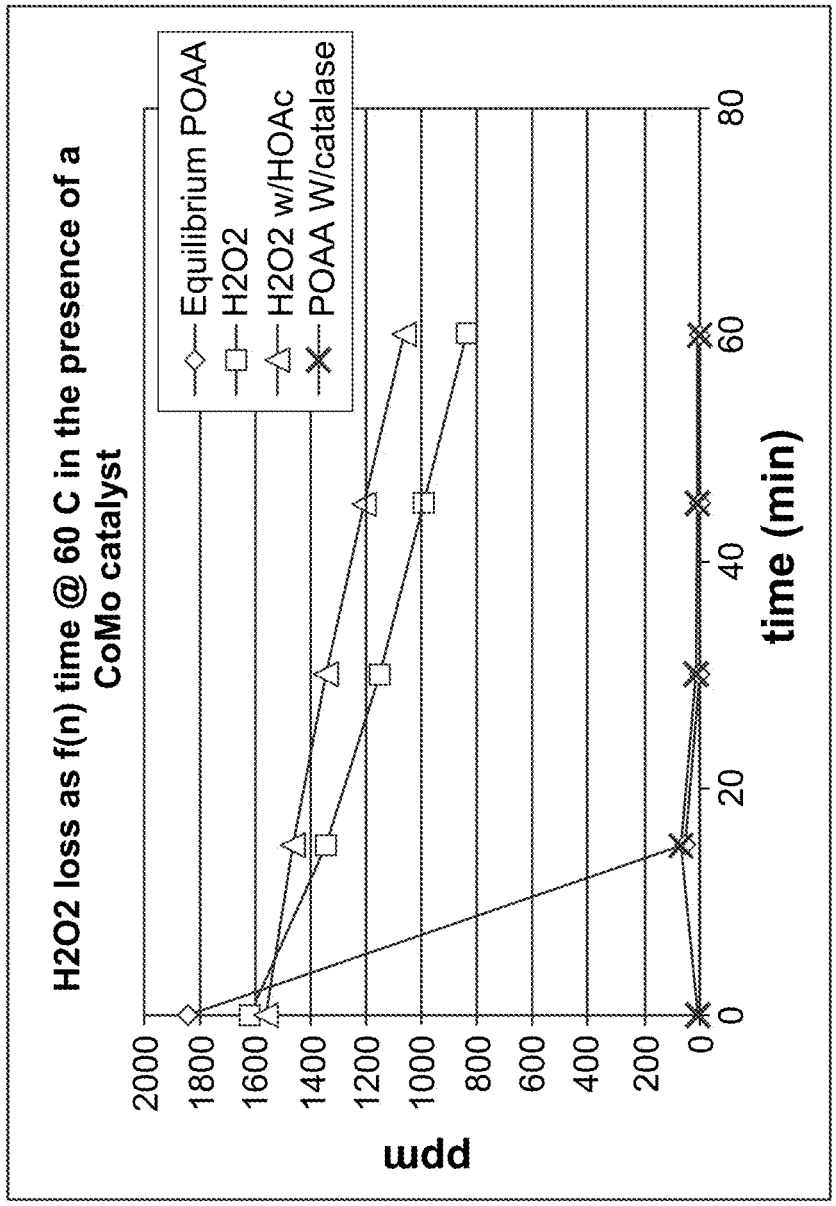

As shown in FIGS. 26-27, the POAA loss (FIG. 26) and hydrogen peroxide loss (FIG. 27) are a function of time of exposure to the peroxide-reducing agent CoMo.

Table 26 shows the various solutions that were tested against 10 g NiW, a nickel wolfram inorganic peroxide-reducing agent sample, including a POAA plus catalase peracid composition, hydrogen peroxide plus acetic acid composition, hydrogen peroxide composition.

TABLE 26

| | POAA Concentration | | | H2O2 Concentration | | | | |
|---|---|---|---|---|---|---|---|---|
| Time | Equil. POAA | POAA + catalase | POAA Control | POAA + catalase | $H_2O_2$_HOAc | $H_2O_2$ | Equil. POAA | Control |
| 0 | 2071 | 2014 | 2014 | 0 | 1572.5 | 1615 | 1836 | 1572.5 |
| 15 | 1976 | 1919 | 1938 | 0 | 1589.5 | 1581 | 1836 | 1589.5 |
| 30 | 1862 | 1786 | 1900 | 34 | 1589.5 | 1598 | 1751 | 1615 |
| 45 | 1710 | 1672 | 1881 | 68 | 1606.5 | 1615 | 1700 | 1640.5 |
| 60 | 1406 | 1539 | 1843 | 68 | 1606.5 | 1615 | 1632 | 1666 |

Figure 28:
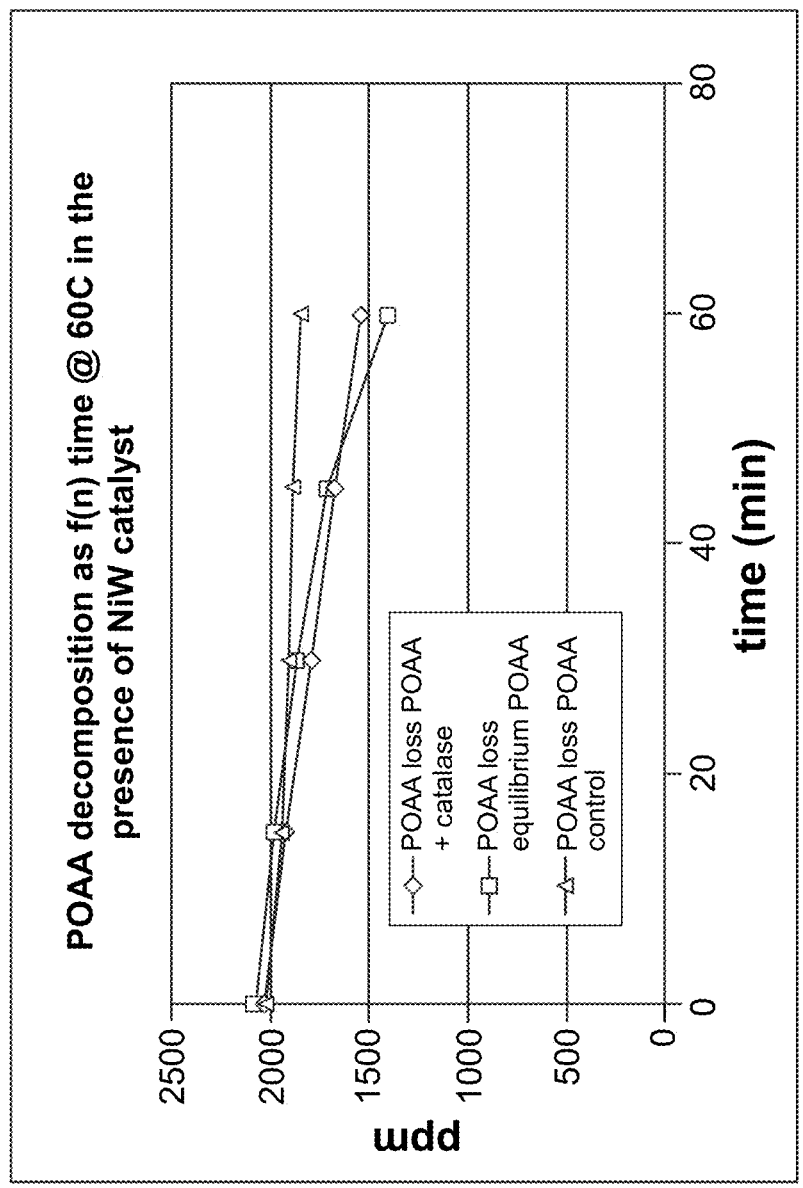
FIGS. 28-29 show POAA loss (FIG. 28) and hydrogen peroxide loss (FIG. 29) as a function of time in the presence of a NiW peroxide-reducing agent according to embodiments of the invention.
Figure 29:
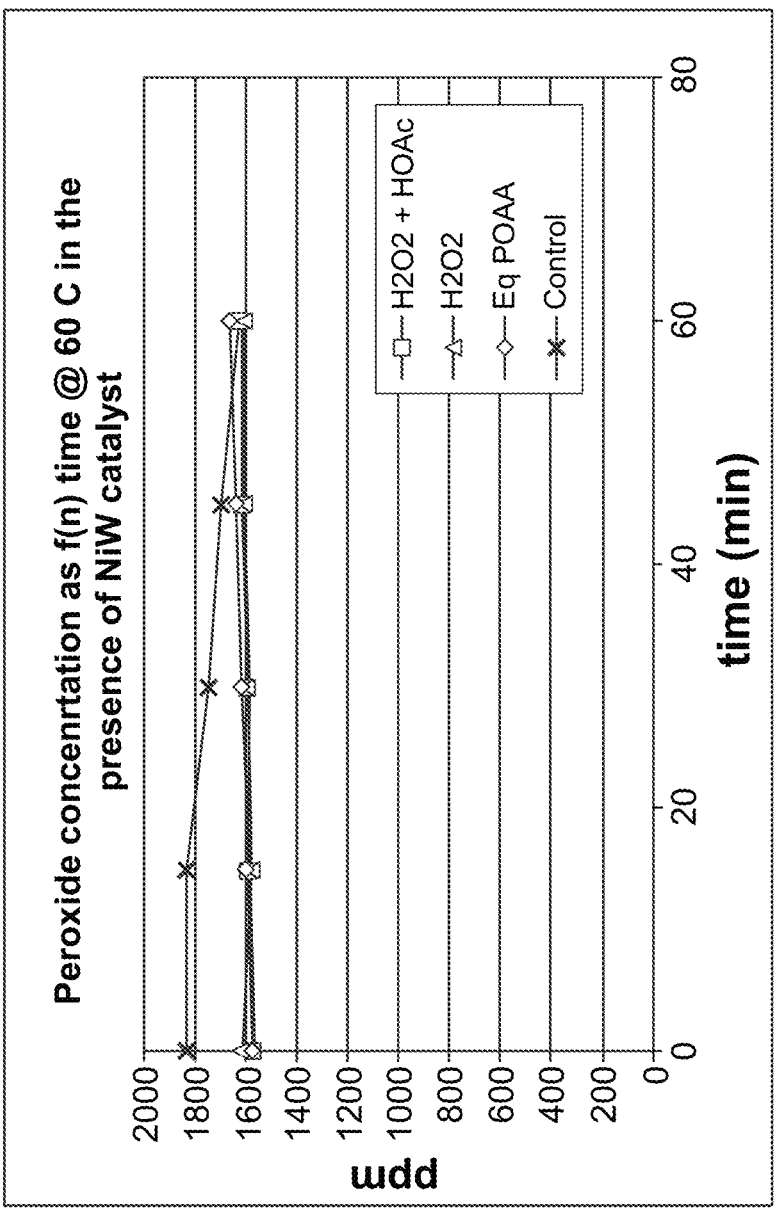

As shown in FIGS. 28-29 POAA loss (FIG. 28) and hydrogen peroxide loss (FIG. 29) are a function of time in the presence of a NiW peroxide-reducing agent.

Table 27 shows the various solutions that were tested against 10 g NiMo, a nickel molybdenum inorganic peroxide-reducing agent sample, including a POAA plus catalase peracid composition, hydrogen peroxide plus acetic acid composition, hydrogen peroxide composition.

TABLE 27

| | POAA Concentration | | | H2O2 Concentration | | | | |
|---|---|---|---|---|---|---|---|---|
| Time | Equil. POAA | POAA + catalase | POAA Control | POAA + catalase | $H_2O_2$_HOAc | $H_2O_2$ | Equil. POAA | Control |
| 0 | 2071 | 2014 | 2014 | 0 | 1572.5 | 1615 | 1836 | 1572.5 |
| 15 | 1482 | 1254 | 1938 | 289 | 1589.5 | 1581 | 1377 | 1589.5 |
| 30 | 760 | 874 | 1900 | 450.5 | 1615 | 1555.5 | 1173 | 1615 |
| 45 | 1140 | 456 | 1881 | 612 | 1640.5 | 1530 | 782 | 1640.5 |
| 60 | 0 | 532 | 1843 | 544 | 1666 | 1496 | 0 | 1666 |

Figure 30:
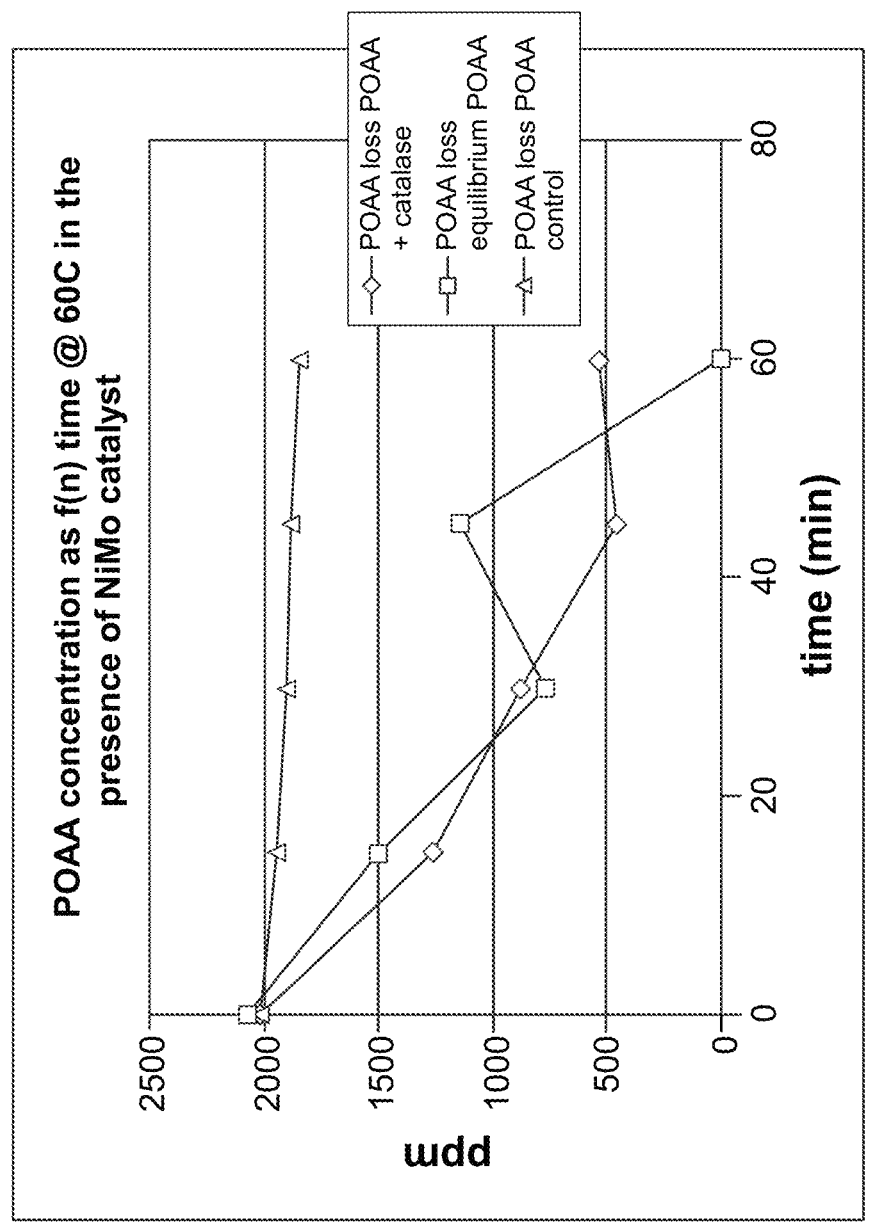
FIGS. 30-33 show POAA loss (FIGS. 30, 32, 33) and hydrogen peroxide loss (FIGS. 31-33) as a function of time in the presence of a NiMo peroxide-reducing agent according to embodiments of the invention.
Figure 31:
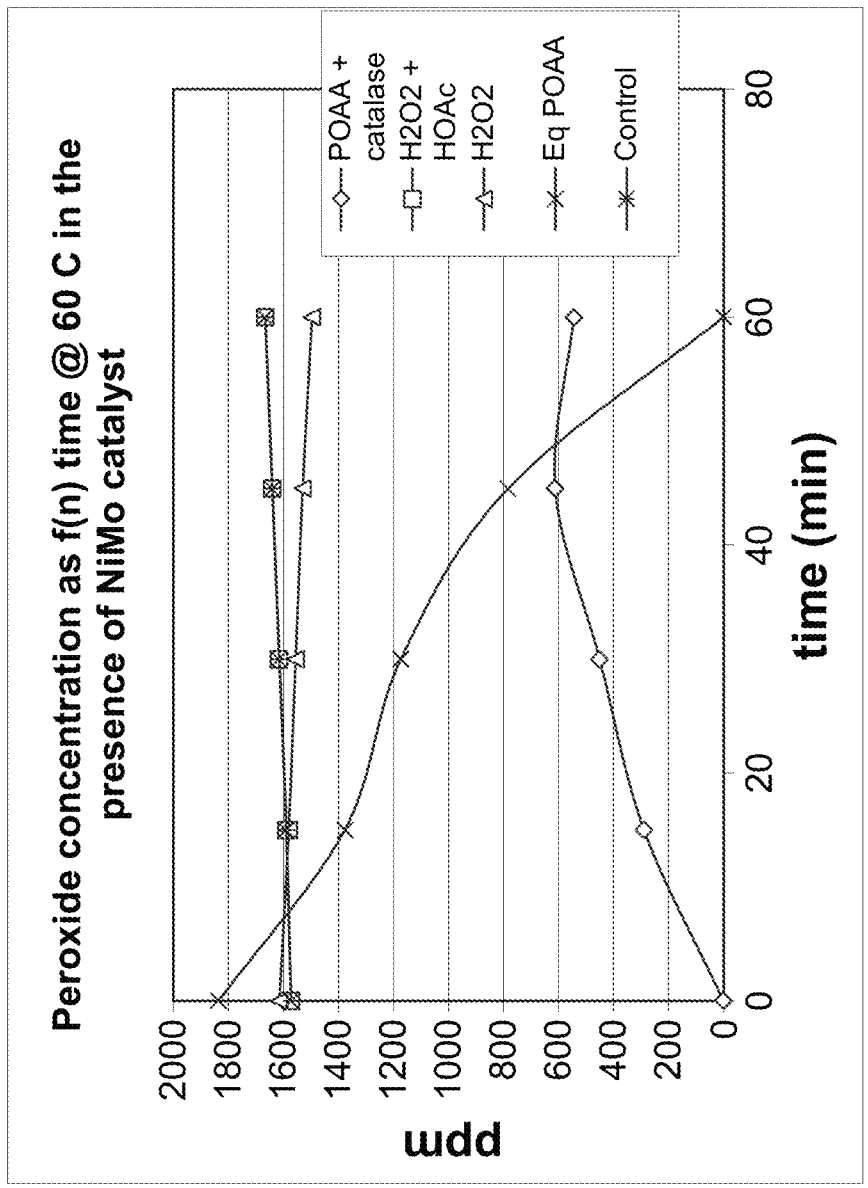

As shown in FIGS. 30-31 POAA loss (FIG. 30) and hydrogen peroxide loss (FIG. 31) are a function of time in the presence of a NiMo peroxide-reducing agent.

Figure 32:
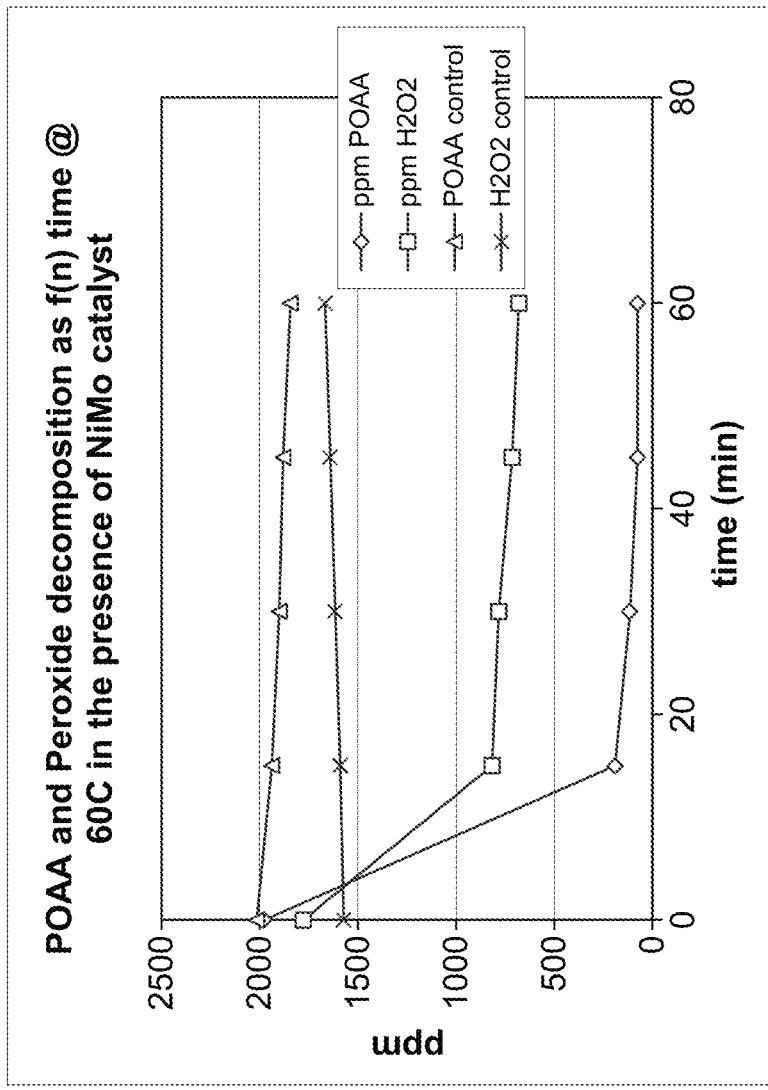
Figure 33:
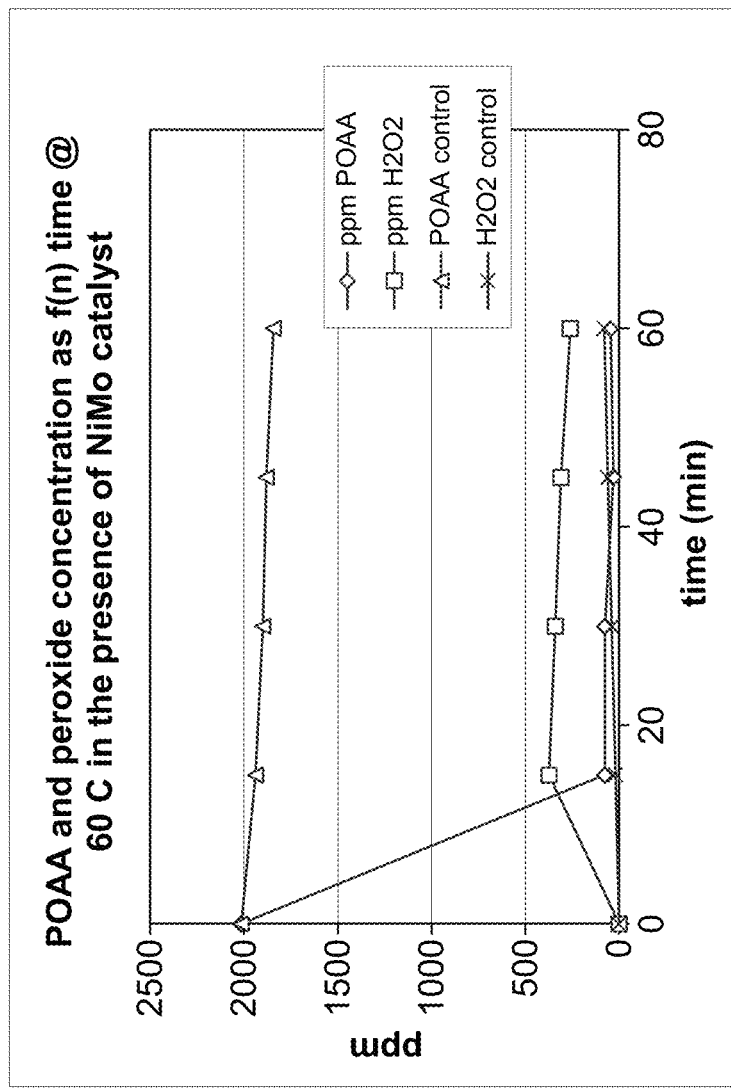

Additional testing using the NiMo, nickel molybdenum inorganic peroxide-reducing agent was conducted using a different titration methodology, due to some molybdenum metal leaching into the POAA solution (e.g. potentially negative effects on the POAA/hydrogen peroxide separation). To correct this, 2 separate 10 ml samples were collected at each time point during the test. One of the samples was treated with a small amount (~1 mml) of added catalase to eliminate the hydrogen peroxide in the solution. The second solution was titrated for total oxygen content with addition of oxygen catalyst, sulfuric acid and KI. As a result, the titration volume from the catalase treated sample represents a direct measurement of the POAA content in the solution, and the total oxygen titration minus the catalase treated titration equals the amount of peroxide in the solution. The results are outlined in Table 28 and shown in FIGS. 32-33.

TABLE 28

| time | Titration with catalase | Total Oxygen titration | ppm POAA | ppm $H_2O_2$ | POAA control | $H_2O_2$ control |
|---|---|---|---|---|---|---|
| A | | | | | | |
| 0 | 5.2 | 15.65 | 1976 | 1776.5 | 2014 | 1572.5 |
| 15 | 0.5 | 5.3 | 190 | 816 | 1938 | 1589.5 |
| 30 | 0.3 | 4.9 | 114 | 782 | 1900 | 1615 |

TABLE 28-continued

| time | Titration with catalase | Total Oxygen titration | ppm POAA | ppm $H_2O_2$ | POAA control | $H_2O_2$ control |
|---|---|---|---|---|---|---|
| 45 | 0.2 | 4.4 | 76 | 714 | 1881 | 1640.5 |
| 60 | 0.2 | 4.2 | 76 | 680 | 1843 | 1666 |
| B (Pre-treated POAA with catalase) | | | | | | |
| 0 | 5.3 | 5.3 | 2014 | 0 | 2014 | 0 |
| 15 | 0.2 | 2.4 | 76 | 374 | 1938 | 20 |
| 30 | 0.2 | 2.2 | 76 | 340 | 1900 | 40 |
| 45 | 0.08 | 1.9 | 30.4 | 309.4 | 1881 | 60 |
| 60 | 0.12 | 1.65 | 45.6 | 260.1 | 1843 | 80 |

Table 29 shows the various solutions that were tested against 10 g Mo, a molybdenum inorganic peroxide-reducing agent sample, including a POAA plus catalase peracid composition, hydrogen peroxide plus acetic acid composition, hydrogen peroxide composition.

TABLE 29

| Time | POAA Concentration | | | $H_2O_2$ Concentration | | | | |
|---|---|---|---|---|---|---|---|---|
| | Equil. POAA | POAA + catalase | POAA Control | POAA + catalase | $H_2O_2$—HOAc | $H_2O_2$ | Equil. POAA | Control |
| 0 | 2071 | 2014 | 2014 | 0 | 1572.5 | 1615 | 1836 | 1572.5 |
| 15 | 1482 | 988 | 1938 | 408 | 1530 | 1334.5 | 1615 | 1589.5 |
| 30 | 988 | 836 | 1900 | 493 | 1436.5 | 1181.5 | 1462 | 1615 |
| 45 | 684 | 608 | 1881 | 569.5 | 1317.5 | 986 | 1088 | 1640.5 |
| 60 | 0 | 418 | 1843 | 654.5 | 1190 | 841.5 | 0 | 1666 |

Figure 34:
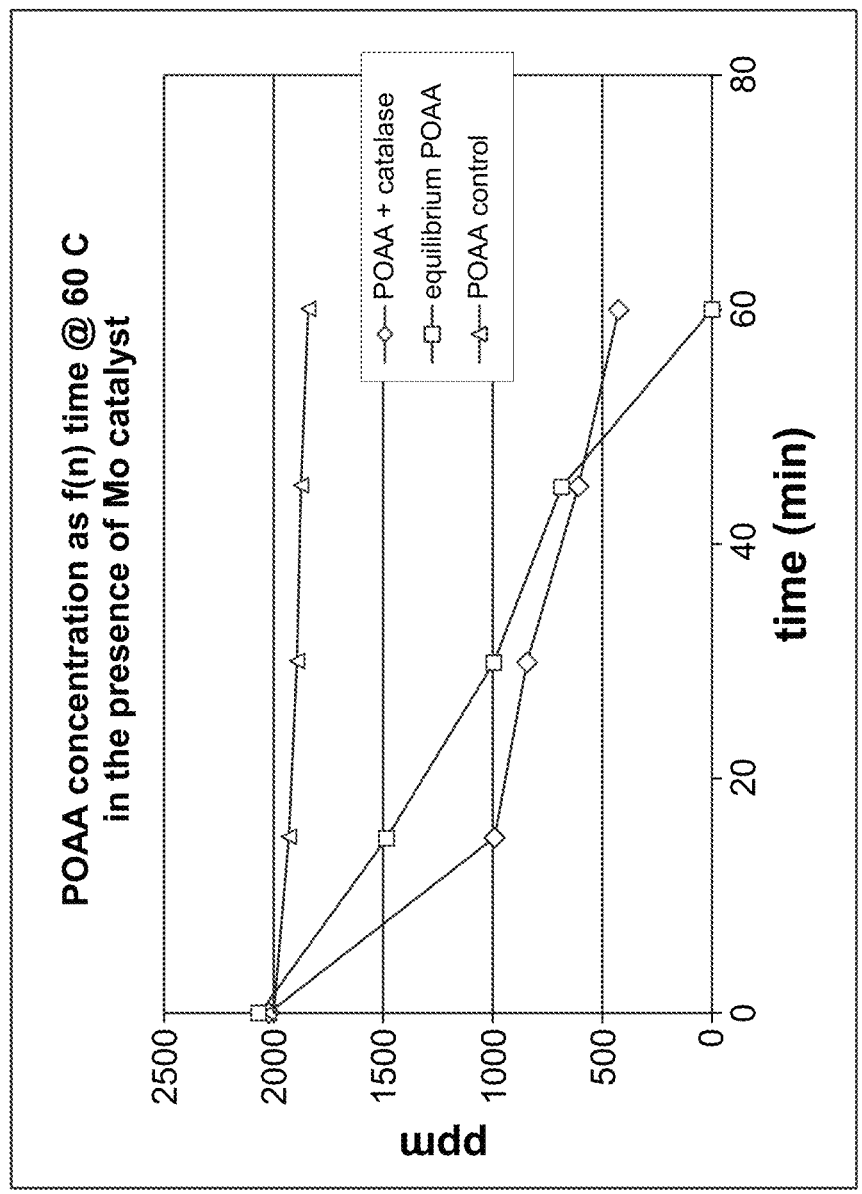
FIGS. 34-37 show POAA loss (FIGS. 34, 36, 37) and hydrogen peroxide loss (FIGS. 35-37) as a function of time in the presence of a Mo peroxide-reducing agent according to embodiments of the invention.
Figure 35:
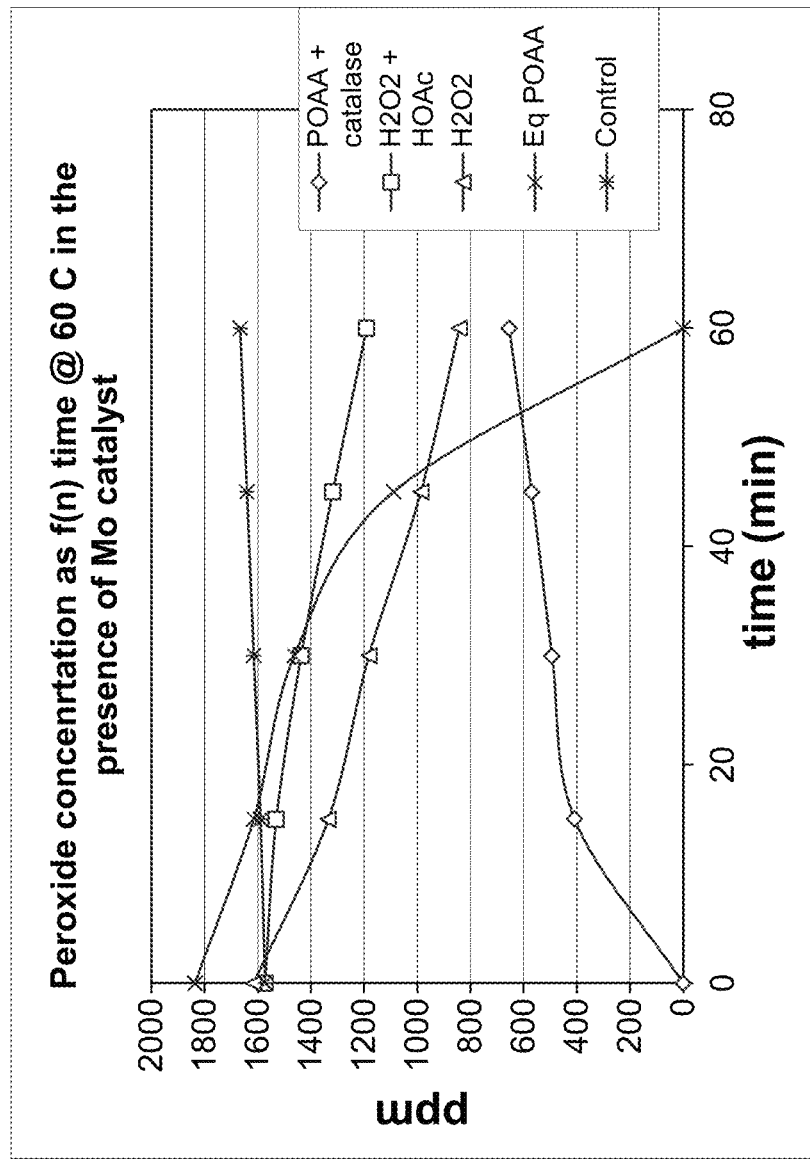

As shown in FIGS. 34-35 POAA loss (FIG. 34) and hydrogen peroxide loss (FIG. 35) are a function of time in the presence of a Mo peroxide-reducing agent.

Figure 36:
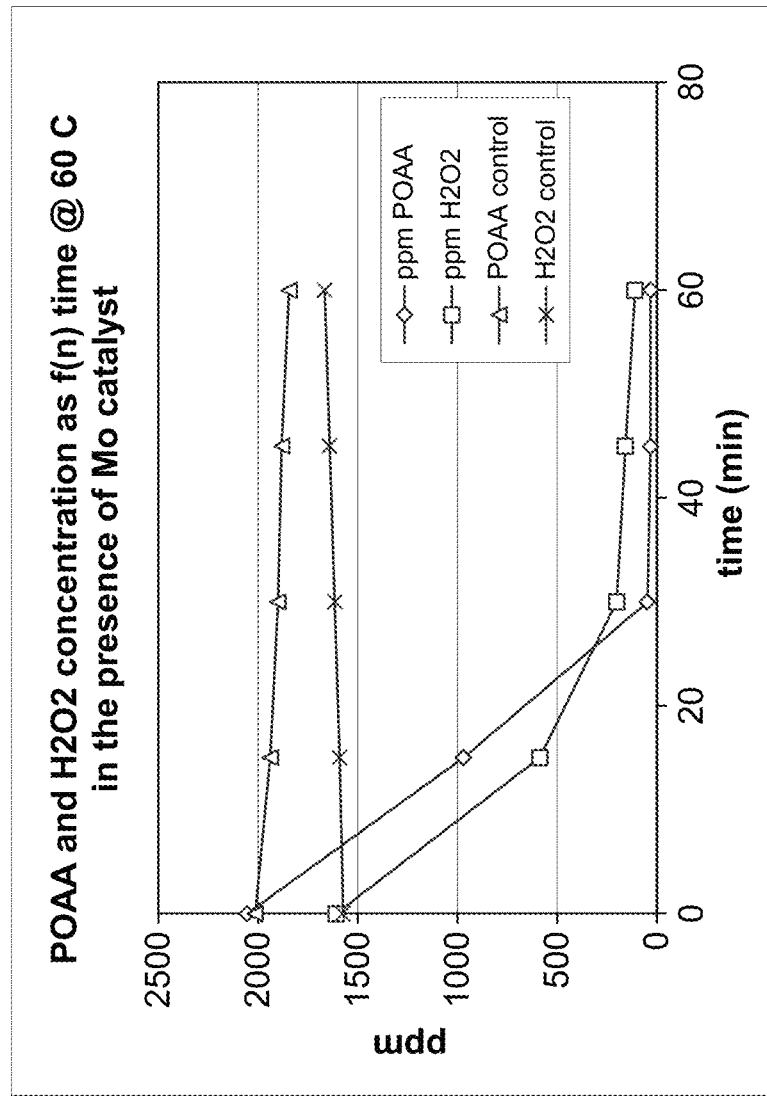
Figure 37:
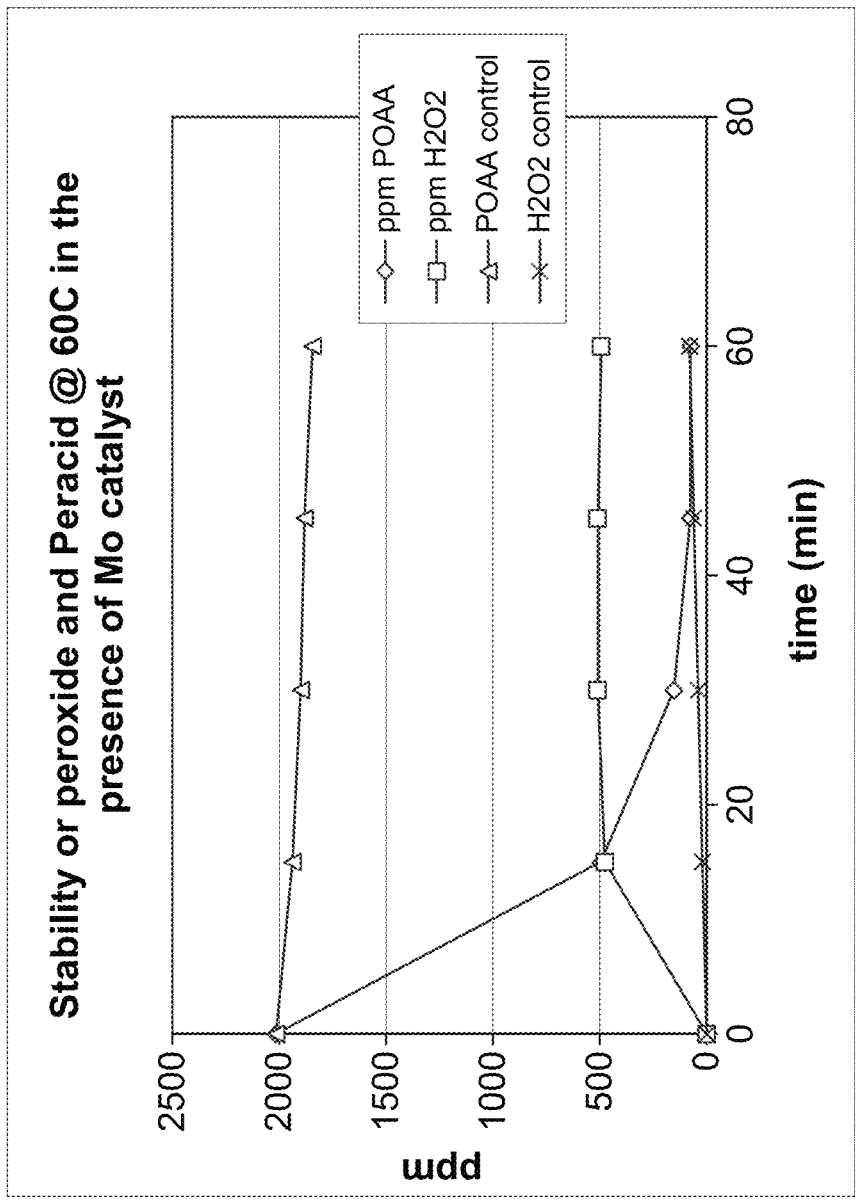

Additional testing using the Mo, molybdenum inorganic peroxide-reducing agent was conducted using a different titration methodology, as outlined above with respect to the NiMo catalyst testing that was re-analyzed. The results are outlined in Table 30 and shown in FIGS. 36-37.

TABLE 30

| time | Titration with catalase | Total Oxygen titration | ppm POAA | ppm $H_2O_2$ | POAA control | $H_2O_2$ control |
|---|---|---|---|---|---|---|
| A | | | | | | |
| 0 | 5.4 | 14.85 | 2052 | 1606.5 | 2014 | 1572.5 |
| 15 | 2.55 | 6 | 969 | 586.5 | 1938 | 1589.5 |
| 30 | 0.12 | 1.3 | 45.6 | 200.6 | 1900 | 1615 |
| 45 | 0.08 | 1 | 30.4 | 156.4 | 1881 | 1640.5 |
| 60 | 0.08 | 0.72 | 30.4 | 108.8 | 1843 | 1666 |
| B (Pre-treated POAA with catalase) | | | | | | |
| 0 | 5.3 | 5.3 | 2014 | 0 | 2014 | 0 |
| 15 | 1.3 | 4.1 | 494 | 476 | 1938 | 20 |
| 30 | 0.4 | 3.4 | 152 | 510 | 1900 | 40 |
| 45 | 0.2 | 3.2 | 76 | 510 | 1881 | 60 |
| 60 | 0.2 | 3.1 | 76 | 493 | 1843 | 80 |

Example 21

Micro efficacy of peracid compositions utilizing various peroxide-reducing agents according to embodiments of the invention was analyzed, as shown in Table 31. The control sample was a contaminated water source from a field water composition used in the field of hydraulic fracturing (i.e. 73,412,793.2 micro equivalents per gram contaminants). Peracid samples with and without hypochlorite were added to the Control contaminated water source and were tested to determine effect on micro efficacy of the use of and sequencing of the potential peroxide-reducing agent. As reference in this example, the POAA employed is a 15% peracetic acid and 10% hydrogen peroxide composition (such as commercially-available as EnviroSan). As set forth in Tables 31-32, the reference to "X2" refers to a second sequence of dosing the POAA and/or Hypochlorite to the Control contaminated water source. For example, a first dose of 250 ppm POAA was added to treat the Control contaminated water source and thereafter a second dose was administered.

According to the Tables 31-32, the amount of active (ppm) POAA and/or hypochlorite in the Control treated water sources is as follows, for example: 250 ppm POAA is equivalent to 37.5 ppm POAA in solution of the Control water source; 250 ppm hydrogen peroxide is equivalent to 25 ppm hydrogen peroxide in solution of the Control water source.

TABLE 31

| Sample | $RLU_{UC1}$ | Sample Volume (mL) | $RLU_{cATP}$ | ATP Conc (pg ATP/g) | Micro Equivs/g | % Reduction |
|---|---|---|---|---|---|---|
| Control | 11725 | 20 | 1721530 | 73412.8 | 73,412,793.2 | |
| Control with POAA 250 ppm (X2) | 11725 | 10 | 5497 | 468.8 | 468,827.3 | 99% |
| Control with Hypo 250 ppm (X2) | 11725 | 10 | 38791 | 3308.4 | 3,308,400.9 | 95% |
| Control with Hypo/POAA 250 ppm each | 11725 | 10 | 34071 | 2905.8 | 2,905,842.2 | 96% |
| Control with POAA/Hypo 250 ppm each | 11725 | 10 | 25606 | 2183.9 | 2,183,880.6 | 97% |
| Control with Hypo 500 ppm | 11725 | 10 | 58401 | 4980.9 | 4,980,895.5 | 93% |
| Control with POAA 500 ppm | 11725 | 10 | 24795 | 2114.7 | 2,114,712.2 | 97% |

Additional evaluation of the process of using peroxide-reducing agents in sequence was further analyzed as shown in Table 32 using additional water samples, including deionized water (i.e. not contaminated), and the Control (as set forth above as a contaminated water source).

TABLE 32

| Samples | Time (min) | POAA ppm meas. | POAA ppm calc. | NaOCl ppm meas. | NaOCl ppm calc. | H2O2 ppm meas. | H2O2 ppm calc. | % Reduction |
|---|---|---|---|---|---|---|---|---|
| DI H2O with Hypo 1000 ppm | 2 | 0.00 | 0 | 137.30 | 300 | 0.00 | 0 | |
| DI H2O with Hypo 1000 ppm | 2 | 0.00 | 0 | 149.02 | 300 | 0.00 | 0 | |
| DI H2O with POAA 500 ppm/Hypo 500 ppm | 2 | 62.64 | 75 | 61.32 | 150 | 23.78 | 50 | |
| DI H2O with POAA 500 ppm/Hypo 500 ppm | 2 | 69.54 | 75 | 68.07 | 150 | 31.95 | 50 | |
| DI H2O with POAA 1000 ppm | 2 | 170.23 | 150 | 0.00 | 0 | 121.85 | 100 | |
| Control with POAA 250 ppm (X2) | 30 | 24.52 | 75 | 0.00 | 0 | 40.74 | 50 | 99.4% |
| Control with Hypo 250 ppm (X2) | 30 | 0.00 | 0 | 7.20 | 150 | 0.00 | 0 | 95.5% |
| Control with Hypo/POAA 250 ppm each | 30 | 1.85 | 37.5 | 3.62 | 75 | 19.87 | 25 | 96.0% |
| Control with POAA/Hypo 250 ppm each | 30 | 0.94 | 37.5 | 1.84 | 75 | 15.15 | 25 | 97.0% |
| Control with Hypo 500 ppm | 30 | 0.00 | 0 | 3.70 | 150 | 0.00 | 0 | 93.2% |
| Control with POAA 500 ppm | 30 | 3.77 | 75 | 0.00 | 0 | 37.12 | 50 | 97.1% |
| DI H2O with POAA 250 ppm (X2) | 30 | 82.12 | 75 | 0.00 | 0 | 66.80 | 50 | |
| DI H2O with Hypo 250 ppm (X2) | 30 | 0.00 | 0 | 81.84 | 150 | 0.00 | 0 | |
| DI H2O with Hypo/POAA 250 ppm each | 30 | 33.84 | 37.5 | 33.13 | 75 | 6.73 | 25 | |
| DI H2O with POAA/Hypo 250 ppm each | 30 | 35.90 | 37.5 | 35.15 | 75 | 6.76 | 25 | |

The results shown in Table 32 demonstrate that hypochlorite has efficacious impact on the decomposition of hydrogen peroxide (in water not containing any biological contamination). The mixed systems showed increased peroxide decomposition compared to the non-mixed peracid systems. This demonstrates the effect of biological contamination in water competing with hydrogen peroxide decay by sodium hypochlorite. More rapid decomposition or decay of the peracetic acid and sodium hypochlorite is observed in conjunction with increased microbial percentage reduction while hydrogen peroxide shows increased stability.

The peracetic acid and sodium hypochlorite are indistinguishable in titration, and are therefore presumed to consist of ½ of the titrateable material; however the focus of the evaluation was solely on the hydrogen peroxide decomposition.

The inventions being thus described, it will be obvious that the same may be varied in many ways. Such variations are not to be regarded as a departure from the spirit and scope of the inventions and all such modifications are intended to be included within the scope of the following claims.

What is claimed is:

1. A method of treating oil or gas field operation water sources comprising:
   treating a percarboxylic acid composition, wherein said percarboxylic acid composition comprising percarboxylic acid and hydrogen peroxide, with an inorganic peroxide-reducing agent to generate an antimicrobial composition, wherein said inorganic peroxide-reducing agent is a hypohalite, and wherein said inorganic peroxide-reducing agent reduces hydrogen peroxide from said percarboxylic acid composition;
   providing the antimicrobial composition to a water source in need of treatment, wherein said water source in need of treatment is selected from the group consisting of drilling fluid water, a fracking water, and a produced water from an oil or gas well, to form a treated water source, wherein the treated water source comprises (i) from 0.5 ppm to 1000 ppm inorganic peroxide-reducing agent; (ii) from about 0 wt-% to about 1 wt-% of hydrogen peroxide; (iii) from about 0.0001 wt-% to about 10.0 wt-% of a $C_1$-$C_{22}$ carboxylic acid; and (iv) from about 0.0001 wt-% to about 10.0 wt-% of a $C_1$-$C_{22}$ percarboxylic acid, wherein the hydrogen peroxide to percarboxylic acid ratio is from about 0:100 to about 1:10 by weight; and
   directing the treated water source into an oil or gas well or disposing of the treated water source.

2. The method of claim 1, wherein the water source in need of treatment comprises produced water.

3. The method of claim 2, wherein the water source comprises at least 1 wt-% produced water.

4. The method of claim 1, wherein said hypohalite is hypochlorite.

5. The method of claim 1, wherein the antimicrobial composition does not interfere with friction reducers, viscosity enhancers, other functional ingredients found in the water source, or combinations thereof.

6. The method of claim 1, wherein the percarboxylic acid stability is improved through the treating of the percarboxylic acid composition with the inorganic peroxide-reducing agent to minimize hydrogen peroxide concentration within the percarboxylic acid composition, and wherein the concentration of the $C_1$-$C_{22}$ carboxylic acid is from about 0.0001 wt-% to about 5.0 wt-%, and wherein the concentration of the $C_1$-$C_{22}$ percarboxylic acid is from about 0.0001 wt-% to about 5.0 wt-%, and wherein hydrogen peroxide is from about 0 wt-% to about 0.5 wt-%.

7. The method of claim 1, wherein the percarboxylic acid is peracetic acid and the carboxylic acid is acetic acid.

8. The method of claim 1, wherein the method further comprises adding an acidulant to the water source in need of treatment before the addition of the antimicrobial composition.

9. A method of treating oil or gas field operation water sources comprising:
adding a percarboxylic acid composition, wherein said percarboxylic acid composition comprising percarboxylic acid and hydrogen peroxide, and an inorganic peroxide-reducing agent, wherein said inorganic peroxide reducing agent is a hypohalite, to a water source in need of treatment, wherein said water source in need of treatment is selected from the group consisting of drilling fluid water, a fracking water, and a produced water from an oil or gas well, and reducing the hydrogen peroxide with the inorganic peroxide-reducing agent, to form a treated water source having a hydrogen peroxide to percarboxylic acid ratio from about 0:100 to about 1:10 by weight, wherein said treated water source comprises (i) less than about 1000 ppm of the inorganic peroxide-reducing agent; (ii) from about 0 wt-% to about 1 wt-% hydrogen peroxide; (iii) from about 0.0001 wt-% to about 10.0 wt-% of a $C_1$-$C_{22}$ carboxylic acid; and (iv) from about 0.0001 wt-% to about 10.0 wt-% of a $C_1$-$C_{22}$ percarboxylic acid;
wherein the treated water source reduces corrosion caused by hydrogen peroxide and microbial-induced corrosion,
and wherein the antimicrobial composition does not interfere with friction reducers, viscosity enhancers, other functional ingredients found in the water source or combinations thereof.

10. The method of claim 9, wherein the water source in need of treatment comprises produced water.

11. The method of claim 10, wherein the water source comprises at least 1 wt-% produced water.

12. The method of claim 9, wherein the hypohalite is hypochlorite.

13. The method of claim 9, further comprising the steps of directing the treated water source into an oil or gas well or disposing of the treated water source.

14. The method of claim 9, wherein said reducing the hydrogen peroxide with the inorganic peroxide-reducing agent improves the percarboxylic acid stability.

15. The method of claim 9, wherein the percarboxylic acid is peracetic acid and the carboxylic acid is acetic acid.

16. The method of claim 9, wherein the adding of the percarboxylic acid composition and the peroxide-reducing agent to the water source occurs on an at least every 5 day dosing cycle.

17. The method of claim 9, wherein the method further comprises adding an acidulant to the water source in need of treatment before the addition of the percarboxylic acid and inorganic peroxide-reducing agent.

18. A method of treating oil or gas field operation water sources comprising:
forming a treated water source by (a) treating a percarboxylic acid composition, wherein said percarboxylic acid composition comprising percarboxylic acid and hydrogen peroxide, with an inorganic peroxide-reducing agent, wherein said inorganic peroxide-reducing agent is a hypohalite, to reduce the hydrogen peroxide in the percarboxylic acid composition, and generate an antimicrobial composition, then providing the antimicrobial composition to a water source in need of treatment, wherein said water source in need of treatment selected from the group consisting of drilling fluid water, a fracking water, and a produced water from an oil or gas well, or (b) adding said percarboxylic acid composition and said inorganic peroxide-reducing agent to said water source in need of treatment, and reducing the hydrogen peroxide with the inorganic peroxide-reducing agent;
wherein the treated water source comprises (i) from 0.5 ppm to 1000 ppm inorganic peroxide-reducing agent, (ii) from about 0 wt-% to about 1 wt-% of hydrogen peroxide; (iii) from about 0.0001 wt-% to about 10.0 wt-% of a $C_1$-$C_{22}$ carboxylic acid; and (iv) from about 0.0001 wt-% to about 10.0 wt-% of a $C_1$-$C_{22}$ percarboxylic acid, wherein the hydrogen peroxide to percarboxylic acid ratio is from about 0:100 to about 1:10 by weight; and
directing the treated water source into an oil or gas well or disposing of the treated water source,
wherein the treated water source reduces corrosion caused by hydrogen peroxide and microbial-induced corrosion, and does not interfere with friction reducers, viscosity enhancers, or other functional ingredients found in the water source.

19. The method of claim 18, wherein the hypohalite is hypochlorite.

20. The method of claim 18, wherein the percarboxylic acid is peracetic acid and the carboxylic acid is acetic acid.

* * * * *